United States Patent
Moslin et al.

(10) Patent No.: US 9,663,467 B2
(45) Date of Patent: May 30, 2017

(54) ALKYL-AMIDE-SUBSTITUTED PYRIDYL COMPOUNDS USEFUL AS MODULATORS OF IL-12, IL-23 AND/OR IFNα RESPONSES

(71) Applicant: BRISTOL-MYERS SQUIBB COMPANY, Princeton, NJ (US)

(72) Inventors: Ryan M. Moslin, Princeton, NJ (US); David S. Weinstein, East Windsor, NJ (US); Stephen T. Wrobleski, Flemington, NJ (US); Yanlei Zhang, Princeton Junction, NJ (US); John S. Tokarski, Princeton, NJ (US); Michael E. Mertzman, New Hope, PA (US); Chunjian Liu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/034,915

(22) PCT Filed: Jan. 16, 2014

(86) PCT No.: PCT/US2014/011769
§ 371 (c)(1),
(2) Date: May 6, 2016

(87) PCT Pub. No.: WO2015/069310
PCT Pub. Date: May 14, 2015

(65) Prior Publication Data
US 2016/0280649 A1    Sep. 29, 2016

(30) Foreign Application Priority Data

Nov. 7, 2013 (AR) ................. P130104090

(51) Int. Cl.
| C07D 213/56 | (2006.01) |
| --- | --- |
| C07D 405/12 | (2006.01) |
| C07D 401/12 | (2006.01) |
| C07D 213/82 | (2006.01) |
| C07D 413/12 | (2006.01) |
| C07D 417/12 | (2006.01) |
| C07B 59/00 | (2006.01) |

(52) U.S. Cl.
CPC .......... *C07D 213/82* (2013.01); *C07B 59/002* (2013.01); *C07D 401/12* (2013.01); *C07D 405/12* (2013.01); *C07D 413/12* (2013.01); *C07D 417/12* (2013.01); *C07B 2200/05* (2013.01); *C07D 213/56* (2013.01)

(58) Field of Classification Search
CPC ... C07D 213/56; C07D 405/12; C07D 401/12
See application file for complete search history.

(56) References Cited

U.S. PATENT DOCUMENTS 9,315,494 B2    4/2016    Moslin et al.

FOREIGN PATENT DOCUMENTS

| WO | WO 2010/129802 | 11/2010 |
| --- | --- | --- |
| WO | WO 2010/142752 | 12/2010 |
| WO | WO 2013/054351 | 4/2013 |
| WO | WO 2013/092854 | 6/2013 |
| WO | WO2014/074660 | 5/2014 |
| WO | WO2014/074661 | 5/2014 |
| WO | WO2014/074670 | 5/2014 |
| WO | WO2015/089143 | 6/2015 |

*Primary Examiner* — Samira Jean-Louis
(74) *Attorney, Agent, or Firm* — Elliott Korsen

(57) ABSTRACT

Compounds having the following formula (I): or a stereoisomer or a pharmaceutically-acceptable salt thereof, wherein $R^1$, $R^2$, $R^3$, $R^4$, and $R^5$ are as defined herein, are useful in the modulation of IL-12, IL-23 and/or IFNα by acting on Tyk-2 to cause signal transduction inhibition.

(I)

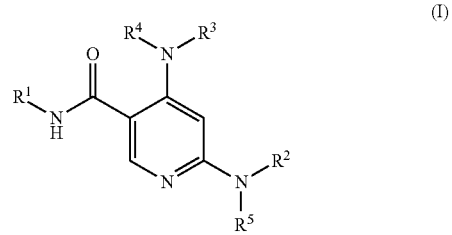

7 Claims, No Drawings

ALKYL-AMIDE-SUBSTITUTED PYRIDYL COMPOUNDS USEFUL AS MODULATORS OF IL-12, IL-23 AND/OR IFNα RESPONSES

FIELD OF THE INVENTION

This invention relates to compounds useful in the modulation of IL-12, IL-23 and/or IFNα by acting on Tyk-2 to cause signal transduction inhibition. Provided herein are alkyl-amide-substituted pyridyl compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", Nat. Rev. Rheumatol., 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain* 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.* 90:636-647 (2012); Graham, D. et al., "Association of polymorphisms across the tyrosine kinase gene, TYK2 in UK SLE families", *Rheumatology (Oxford)* 46:927-930 (2007); Eyre, S. et al., "High-density genetic mapping identifies new susceptibility loci for rheumatoid arthritis", *Nat. Genet.* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

Provided herein is at least one chemical entity chosen from compounds of formula I:

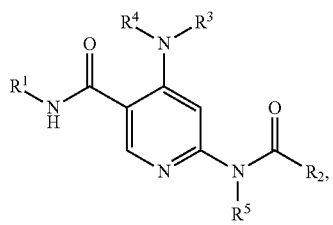

or stereoisomers, tautomers, pharmaceutically-acceptable salts, solvates, or prodrugs thereof, wherein:

$R^1$ is $C_{1-3}$alkyl optionally substituted by 0-7 $R^{1a}$;

$R^{1a}$ at each occurrence is independently hydrogen, deuterium, F, Cl, Br, $CF_3$ or CN;

$R^2$ is $C_{1-6}$ alkyl substituted with 0-4 $R^{2a}$, $C_{3-6}$ cycloalkyl substituted with 0-4 $R^{2a}$, $C_{6-10}$ aryl substituted with 0-4 $R^{2a}$, a 5-14 membered heterocycle containing 1-4 heteroatoms selected from N, O, and S, substituted with 0-4 $R^{2a}$, $NR^6R^6$ or $OR^b$;

$R^{2a}$ at each occurrence is independently hydrogen, =O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, $(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, —$(CH_2)_r$-3-14 membered carbocycle substituted with 0-1 $R^a$ or a-$(CH_2)_r$-5-7 membered heterocycle comprising carbon atoms or 1-4 heteroatoms selected from N, O, and $S(O)_p$ substituted with 0-2 $R^a$;

or one $R^{2a}$ and another $R^{2a}$, together with the atoms to which they are attached, combine to form a fused 5-6 membered ring wherein said fused ring may be substituted with 0-2 $R^a$;

$R^3$ is —$(CH_2)_r$-3-14 membered carbocycle substituted 0-5 $R^{3a}$;

$R^{3a}$ at each occurrence is independently hydrogen, =O, halo (F), $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, —$(CH_2)_r$-3-14 membered carbocycle substituted with 0-3 $R^a$ or a —$(CH_2)_r$-5-10 membered heterocycle comprising carbon atoms and 1-4 heteroatoms selected from N, O, and $S(O)_p$ substituted with 0-3 $R^a$;

or two $R^{1a}$, together with the atoms to which they are attached, combine to form a fused ring wherein said ring is selected from phenyl and a 5-7 membered heterocycle comprising carbon atoms and 1-4 heteroatoms selected from N, S or O, said fused ring may be further substituted by $R^a$;

$R^4$ and $R^5$ are independently hydrogen, $C_{1-4}$ alkyl substituted with 0-1 $R^f$, $(CH_2)_r$-phenyl substituted with 0-3 $R^d$, or a —$(CH_2)$-5-7 membered heterocycle comprising carbon atoms and 1-4 heteroatoms selected from N, O, and $S(O)_p$;

$R^6$ and $R^{11}$ at each occurrence are independently hydrogen, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

$R^a$ at each occurrence is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$alkyl substituted with 0-3 $R^f$, $C_{1-6}$haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$ substituted with 0-3 $R^f$;

$R^b$ at each occurrence is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-3 $R^f$, or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ at each occurrence is independently hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ at each occurrence is independently selected from hydrogen, $C_{1-6}$ alkyl, $C_{3-6}$ cycloalkyl and $(CH_2)_r$-phenyl substituted with 0-3 $R^f$;

$R^f$ independently at each occurrence is hydrogen, halo, CN, $NH_2$, OH, $C_{3-6}$ cycloalkyl, $CF_3$, $O(C_{1-6}alkyl)$ or a —$(CH_2)_r$-5-7 membered heteroaryl comprising carbon atoms and 1-4 heteroatoms selected from N, O, and $S(O)_p$;

p is 0, 1, or 2; and r is 0, 1, 2, 3, or 4.

In another embodiment are provided compounds of formula I, or stereoisomers, tautomers, pharmaceutically-acceptable salts, solvates, or prodrugs thereof, wherein $R^2$ is methyl, ethyl, propyl, furyl, pyranyl, cyclopropyl, cyclobutyl or cyclohexyl, cyclopentyl, pyridyl, pyrimidinyl, pyridazinyl, pyrazinyl, quinolinyl or pyrrolopyridinyl, each group substituted as valence allows by 0-4 groups selected from $R^{2a}$; or $R^2$ is $NR^6R^6$ or $OR^b$.

In another embodiment are provided compounds of formula I, or stereoisomers, tautomers, pharmaceutically-acceptable salts, solvates, or prodrugs thereof, wherein $R^3$ is $C_{3-6}$cycloalkyl or $C_{6-10}$ aryl, each group substituted with 0-5 $R^{3a}$. In a more preferred embodiment, $R^3$ is preferably phenyl substituted with 0-5 $R^{3a}$.

In another embodiment, there is provided a compound of formula I, or stereoisomers, tautomers, pharmaceutically-acceptable salts, solvates, or prodrugs thereof, wherein both $R^4$ and $R^5$ are hydrogen.

In another embodiment, there is provided a compound of formula I, wherein

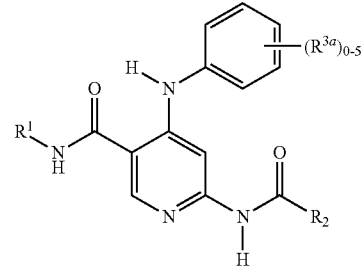

or stereoisomers, tautomers, pharmaceutically-acceptable salts, solvates, or prodrugs thereof, wherein:

$R^1$ is $C_{1-3}$alkyl substituted by 0-7 deuterium atoms;

$R^2$ is methyl, ethyl, propyl, furyl, pyranyl, cyclopropyl, cyclobutyl or cyclohexyl, cyclopentyl, pyridyl, pyrimidinyl, pyridazinyl, pyrazinyl, quinolinyl or pyrrolopyridinyl, each group substituted as valence allows by 0-4 groups selected from $R^{2a}$;

or $R^2$ is $NR^6R^6$ or $OR^b$;

$R^{2a}$ at each occurrence is independently hydrogen, —$(CH_2)_rOR^b$, $(CH_2)_rNR^{11}R^{11}$, $C_{1-6}$ haloalkyl ($CF_3$), —$(CH_2)_r$-3-14 membered carbocycle substituted with 0-1 $R^a$(phenyl), —$(CH_2)_r$-5-7 membered heterocycle comprising carbon atoms or 1-4 heteroatoms selected from N, O, and $S(O)_p$ substituted with 0-2 $R^a$ (pyridyl);

or one $R^{2a}$ and another $R^{2a}$, together with the atoms to which they are attached, combine to form a fused 5-6 membered ring (phenyl) wherein said fused ring may be substituted with 0-2 $R^a$;

$R^3$ is $C_{3-6}$cycloalkyl or $C_{6-10}$ aryl, each group substituted with 0-5 $R^{3a}$ ($R^3$ is preferably phenyl substituted with 0-5 $R^{3a}$);

$R^{3a}$ at each occurrence is independently hydrogen, halo (F), —$(CH_2)_rOR^b$ or —$S(O)_pR^c$;

$R^6$ at each occurrence is independently hydrogen or $C_{1-6}$ alkyl substituted with 0-3 $R^f$ (methyl);

$R^{11}$ at each occurrence is hydrogen;

$R^a$ is independently at each occurrence hydrogen, —$(CH_2)_rOR^b$ or $C_{1-6}$ alkyl substituted with 0-3 $R^f$ (methyl);

$R^b$ is independently at each occurrence hydrogen or $C_{1-6}$ alkyl substituted with 0-3 $R^d$ (preferably $R^b$ is methyl);

$R^c$ is $C_{1-6}$ alkyl substituted with 0-3 $R^f$ (preferably $R^c$ is methyl);

$R^d$ at each occurrence is independently hydrogen, halo (preferably halo is F) or —OH;

$R^f$ at each occurrence is independently hydrogen, halo, CN, OH or O($C_{1-6}$alkyl);

p is 0, 1 or 2; and r is 0, 1 or 2.

In another, preferred embodiment, there is provided a compound of formula I, or stereoisomers, tautomers, pharmaceutically-acceptable salts, solvates, or prodrugs thereof, wherein:

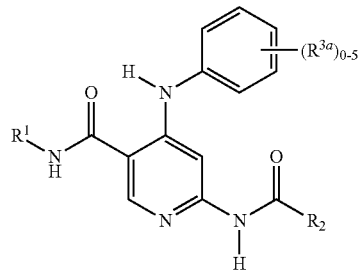

or stereoisomers, tautomers, pharmaceutically-acceptable salts, solvates, or prodrugs thereof, wherein:

$R^1$ is $C_{1-3}$alkyl substituted by 0-7 deuterium atoms;

$R^2$ is methyl, ethyl, propyl, furyl, pyranyl, cyclopropyl, cyclobutyl or cyclohexyl, cyclopentyl, pyridyl, pyrimidinyl, pyridazinyl, pyrazinyl, quinolinyl or pyrrolopyridinyl, each group substituted as valence allows by 0-4 groups selected from $R^{2a}$;

or $R^2$ is $NR^6R^6$ or $OR^b$;

$R^{2a}$ at each occurrence is independently hydrogen, —$(CH_2)_rOR^b$, $(CH_2)_rNR^{11}R^{11}$, $C_{1-6}$ haloalkyl ($CF_3$), —$(CH_2)_r$-3-14 membered carbocycle substituted with 0-1 $R^a$, —$(CH_2)_r$-5-7 membered heterocycle comprising carbon atoms or 1-4 heteroatoms selected from N, O, and $S(O)_p$ substituted with 0-2 $R^a$;

or one $R^{2a}$ and another $R^{2a}$, together with the atoms to which they are attached, combine to form a fused 5-6 membered ring wherein said fused ring may be substituted with 0-2 $R^a$;

$R^{3a}$ at each occurrence is independently hydrogen, halo (F), —$(CH_2)_rOR^b$, —$(CH_2)_r$-5-7 membered heterocycle comprising carbon atoms and 1-4 heteroatoms selected from N, O, and $S(O)_p$ substituted with 0-3 $R^a$ or —$S(O)_pR^c$;

$R^6$ at each occurrence is independently hydrogen, phenyl or $C_{1-6}$ alkyl substituted with 0-3 $R^f$;

$R^{11}$ is at each occurrence independently hydrogen, cyclopropyl or $C_{1-4}$alkyl substituted with 0-1 $R^f$;

$R^a$ at each occurrence is hydrogen, halo, —$(CH_2)_rOR^b$ or $C_{1-6}$ alkyl substituted with 0-3 $R^f$;

$R^b$ at each occurrence is hydrogen or $C_{1-6}$ alkyl substituted with 0-3 $R^d$;

$R^c$ is $C_{1-6}$ alkyl substituted with 0-3 $R^f$ (methyl);

$R^d$ at each occurrence is independently hydrogen, halo or —OH;

$R^f$ at each occurrence is independently hydrogen, halo, CN, OH or O($C_{1-6}$alkyl);

p is 0, 1 or 2; and r is 0, 1 or 2.

In an alternate embodiment, there is provided a compound of formula I, or stereoisomers, tautomers, pharmaceutically-acceptable salts, solvates, or prodrugs thereof, wherein $R^2$ is methyl, ethyl, propyl (n and i), furyl, pyranyl, cyclopropyl, pyridyl, cyclobutyl or cyclohexyl, each group substituted by 0-4 groups selected from $R^{2a}$. In a preferred embodiment, $R^2$ is cyclopropyl substituted by 0-4 groups selected from $R^{2a}$.

In another embodiment, there is provided a compound, or stereoisomers, tautomers, pharmaceutically-acceptable salts, solvates, or prodrugs thereof, wherein $R^2$ is $NR^6R^6$.

In another embodiment, there is provided a compound, or stereoisomers, tautomers, pharmaceutically-acceptable salts, solvates, or prodrugs thereof, wherein $R^2$ is $OR^b$.

In a more preferred embodiment, compounds of formula (I), or stereoisomers, tautomers, pharmaceutically-acceptable salts, solvates, or prodrugs thereof, are provided wherein $R^2$ is selected from:

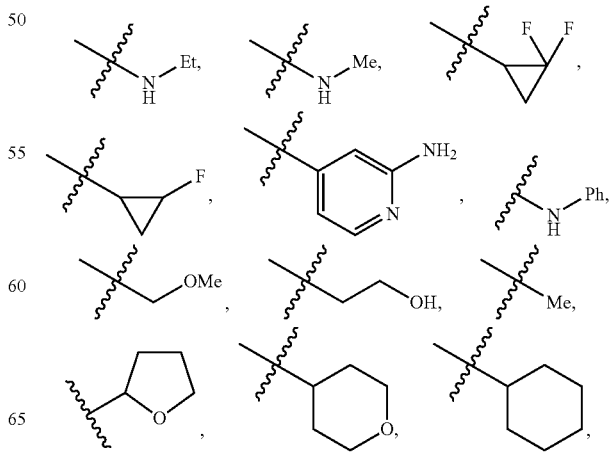

-continued

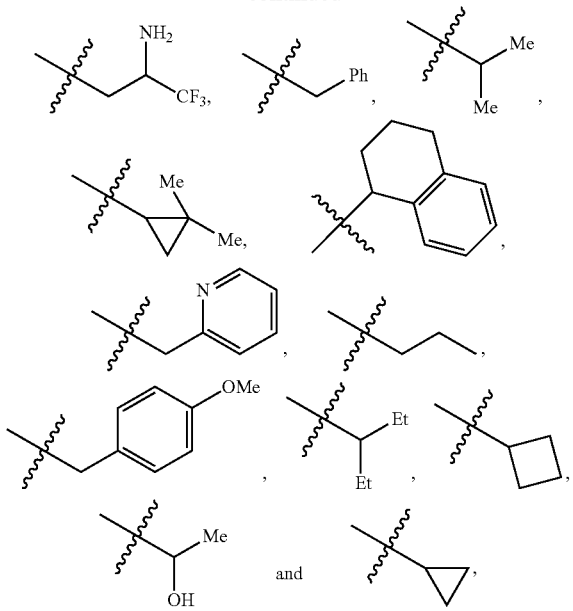

In another, more preferred embodiment, there is provided a compound of formula (I), or stereoisomers, tautomers, pharmaceutically-acceptable salts, solvates, or prodrugs thereof, wherein:

$R^{3a}$ at each occurrence independently is hydrogen, Ph, CN, NH$_2$, OCF3, OR$^b$, halo, cycloalkyl, C(O)NR$^{11}$R$^{11}$ S(O)$_2$NR$_{11}$R$_{11}$, C(O)R$^b$, SO$_p$R$^c$, NR$^b$SO$_p$R$^c$, NR$^b$C(O)R$^c$, haloalkyl (CF$_3$), CN, a 5-7 membered heterocycle comprising carbon atoms and 1-3 heteroatoms selected from N, S or O substituted with 0-3 R$^a$ and C$_{1-6}$ alkyl substituted with 0-3 R$^a$; or one R$^{3a}$ and a second R$^{3a}$ together with the atoms to which they are attached combine to form a fused ring wherein the ring is phenyl or a 5-7 membered heterocycle comprising carbon atoms and 1-4 heteroatoms selected from N, S or O;

$R^{11}$ is hydrogen, cyclopropyl or C$_{1-4}$alkyl substituted with 0-1 R$^f$;

$R^a$ is at each occurrence independently halo or OR$^b$;

$R^b$ is at each occurrence independently hydrogen, a 5-7 membered heterocycle comprising carbon atoms and 1-4 heteroatoms selected from N, S or O substituted with 0-3 R$^f$ or C$_{1-6}$ alkyl substituted with 0-3 R$^d$;

$R^d$ is at each occurrence independently halo (preferably F) or OH;

$R^c$ is at each occurrence independently C$_{1-6}$ alkyl substituted with 0-3 R$^f$;

$R^f$ is at each occurrence independently hydrogen, halo or OH; and p is 2.

In another, more preferred embodiment, there is provided a compound of formula (I), or stereoisomers, tautomers, pharmaceutically-acceptable salts, solvates, or prodrugs thereof, wherein R$^3$ has acceptable salt thereof, wherein R$^3$ has the formula,

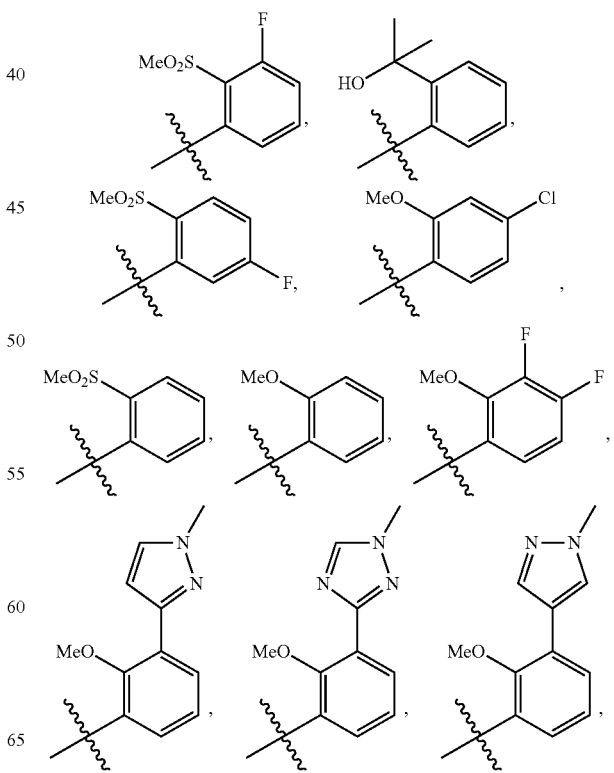

where:
$R^{3aa}$ is C$_{1-6}$ alkyl substituted with 0-3 R$^{a2}$, S(O)$_p$R$^{c2}$ or OR$^{b2}$;

$R^{3ab}$, R$^{3ac}$, or R$^{3ad}$ are independently hydrogen, Cl, F, or Br;

or R$^{3ab}$, R$^{3ac}$, or R$^{3ad}$ are independently pyrazolyl, thiazolyl or oxadiazolyl, each group substituted with 0-3 R$^{a2}$;

$R^{11}$ at each occurrence independently is hydrogen;

$R^{a2}$ is at each occurrence independently halo, OH or C$_{1-6}$ alkyl substituted with 0-3 R$^{f2}$;

$R^{b2}$ is hydrogen or C$_{1-6}$ alkyl substituted with 0-2 R$^{d2}$;

$R^{c2}$ is C$_{1-6}$ alkyl substituted with 0-3 R$^{f2}$;

$R^{d2}$ independently at each occurrence is F or OH;

$R^{f2}$ is halo, CN or OH; and p is 0-2.

In a further embodiment, there is provided a compound of formula I, or stereoisomers, tautomers, pharmaceutically-acceptable salts, solvates, or prodrugs thereof, wherein R$^{3aa}$ is S(O)$_p$CH$_3$ or OCH$_3$. Preferably p is 1 or 2, more preferably 2.

In a more preferred embodiment, there is provided a compound of formula I, or stereoisomers, tautomers, pharmaceutically-acceptable salts, solvates, or prodrugs thereof, wherein R$^3$ is selected from -continued

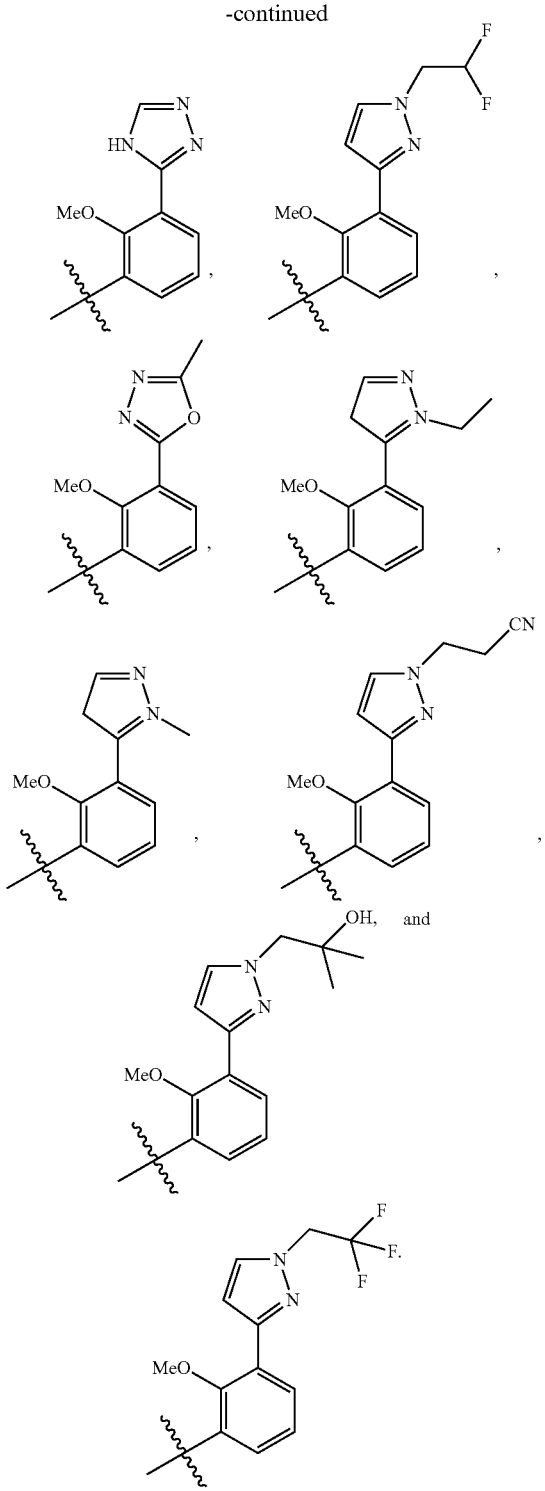

In a more preferred embodiment, there is provided a compound of formula I, or stereoisomers, tautomers, pharmaceutically-acceptable salts, solvates, or prodrugs thereof, wherein $R^1$ is $CH_3$, $C_2H_5$, $CD_3$, or $CD_2CD_3$ (preferably $CH_3$ or $CD_3$).

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα, comprising compounds of formula I, or pharmaceutically-acceptable salts thereof, and pharmaceutically-acceptable carriers or diluents.

The invention further relates to methods of treating diseases associated with the modulation of IL-12, IL-23 and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of these diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I, or pharmaceutically-acceptable salt thereof, in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

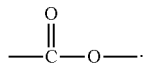

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl(tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

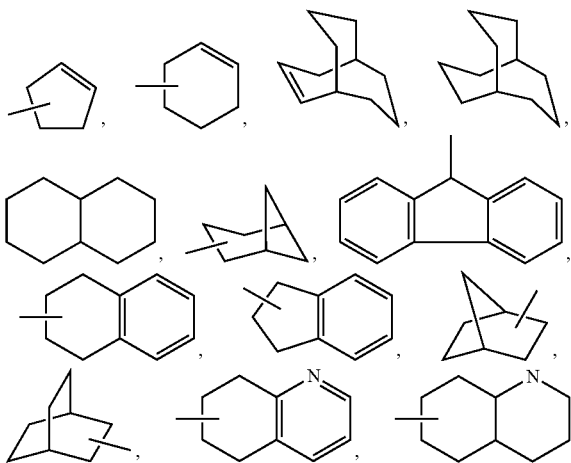

and the like, which optionally may be substituted at any available atoms of the ring(s). Preferred cycloalkyl groups include cyclopropyl, cyclopentyl, cyclohexyl, and

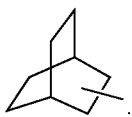

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

Thus, examples of aryl groups include:

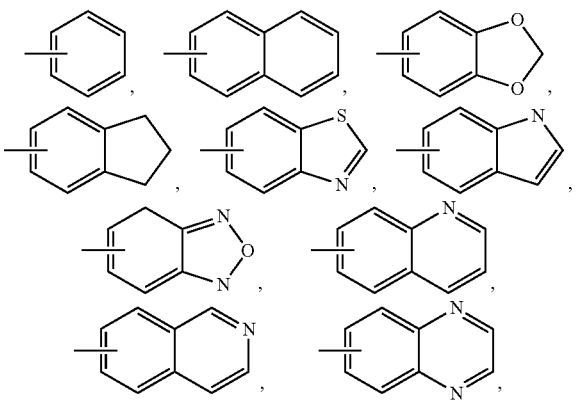

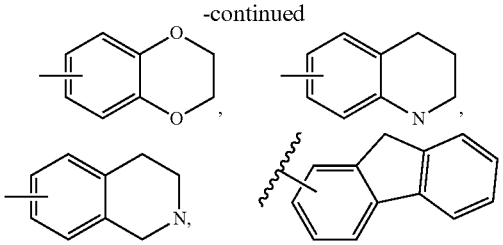

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

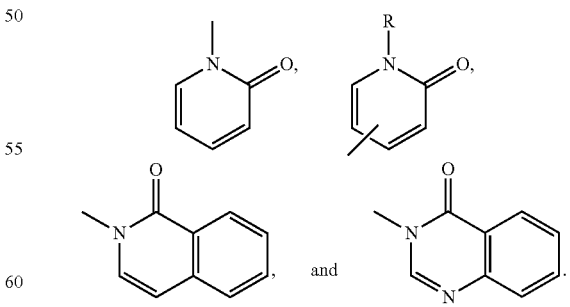

and

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

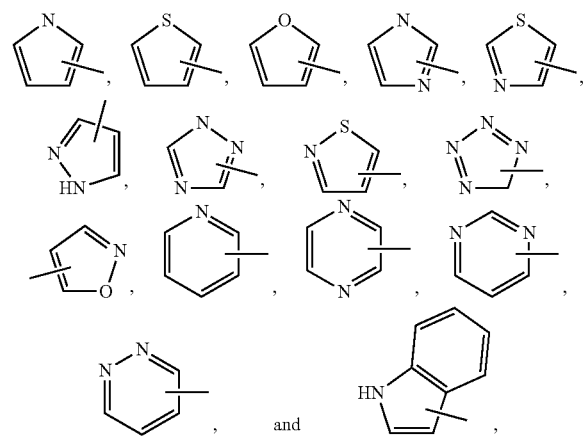

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- or IFNα-associated condition" or "IL-23-, IL-12- or IFNα-associated disease or disorder" are used herein, each is intended to encompass all of the conditions identified above as if repeated at length, as well as any other condition that is affected by IL-23, IL-12 or IFNα.

The present invention thus provides methods for treating such conditions, comprising administering to a subject in need thereof a therapeutically-effective amount of at least one compound of Formula I or a salt thereof "Therapeutically effective amount" is intended to include an amount of a compound of the present invention that is effective when administered alone or in combination to inhibit IL-23, IL-12 or IFNα function and/or treat diseases.

The methods of treating IL-23-, IL-12- or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 or IFNα function and/or treat diseases associated with IL-23, IL-12 or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Biological Assays

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 μg/mL Copper His-Tag scintillation proximity assay beads (Perkin Elmer, Catalog #RPNQ0095) in 50 mM HEPES, pH 7.5, containing 100 μg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The $IC_{50}$ value is defined as the concentration of test compound required to inhibit radiolabeled probe binding by 50%.

Protein Sequence of recombinant Hig-tagged Tyk2 (575-869):

```
MGSSHHHHHH SSGETVRFQG HMNLSQLSFH RVDQKEITQL

SHLGQGTRTN VYEGRLRVEG SGDPEEGKMDDEDPLVPGRD

RGQELRVVLK VLDPSHHDIA LAFYETASLM SQVSHTHLAF

VHGVCVRGPE NIMVTEYVEHGPLDVWLRRE RGHVPMAWKM

VVAQQLASAL SYLENKNLVH GNVCGRNILL ARLGLAEGTS

PFIKLSDPGVGLGALSREER VERIPWLAPE CLPGGANSLS

TAMDKWGFGA TLLEICFDGE APLQSRSPSE

KEHFYQRQHRLPEPSCPQLA TLTSQCLTYE PTQRPSFRTI

LRDLTRL.
```

The preparation of radiolabeled probe, (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below:

2-([$^3$H]Methylsulfonyl)benzoic acid: 2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in $CH_2Cl_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna 5 μm C18 (10×250 cm); A: MeOH/$H_2O$=15/85 (0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5μ, C18 (4.6×150 cm); A: $H_2O$ (0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL.

(R)—N-(1-(3-(8-Methyl-5-(methylamino)-8H-imidazo[4,5-d]thiazolo[5,4-b]pyridin-2-yl)phenyl)ethyl)-2-([$^3$H]methylsulfonyl)benzamide: A solution of 2-([$^3$H]methylsulfonyl)benzoic acid (23.2 mCi) in acetonitrile was added to a 5 mL round-bottomed flask which was then attached to a vacuum line and carefully evaporated to dryness. (R)-2-(3-(1-Aminoethyl)phenyl)-N,8-dimethyl-8H-imidazo[4,5-d] thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5μ, C18 (4.6×150 cm); A: $H_2O$ (0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)—N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5μ C18 (10×250 cm); A: MeOH/$H_2O$=50/50 (0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

Kit225 T Cell Assay

Kit225 T cells with a stably-integrated STAT-dependent luciferase reporter were plated in RPMI (Gibco) containing 10% heat-inactivated FBS (Gibco) and 100 U/mL PenStrep (Gibco). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (Promega) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response ($IC_{50}$) as derived by non-linear regression analysis.

Assay Data

| Example | Probe Displacement Data ($EC_{50}$, μM) | IL-23 Kit225 Reporter, LE ($IC_{50}$, μM) | IFNa Kit225 Reporter, LE ($IC_{50}$, μM) |
| --- | --- | --- | --- |
| 1 | 0.02 | 0.30 | 0.24 |
| 2 | 0.43 | 7.06 | 12.50 |
| 3 | 0.83 | 6.52 | 12.50 |
| 4 | 0.76 | 2.09 | 12.50 |
| 5 | 0.80 | 1.88 | 8.93 |
| 6 | 0.12 | 1.16 | 1.11 |
| 7 | 0.46 | 0.40 | 4.21 |
| 8 | 0.25 | 4.68 | 1.00 |
| 9 | 0.94 | 13.28 | 2.56 |
| 10 | 0.38 | 4.55 | 6.03 |
| 11 | 0.24 | 2.95 | 2.49 |
| 12 | 0.23 | 4.42 | 0.58 |
| 13 | 1.44 | 12.50 | 12.50 |
| 14 | 0.17 | 3.15 | 0.87 |
| 15 | 0.05 | 0.69 | 0.34 |
| 16 | 0.09 | 12.50 | 3.37 |
| 17 | 0.20 | 11.43 | 9.54 |
| 18 | 0.54 | 6.61 | 9.91 |
| 19 | 0.72 | 5.69 | 8.51 |
| 20 | 0.15 | 1.44 | 1.20 |
| 21 | 0.14 | 2.26 | 1.85 |
| 22 | 0.08 | 2.12 | 1.24 |
| 23 | 1.02 | 12.50 | 3.89 |
| 24 | 0.42 | 11.23 | 7.24 |
| 25 | 0.04 | 0.23 | 0.10 |
| 26 | 0.13 | 3.25 | 6.71 |
| 27 | 0.29 | 3.17 | 3.06 |
| 28 | 0.01 | 0.07 | 0.04 |
| 29 | 5.46E−03 | 0.02 | 0.03 |
| 30 | 6.17E−03 | 0.03 | 0.01 |
| 31 | 3.81E−03 | 4.78E−03 | 0.01 |
| 32 | 1.63E−03 | 7.31E−03 | 7.05E−03 |
| 33 | 5.34E−03 | 0.11 | 0.09 |
| 34 | 6.42E−03 | 0.02 | 8.73E−03 |
| 35 | 0.04 | 0.06 | 0.28 |
| 36 | 4.20E−03 | 0.10 | 0.04 |
| 37 | 3.52E−03 | 0.12 | 0.07 |
| 38 | 0.16 | 1.52 | 1.66 |
| 39 | 0.02 | 0.08 | 0.16 |
| 40 | 3.86E−03 | 0.17 | 0.16 |
| 41 | 2.74E−03 | 0.19 | 0.09 |
| 42 | 7.19E−03 | 0.05 | 0.02 |
| 43 | 2.54E−03 | 0.06 | 0.02 |
| 44 | 1.52E−03 | 2.29E−03 | 1.17E−03 |
| 45 | 5.56E−03 | 0.01 | 0.01 |
| 46 | 4.59E−03 | 0.022 | 0.013 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Several of the compounds described were chiral, some were prepared as racemic mixtures, while others were prepared as a single enantiomer. In each case the preparation of the homochiral examples, or the preparation of the opposite enantiomer, may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

Scheme 1. Coupling of halo-pyridine II with amide III

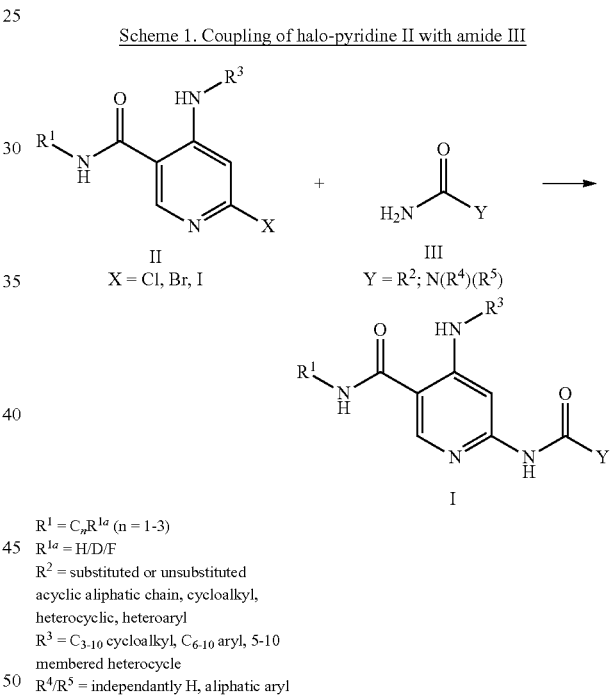

$R^1 = C_nR^{1a}$ (n = 1-3)
$R^{1a}$ = H/D/F
$R^2$ = substituted or unsubstituted acyclic aliphatic chain, cycloalkyl, heterocyclic, heteroaryl
$R^3 = C_{3-10}$ cycloalkyl, $C_{6-10}$ aryl, 5-10 membered heterocycle
$R^4/R^5$ = independantly H, aliphatic aryl Scheme 1 illustrates the preparation of title compounds of the invention (I) from intermediate halo-pyridines (II) and amide/urea (III). This coupling may be affected by many of the ways known to achieve displacement of 2-halo-pyridines by such groups. This includes, but is not limited to, the palladium catalyzed N-arylation of amides. A variety of palladium sources can be used to affect the coupling including both palladium(II) salts (for example palladium diacetate) as well as neutral palladium (such as tetrakis triphenylphosphine palladium or tris(dibenzylideneacetone) dipalladium). A large number of catalyst ligands are suitable for this transformation including bis(diphenylphosphino)-9,9-dimethylxanthene (Xantphos) and 2-(dicyclohexylphosphino)-3,6-dimethoxy-2',4',6'-tri-i-propyl-1,1'-biphenyl (BrettPhos) and many others that those versed in synthetic chemistry are familiar with (see Surry, D. S. et al., XXXVII.

Chem. Sci., 2:27-50 (2011)). A variety of bases can be employed (such as potassium carbonate, sodium tert-butoxide, cesium carbonate and the like) as well as a number of solvents (such as 1,4-dioxane, toluene and dimethylacetamide and the like). Alternatively a 6-amino-nicotinamide (IV) can be coupled with a carboxylate derivative (V) or isocyanate (VI) to make I (Scheme 2). The coupling of IV to V to produce I can be accomplished by many of the myriad ways known to prepare carboxamides. For example, condensation of acid (V, X=OH) with amine (IV) may be effected by treatment of V with an activating reagent, such as a water-soluble carbodiimide (EDC), in the presence of an N-hydroxy triazole (HOAt or HOBt, or the like) and amine (IV) in the presence of base (preferably triethylamine, diisopropylethylamine, or the like) in an appropriate polar aprotic solvent (N,N-dimethylformamide, acetonitrile, dichloromethane, or the like). Alternative combination reagents, reagents that combine an activating reagent and a hydroxy triazole, such as 0-(7-azabenzotriazol-1-yl)-N,N,N',N'-tetramethyluronium hexafluorophosphate (HATU) or (benxotriazol-1-yloxy)tris(dimethylamino)phosphonium hexafluorophosphate (BOP) can be used in the presence of a base. Alternatively, condensation of the acyl halide (V, X=F, Cl) or isocyanate (VI) with the amine IV (typically carried out in the presence of a base such as pyridine or triethylamine in an aprotic solvent) may then provide the desired product I.

Scheme 2. Coupling of amino-nicotinamide IV with V/VI

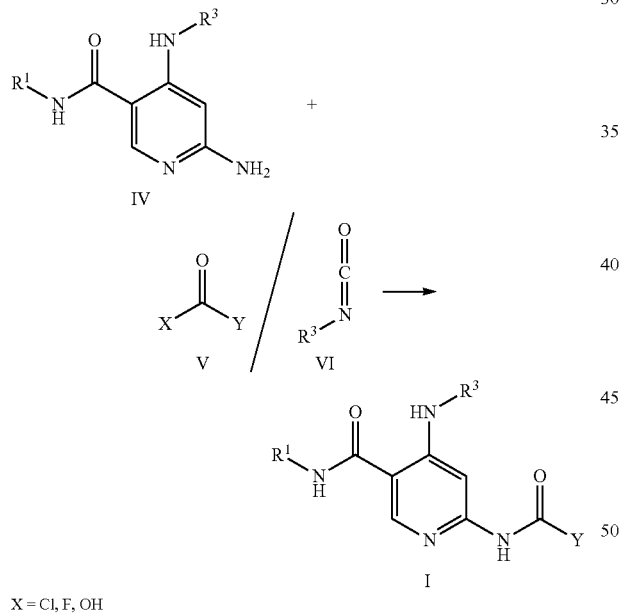

X = Cl, F, OH

Scheme 3. Coupling of halo-pyridine II with VII

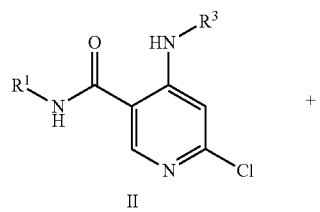

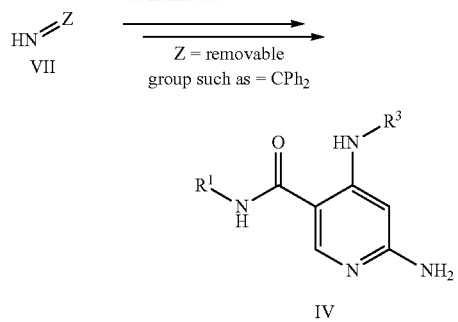

Scheme 3 illustrates the synthesis of 6-amino-nicotinamide IV. Traditionally this is accomplished using a two step procedure, whereby an ammonia equivalent is coupled with the chloride and then in a separate step the protecting or activating group is removed to reveal the primary amine, although new direct couplings of ammonia are being developed (see for example: Lundgren, R. J. et al., Angew. Chem. Int. Ed., 49:4071-4074 (2010)). A variety of multi-step strategies to install an —$NH_2$ group are known although most employ palladium-catalyzed cross-coupling and a protected amine. These conditions often employ groups such as benzophenone imine as the ammonia source (see: Wolfe, J. P. et al., Tetrahedron Lett., 38:6367-6370 (1997)) although numerous other amines can be used including 4-methoxybenzylamine (coupled in a manner analogous to Scheme 1 and removed in the presence of a protic acid in a polar solvent).

Scheme 4. Coupling of halo-pyridine VIII with amine IX

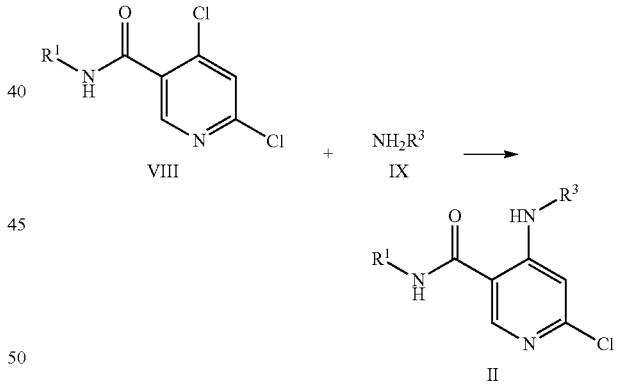

Scheme 4 illustrates the selective displacement of the 4-chloro group of VIII by amine IX to provide intermediate II. Displacement of the dihalide is most often accomplished in the presence of a base, such as sodium bis(trimethylsilyl)amide or N,N-diisopropylethylamine or related, but is also conceivable that it could be accomplished under elevated thermal conditions in the absence of a catalyst, or in the presence of an acid catalyst. In all cases a number of solvents were suitable, including tetrahydrofuran, dimethylformamide and N-methyl-2-pyrrolidone. Due to the increased reactivity of the 4-position relative to the 6-position of the 4,6-dichloronicotinamide it is reasonable to assume that alternative strategies could also be envisioned by someone skilled in the art of chemical synthesis.

Scheme 5. Coupling of carboxylic acid X with amine XI

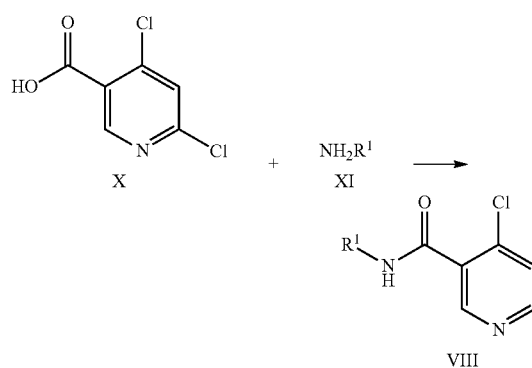

Scheme 5 illustrates the preparation of intermediate VIII from commercially available (or prepared from diethyl 1,3-acetonedicarboxylate following: Platts, M. Y. et al., Tetrahedron Lett., 52:512-514 (2011)) carboxylic acid X. The amides VIII may be prepared from X by many of the myriad ways known to prepare carboxamides by the dehydrative condensation of carboxylic acids and amines. For example, condensation of acid X with amine ($NH_2R_1$, XI, where for these purposes $R_1$ is limited to $CH_3$, $CD_3$, $CH_2CH_3$, and $CD_2CD_3$) may be effected by treatment of X with an activating reagent, such as a water-soluble carbodiimide (EDC), in the presence of an N-hydroxy triazole (HOAt or HOBt, or the like) and amine in the presence of base (preferably triethylamine, diisopropylethylamine, or the like) in an appropriate polar aprotic solvent (N,N-dimethylformamide, acetonitrile, dichloromethane, or the like). Alternative combination reagents, such as HATU or BOP can be used in the presence of a base. The carboxylic acid X may also be converted to an acid chloride by treatment with an appropriate chlorinating agent (thionyl chloride, oxalyl chloride, or the like). Similarly, X may be converted to an acyl fluoride upon exposure to a fluorinating agent (such as cyanuric fluoride). Condensation of the acyl halide (chloride or fluoride) with the amine XI (typically carried out in the presence of a base such as pyridine or triethylamine in an aprotic solvent) may then provide the amide VIII.

Scheme 6. Oxidation of pendant sulfides XII to sulfones and sulfoxides

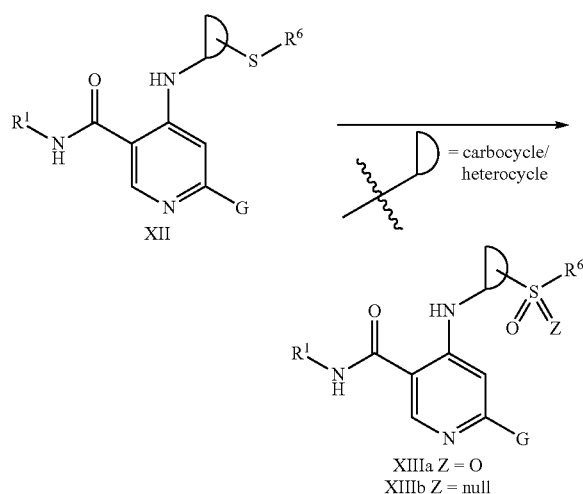

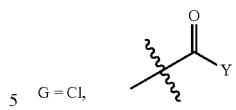

G = Cl, $R^6$ = acyclic aliphatic chains with or without substition, amines bearing aliphatic substituents including hydrogen Scheme 6 illustrates how pendant sulfides can be oxidized to the corresponding sulfones or sulfoxides and, although not illustrated, it is also possible to perform these oxidations on II and then functionalize at the C6 position as shown in Scheme 1. The sulfide (XII) can be oxidized to the sulfone (XIIIa) using an oxidant such as sodium tungstate or 3-chloroperbenzoic acid in an organic solvent such as dichloromethane or acetic acid. The partial oxidation to the sulfoxides (XIIIb) generally requires more mild conditions such as hydrogen peroxide in acetic acid; however, it's possible to use the same conditions as when targeting the sulfone if one quenches the reaction at the appropriate time.

Scheme 7. Synthesis of anilines IX

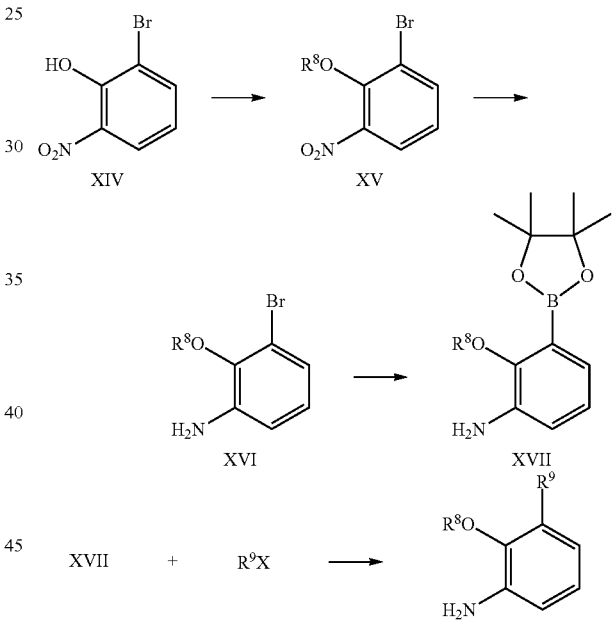

$R^8 = C_nR^{1a}$
$R^9$ = Aryl or heteraryl ring or bicycle
X = halide

A large number of the anilines that were employed in Scheme 4 were commercially available; however, some were not. A strategy for the synthesis of many non-commercially available anilines is described in Scheme 7. The commercially available XIV can be converted to the ether XV using the Williamson ether synthesis. The Williamson ether formation is a common protocol for the synthesis of ethers, the reaction consists of the combination of an alcohol and a base, such as potassium carbonate, sodium hydride, triethylamine, or any number of others, followed by the addition of a compatible electrophile, such as an aliphatic, benzylic or allylic functional group featuring a leaving group, most commonly a halide, but mesylates/tosylates and other groups are also compatible, is added. The reaction is typically run in a polar aprotic solvent such as tetrahydrofuran or dimethylformamide. The nitro group of XI is then reduced to the amine (XVI) using a heterogeneous catalyst such as palladium, zinc or iron and a hydrogen source such as hydrogen (gas), ammonium chloride or hydrochloric acid, such reactions are typically run in alcoholic solvents. Borylation of the aryl bromide can be accomplished using palladium catalysis (see Ishiyama, T. et al., *J. Org. Chem.*, 60:7508 (1995)); however, metal halogen exchange followed by reaction with electrophilic borane is another common approach. The boronic ester (XVII) can be coupled via the Suzuki coupling to a wide variety of aryl and heteroaryl halides using a number of different catalysts, ligands, bases and solvents. One common combination of reagents is 1,1'-bis(di-tert-butylphosphino)ferrocene palladium dichloride, as the catalyst, tribasic potassium phosphate (in water), as the base, reacting with an aryl bromide using dioxane as the solvent; however, a great number of potential combinations exist, for a partial description see: Barder, T. E. et al., *J. Am. Chem. Soc.*, 127:4685-4696 (2005); and Miyaura, N. et al., *Chem. Rev.*, 95:2457-2483 (1995).

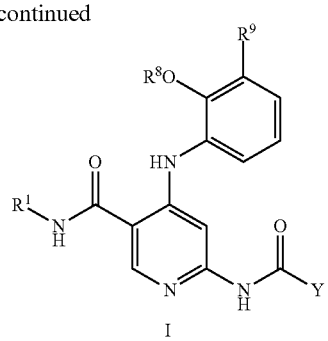

Scheme 8 illustrates a means by which diversity at the $R^9$ (I) can be introduced at the end of the synthetic sequence. In this strategy VIII and XVI can be coupled following the same procedures described in Scheme 4. Intermediate XVIII can be converted to the primary amine via the addition of a protected amine (either via thermal, or selective palladium catalyzed N-arylation conditions) followed by deprotection, for example 4-methoxyphenyl)methanamine can be introduced under strictly thermal conditions followed by deprotection with a protic acid (such as trifluoroacetic acid) to provide XIX. Addition of V/VI to the free amine can be accomplished using the same techniques described in Scheme 2. Conversion to I can be accomplished using the Suzuki coupling reaction as described in Scheme 7, as well as other cross-coupling strategies such as Stille and Negishi cross-couplings (see: Stanforth, S. P., *Tetrahedron.*, 54:263-303 (1998)).

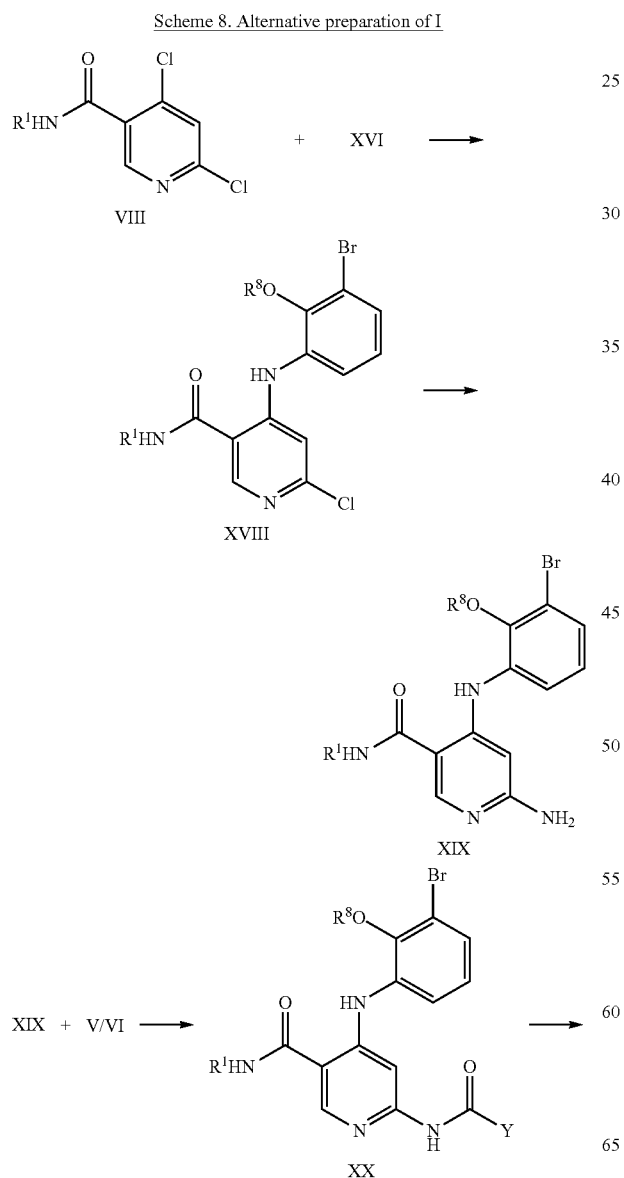

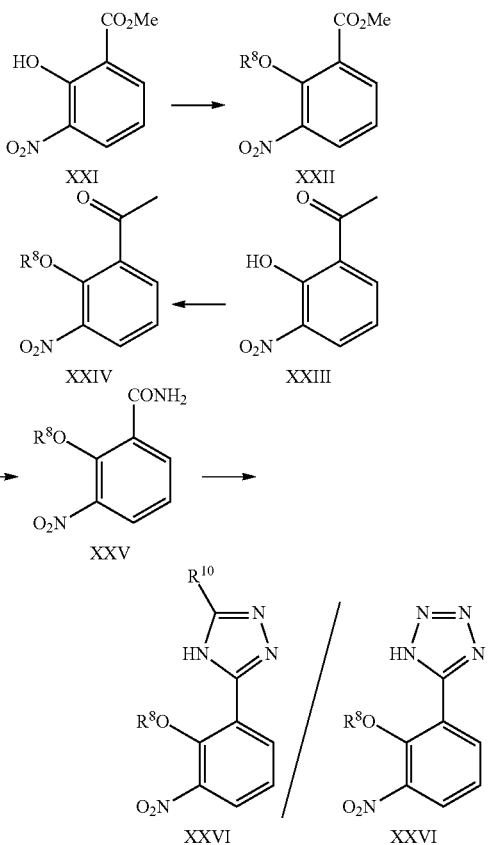

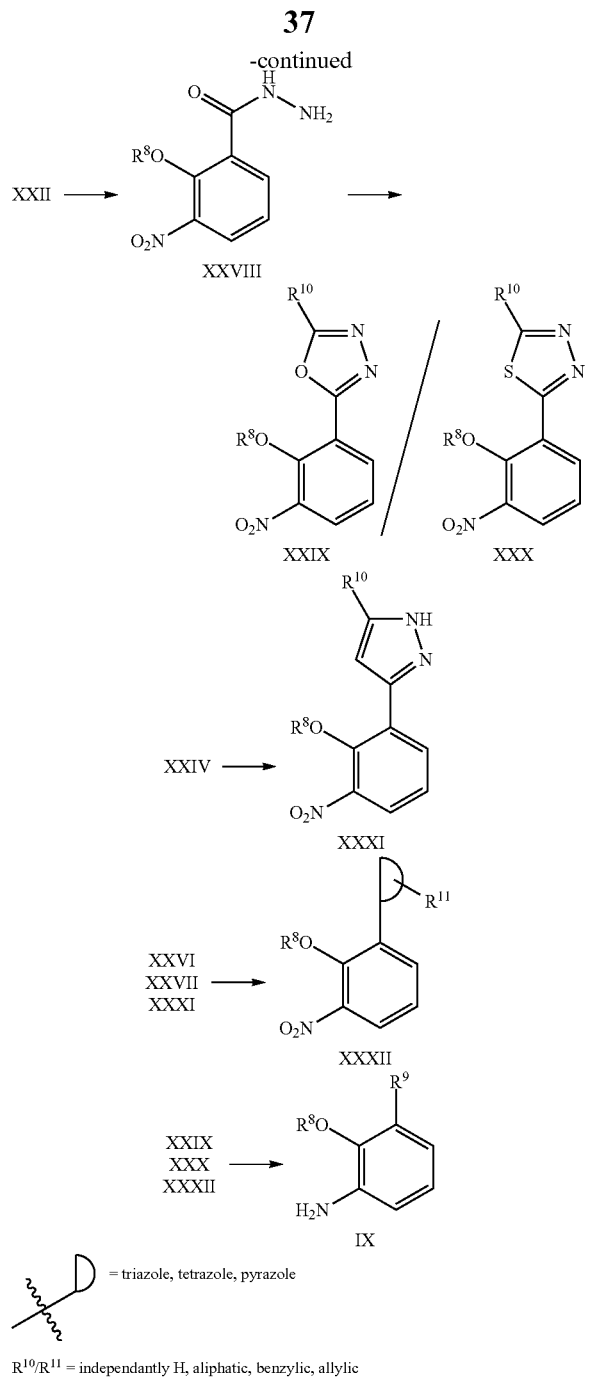

R<sup>10</sup>/R<sup>11</sup> = independantly H, aliphatic, benzylic, allylic

Scheme 9 illustrates how some of heterocycles can be built directly off of carbonyl functionality to arrive at anilines IX without the use of a transition metal catalyzed coupling reaction. The commercially available XXI can be converted to the ether XXII via the techniques described in Scheme 7, similarly XXIII can be converted to XXIV. XXII can be converted to the amide XXV directly using ammonia and ammonium hydroxide in methanol, or via saponification, accomplished using an aqueous base with a polar organic co-solvent like tetrahydrofuran and an alcohol co-solvent like methanol, and amide formation (described in Scheme 5). The amide XXV can be converted to a triazole via formation of the amidine using reagents such as N,N-dimethylacetamide dimethyl acetal or N,N-dimethylformamide dimethyl acetal followed by exposure to hydrazine in the presence of acetic acid. Alternatively the tetrazole XXVII can be prepared from XXV by reaction with triazidochlorosilane (generated in situ from tetrachlorosilane and sodium azide, see: El-Ahl, A-A. S. et al., *Tetrahedron Lett.*, 38:1257-1260 (1997)). The hydrazide XXVIII can be converted to the oxadiazole via a condensation reaction with an orthoformate or orthoacetate under thermal or acid catalyzed conditions, often using the orthoformate/orthoacetate as the solvent. Alternatively the aceto variant of hydrazide XXVIII can be converted to the thiazole by exposure to a sulfonating reagent such as Lawesson's reagent and then condensation under thermal conditions, typically in polar aprotic solvent such as dioxane. The ketone XXIV can be converted to the pyrazole XXXI by condensation with N,N-dimethylacetamide dimethyl acetal or N,N-dimethylformamide dimethyl acetal (or related) followed by reaction with hydrazine in the presence of acetic acid. In the cases of XXVI, XXVII, and XXXI the heterocycle can further be reacted with an electrophile such as organo-halides, epoxides or activated carbonyl species (under basic conditions using an inorganic base such as potassium carbonate, a tertiary amine such as triethylamine, or a strong base such as sodium hydride) or with vinyl ethers such as ethoxyethene (under acidic conditions). Other electrophiles such as silyl halides would also be successful as would potentially a selective palladium catalyzed N-arylation. Finally the nitro compounds can be converted to the aniline IX via reduction using conditions similar to those described in Scheme 7. This list is far from an exhaustive collection of the heterocycles available from common functional group manipulations of carbonyl moieties and their derivatives (such as cyanides) see: Caron, S., *Practical Synthetic Organic Chemistry*, 609-647 (2011) and references therein.

Scheme 10. Synthesis of thioanilines XXXVI

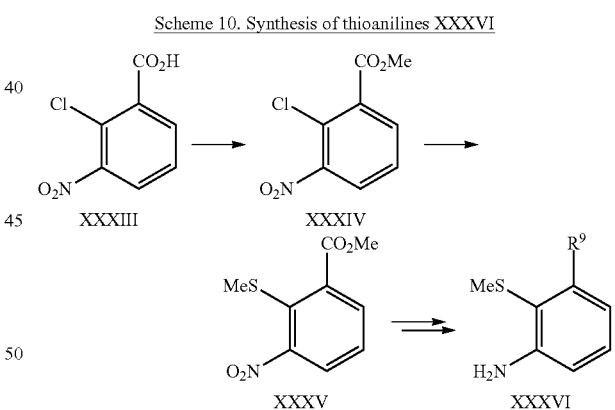

Scheme 10 illustrates the synthesis of the thio-variant of IX. Starting from the commercially available acid XXXIII, which can be converted to the ester via heating with methanol in the presence of a protic acid, as well as by any number of techniques available for the synthesis of esters from acids, such as formation of the acid halide (described in Scheme 5) followed by reaction with methanol. Displacement of the chloride to provide XXXV can be accomplished via nucleophilic addition using sodium thiomethoxide. Conversion to the functionalized aniline XXXVI follows the same techniques illustrated and described in Scheme 9. Additionally the final sulfide product can be oxidized to the sulfone using the oxidation conditions described in Scheme 6.

Scheme 11. Synthesis of final compounds XLII

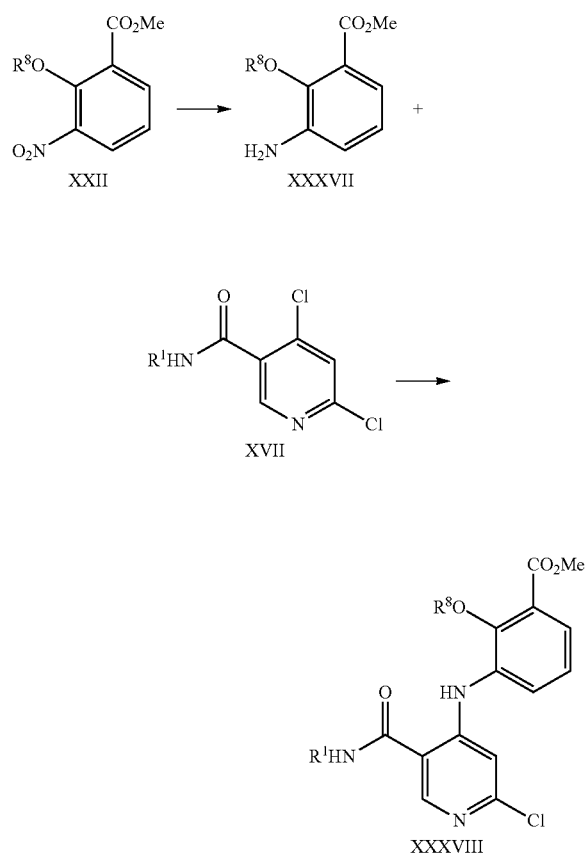

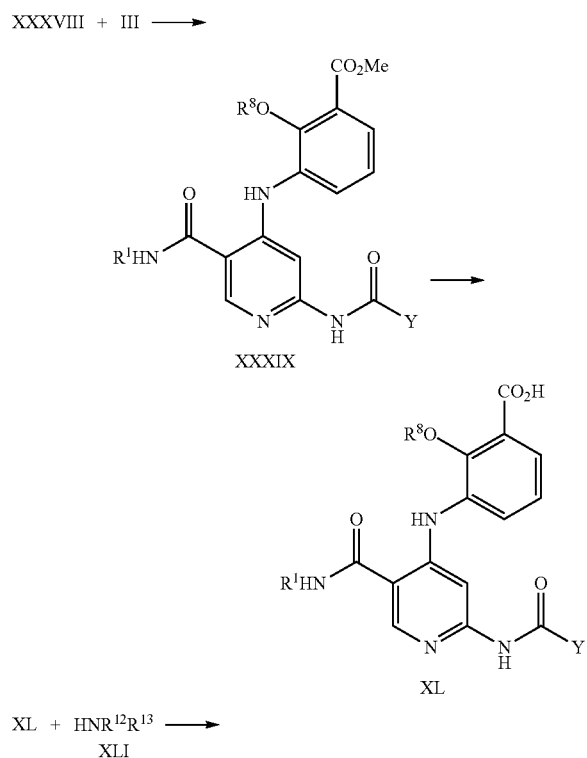

$R^{12}/R^{13}$ = independantly H, aliphatic, benzylic, allylic, also potentially linked to form a heterocycle Scheme 11 illustrates another form of the final compound I. In this strategy the aniline XXXVII (made via reduction of the nitro compound XXII by analogy to Scheme 7) is added to the dichloride VIII using the techniques from Scheme 4. Conversion to XXXIX can be accomplished using the same techniques described in Scheme 1. Saponification of the methyl ester (XXXIX) to provide the acid XL is typically accomplished under aqueous conditions employing a strong water soluble base such as potassium-, lithium-, or sodium hydroxide using tetrahydrofuran and an alcohol co-solvent. The acid XL can be converted to various heterocycles using the techniques described in Scheme 9, or it can be coupled with an amine to generate the amide XLII as the final product as described in Scheme 5.

Scheme 12. Synthesis of anilines XLV (variant of IX)

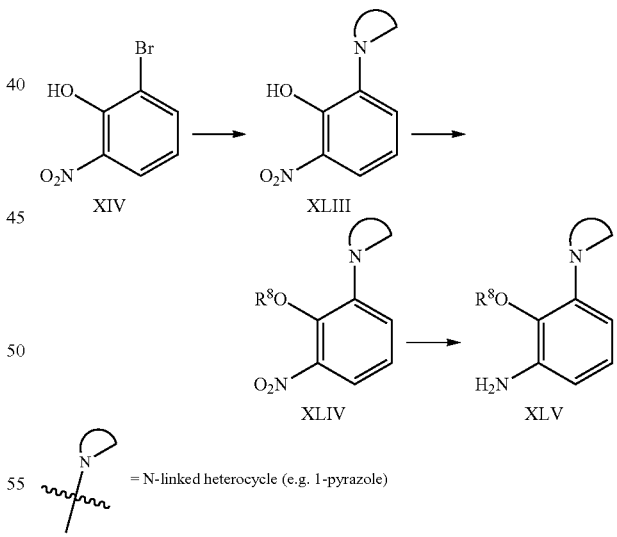

= N-linked heterocycle (e.g. 1-pyrazole)

Scheme 12 illustrates another variant of IX, where the aniline has been substituted with a heterocycle via a carbon-nitrogen bond. Starting from commercially available XIV an Ullmann condensation (for a recent review see: Mannier, F. et al., *Angew. Chem. Int. Ed.*, 48:6954-6971 (2009)) can be used. This reaction is typically performed in the presence of a copper salt (such as copper(I) oxide), an inorganic base (such as cesium carbonate) and often a ligand (although some solvents such as DMF can take the role of the ligand).

The phenol XLIII can be converted to the ether XLIV using the Williamson ether conditions as described in Scheme 7. Conversion to the aniline (XLV) is accomplished by reduction of the nitro group as described in Scheme 7.

dition is performed with a removable group such as methyl pivalate this can be removed and the triazole alkylated as described in Scheme 9. Otherwise the nitro group can be reduced as described in Scheme 7 and XLIX can be carried forward to react with VIII as described in Scheme 4.

Scheme 13. Synthesis of anilines XLVI and XLIX (variants of IX)

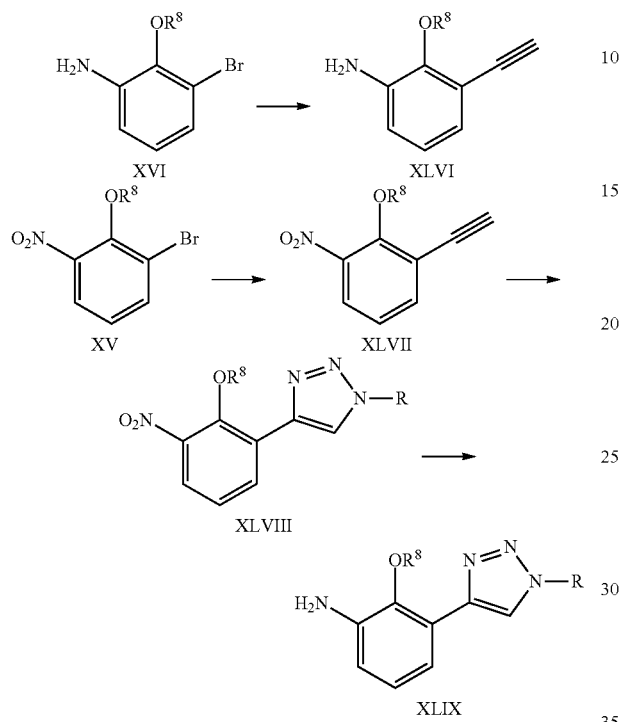

Scheme 14. Synthesis of LII

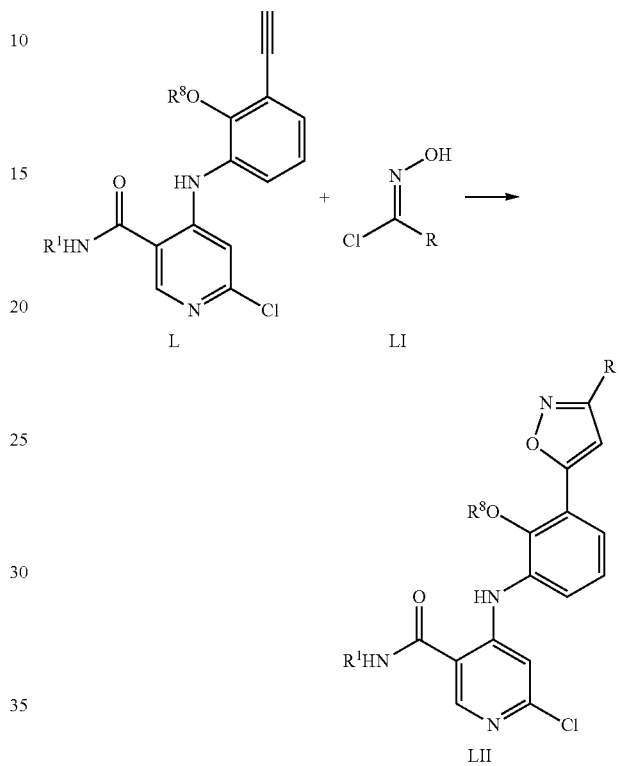

Scheme 13 describes the synthesis of anilines XLVI and XLIX. A Sonogashira coupling of XXVIII/XV with ethynyltrimethylsilane followed by removal of the silyl group using a mild base (such as potassium carbonate in a protic solvent such as methanol) or a fluoride source (such as tetrabutylammonium fluoride or potassium fluoride) can be used to provide the terminal alkynes XLVI and XLVII. The Sonogashira coupling is performed using a palladium catalyst (such as tetrakis triphenylphosphine palladium), a copper catalyst such as copper(I) iodide, and a base (typically an amine base such as triethylamine or diisopropylamine) using either the base as the solvent or a polar solvent such as dimethylformamide; however, a great deal of work has been done running the reaction with different ligands and additives and even in the absence of the catalysts, see: Chinchilla, R., *Chem. Rev.*, 107:874-923 (2007); Chinchilla, R., *Chem. Soc. Rev.*, 40:5084-5121 (2011). The aniline XLVI can be coupled to VIII as described in Scheme 4 and then converted to the target ligand I as described in Scheme 1 or further elaborated using the techniques described for XLVIII (to follow). XLVII can be converted to the 1,2,3-triazole using the Huisgen cycloaddition (or "Click chemistry"), This reaction is run between an alkyne and an azide using a copper catalyst (commonly copper(II) sulfate), a reducing agent (such as sodium ascorbate), the reaction can be run in a number of solvents/co-solvents including water, tert-butyl alcohol, tetrahydrofuran and toluene. A great deal of work has been done describing the variety and versatility of this cycloaddition, for reviews see: Kolb, H. C. et al., *Angew. Chem. Int. Ed.*, 40:2004-2021 (2001) and Meldal, M. et al., *Chem. Rev.*, 108:2952-3015 (2008). If the Huisgen cycload- Scheme 14 illustrates the synthesis of penultimate compounds LII (converted to target ligands using the coupling procedures described in Scheme 1). Intermediate L (prepared using the techniques described in Scheme 13 and Scheme 4) can be converted to the isoxazole LII using a [3+2] cycloaddition with a nitrile oxide (formed in situ from an N-hydroxyimidoyl chloride and a mild non-nucleophilic base). The reaction can be run thermally in aprotic solvents (such as dichloroethane) but recent work has described the utility of catalysts in the reaction, see: Grecian, S. et al., *Angew. Chem. Int. Ed.*, 47:8285-8287 (2008).

Scheme 15. Synthesis of LVIII

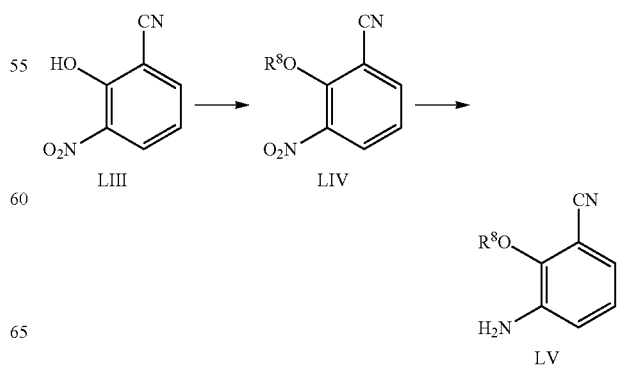

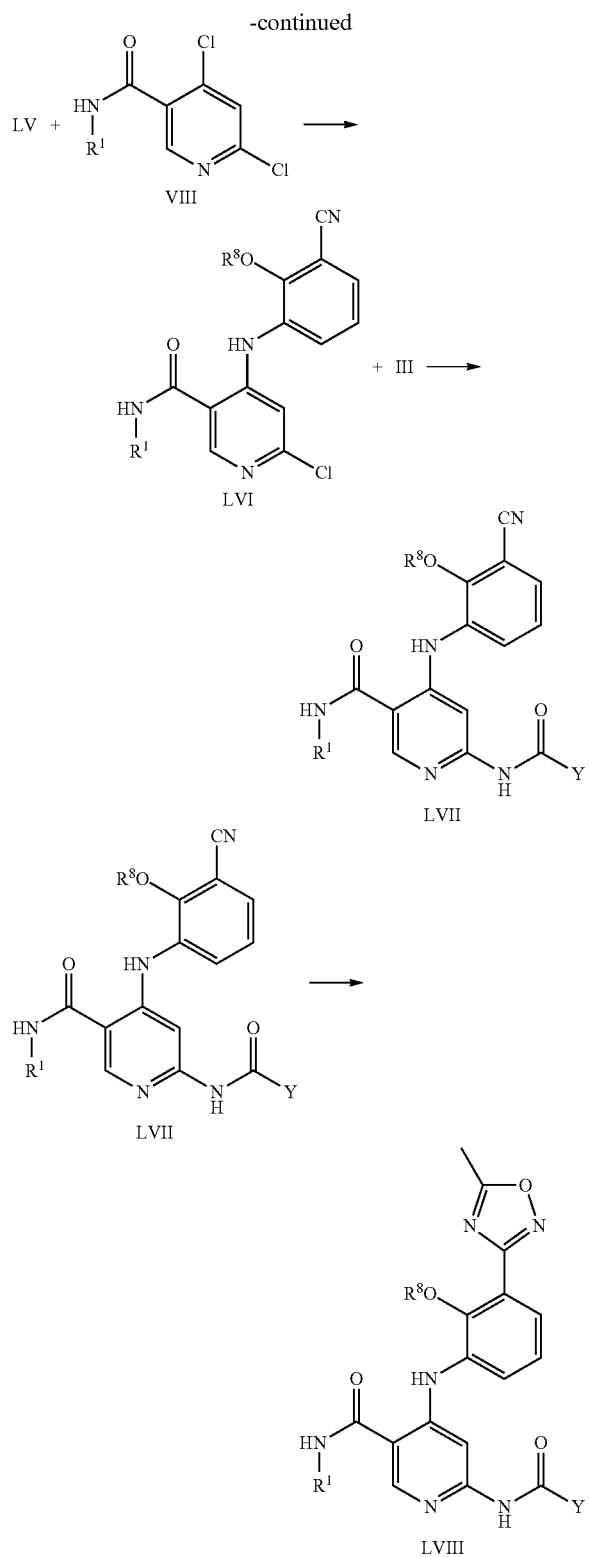

Scheme 15 illustrates the synthesis of target compounds LVII and LVIII. Commercially available LIII can be converted to the aniline LV following the strategies outlined in Scheme 7. Addition of LV to VIII follows the techniques described in Scheme 4 to provide LVI, which can be coupled with III following the strategies described in Scheme 1. Conversion of the cyano-containing LVII to the oxadiazole LVIII can be accomplished via the nucleophilic addition of hydroxylamine to the cyanide, performed under basic conditions typically in a polar protic solvent such as water or alcohol, followed by acylation and condensation with acetic anhydride, done by heating the intermediate with acetic anhydride in a polar aprotic solvent

EXAMPLES

Preparation of compounds of Formula I, and intermediates used in the preparation of compounds of Formula I, can be prepared using procedures shown in the following Examples and related procedures. The methods and conditions used in these examples, and the actual compounds prepared in these Examples, are not meant to be limiting, but are meant to demonstrate how the compounds of Formula I can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Chemical names were determined using ChemDraw Ultra, version 9.0.5 (CambridgeSoft). The following abbreviations are used:

$NaHCO_3$ (aq)=saturated aqueous sodium bicarbonate
brine=saturated aqueous sodium chloride
DCM=dichloromethane
DIEA=N,N-diisopropylethylamine
DMAP=4-(N,N-dimethylamino)pyridine
DMF=N,N-dimethylformamide
DMSO=dimethyl sulfoxide
EDC=N-(3-dimethylaminopropyl)-N'-ethylcarbodiimide hydrochloride
EtOAc=ethyl acetate
HOAT=1-hydroxy-7-azabenzotriazole
HOBT=1-hydroxybenzotriazole hydrate
rt=ambient room temperature (generally about 20-25° C.)
TEA=triethylamine
TFA=trifluoroacetic acid
THF=tetrahydrofuran Preparations The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:

Method A (Used in all Cases, Unless Otherwise Indicated):
Linear gradient of 0 to 100% solvent B over 4 minutes ("min"), with 1 minute ("min") hold at 100% B.
Ultraviolet ("UV") visualization at 220 nanometers ("nm")
Column: YMC S5 ODS Ballistic 4.6×50 mm
Flow rate: 4 milliliters ("mL")/min
Solvent A: 0.2% phosphoric acid, 90% water, 10% methanol
Solvent B: 0.2% phosphoric acid, 90% methanol, 10% water Method B:
Column: PHENOMENEX® Luna C18(2), 4.6×50 mm×5 μm
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)
Detector 3: ELSD Method C:
Column: Waters SunFire C18, 4.6×50 mm×5 μm
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)
Detector 3: ELSD Method D:
Column: PHENOMENEX® Luna C18(2), 4.6×50 mm×5 μm
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)
Detector 3: ELSD Method E:
Column: Waters Acquity UPLC BEH C18, 2.1×50 mm, 1.7 μm particles
Mobile Phase: (A) 5:95 acetonitrile:water; (B) 95:5 acetonitrile:water
Buffer: 10 mM ammonium acetate
Gradient Range: 0-100% B
Gradient Time: 3 min
Flow Rate: 1.11 mL/min
Analysis Time: 4 min
Detection:
Detector 1: UV at 220 nm
Detector 2: MS(ESI$^+$)
Detector 3: ELSD Method F:
Column: Waters SunFire C18 (4.6×150 mm), 3.5 μm
Mobile Phase: (A) 5:95 acetonitrile:water; (B) 95:5 acetonitrile:water
Buffer: 0.1% TFA
Gradient Range: 0-100% B
Gradient Time: 12 min
Flow Rate: 4 mL/min
Analysis Time: 15 min
Detection:
Detector 1: UV at 220 nm
Detector 2: UV at 254 nm Method G:
Column: Waters Acquity UPLC BEH C18, 2.1×50 mm, 1.7 μm particles
Mobile Phase: (A) 5:95 acetonitrile:water; (B) 95:5 acetonitrile:water
Buffer: 0.05% TFA
Gradient Range: 0-100% B
Gradient Time: 3 min
Flow Rate: 1.11 mL/min
Analysis Time: 4 min
Detection:
Detector 1: UV at 220 nm
Detector 2: MS(ESI$^+$)
Detector 3: ELSD Method H:
Column: (LCMS) Ascentis Express C18, 4.6×50 mm, 2.7 μm particles
Mobile Phase: (A) 5:95 acetonitrile:water; (B) 95:5 acetonitrile:water
Buffer: 10 mM ammonium acetate
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)

Method I:
Column: Waters XBridge C18, 4.6×50 mm, 5 μm particles
Mobile Phase: (A) 5:95 acetonitrile:water; (B) 95:5 acetonitrile:water
Buffer: 0.05% TFA
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)

Method J:
Column: (LCMS) BEH C18, 2.1×50 mm, 1.7 μm particles
Mobile Phase: (A) water; (B) acetonitrile
Buffer: 0.05% TFA
Gradient Range: 2%-98% B (0 to 1 min) 98% B (to 1.5 min) 98%-2% B (to 1.6 min)
Gradient Time: 1.6 min
Flow Rate: 0.8 mL/min
Analysis Time: 2.2 min Detection:
  Detector 1: UV at 254 nm
  Detector 2: MS(ESI+)
Method K:
  Column: (LCMS) BEH C18, 3.0×50 mm, 1.7 μm particles
  Mobile Phase: (A) 5:95 acetonitrile:water; (B) 95:5 acetonitrile:water
  Buffer: 10 mM ammonium acetate
  Gradient Range: 0-100% B
  Gradient Time: 1.8 min
  Flow Rate: 1.2 mL/min
  Analysis Time: 4 min
Detection:
  Detector 1: UV at 220 nm
  Detector 2: MS(ESI+)
Method L:
  Column: (LCMS) SunFire C18 2.1×30 mm, 2.5 μm particles
  Mobile Phase: (A) 10:90 methanol:water; (B) 90:10 methanol:water
  Buffer: 0.1% TFA
  Gradient Range: 0-100% B
  Gradient Time: 2 min
  Flow Rate: 1 mL/min
  Analysis Time: 3 min
Detection:
  Detector 1: UV at 220 nm
  Detector 2: MS(ESI+)
Method M:
  Column: (LCMS) SunFire C18 2.1×30 mm, 3.5 μm particles
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 1 mL/min
  Analysis Time: 5 min
Detection:
  Detector 1: UV at 220 nm
  Detector 2: MS(ESI+)
Method N:
  Column: YMC ProC18 ODS, 4.6×50 mm
  Mobile Phase: (A) 10:90 MeOH:water; (B) 90:10 MeOH:water
  Buffer: 0.2% $H_3PO_4$
  Gradient Range: 0-100% B
  Gradient Time: 4 min
  Flow Rate: 4 mL/min
  Analysis Time: 4 min
  Detection: 220 nm Preparation 1

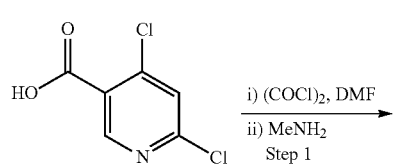

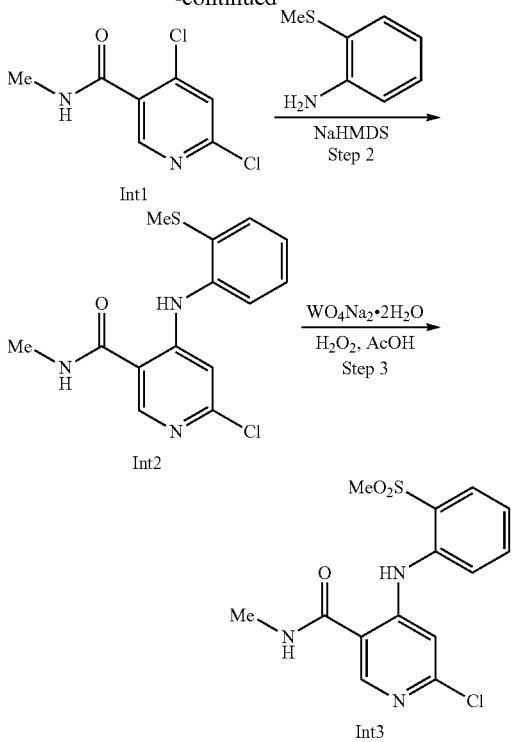

Step 1

To a round bottomed flask containing 4,6-dichloronicotinic acid (60 g, 313 mmol) was added chloroform (500 mL) and a single drop of N,N-dimethylformamide (DMF). The reaction was cooled to 0° C. and oxalyl chloride (82 mL, 938 mmol) was subsequently added over 5 minutes. The reaction was maintained at 0° C. for one hour and then concentrated under reduced pressure. The reaction vessel was recharged with chloroform and reconcentrated, this was repeated one additional time, yielding a brown oil. The oil was dissolved in chloroform (500 mL) and cooled to 0° C. To the chilled reaction vessel was added methylamine (2 M in THF, 390 mL, 780 mmol) in a gradual manner. Stirring was maintained at 0° C. for 1 hour and then the reaction was quenched via the addition of water. The product was extracted with chloroform and the combined organic layers were washed with water and brine (saturated aqueous sodium chloride solution) and then dried over sodium sulfate, filtered and concentrated. The crude product (52 g) was combined with another batch of crude material (27 g) and then purified using flash chromatography eluting with 40-50% ethyl acetate in petroleum ether, providing 73 g of the product Int1. $^1$H NMR (400 MHz, DMSO-$d_6$): δ 8.60 (bm, 1H), δ 8.47 (s, 1H), δ 7.89 (s, 1H), δ 2.78 (d, J=4.6 Hz, 3H). LC retention time 1.25 min [A]. Mass Spectrometry ("MS") (E+) m/z: 205 (MH+).

Step 2

To a solution of Int1 (1.8 g, 8.78 mmol) in tetrahydrofuran (THF, 68 mL) was added 2-(methylthio)aniline (1.83 g, 13.2 mmol) followed by sodium bis(trimethylsilyl)amide solution (NaHMDS, 1M in THF, 61 mL, 61 mmol). The reaction was stirred at room temperature for 30 minutes and then quenched with water. The crude product was extracted with ethyl acetate, dried over sodium sulfate, filtered, concentrated and purified by automated chromatography (0-100% EtOAc/hexanes) to provide Int2 (2.16 g, 80% yield). $^1$H NMR (400 MHz, DMSO-$d_6$) δ 10.34 (s, 1H), 8.77 (d, J=4.4 Hz, 1H), 8.51 (s, 1H), 7.44-7.22 (m, 4H), 6.51 (s, 1H), 2.80 (d, J=4.6 Hz, 3H), 2.43 (s, 3H). LC retention time 0.86 min [J]. MS (E+) m/z: 308 (MH+).

Step 3

Int2 (900 mg, 2.92 mmol) was suspended in acetic acid (AcOH, 9.7 mL), and hydrogen peroxide (30% aqueous solution, 6.0 mL, 58.5 mmol) and sodium tungstate dihydrate (964 mg, 2.92 mmol) were subsequently added. The reaction was complete after 30 minutes, and was then diluted with water and ethyl acetate. The layers were separated and the aqueous layer extracted once with ethyl acetate. The combined organic layers were washed once with saturated aqueous sodium bisulfite and once with water. The combined organic layers were then dried over sodium sulfate, filtered, concentrated under reduced pressure and purified with automated silica gel chromatography (0-100% EtOAc/hexanes), yielding the sulfone product Int3. $^1$H NMR (400 MHz, DMSO-$d_6$) δ 10.76 (s, 1H), 8.79 (d, J=4.0 Hz, 1H), 8.57 (s, 1H), 7.96 (dd, J=7.9, 1.5 Hz, 1H), 7.79-7.73 (m, 1H), 7.70-7.66 (m, 1H), 7.46 (t, J=7.6 Hz, 1H), 6.97 (s, 1H), 3.17 (s, 3H), 2.79 (d, J=4.4 Hz, 3H). LC retention time 0.72 min [J]. MS (E+) m/z: 339 (MH+).

Example 1

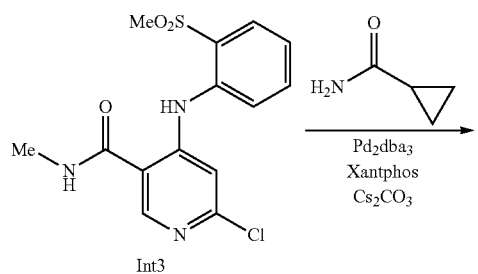

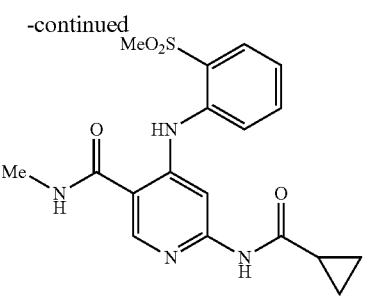

Cyclopropanecarboxamide (22.5 mg, 0.26 mmol) was combined with Int3 (30 mg, 0.088 mmol). To the vessel was added dimethylacetamide (DMA, 0.6 mL) followed by tris(dibenzylideneacetone)dipalladium(0) (Pd$_2$dba$_3$, 8.1 mg, 0.0088 mmol), 4,5-bis(diphenylphosphino)-9,9-dimethylxanthene (Xantphos, 10 mg, 0.018 mmol) and cesium carbonate (115 mg, 0.35 mmol). The vessel was then evacuated and backfilled with nitrogen three times and then heated to 145° C. for 1 hour. The reaction was cooled to room temperature and then diluted with ethyl acetate (EtOAc, ~250 mL). The solution was washed twice with water, dried over sodium sulfate (Na$_2$SO$_4$) filtered, concentrated and purified using preparative HPLC. The product was collected as the TFA salt and then dissolved in ~15 mL water, to this was added c. 100 mL of saturated sodium bicarbonate (NaHCO$_3$, aqueous solution) and stirred for 10 minutes. The product was extracted (×3) from the slurry using dichloromethane (DCM), dried over sodium sulfate, filtered concentrated and collected to give 16.3 mg of 1 (48% yield). $^1$H NMR (500 MHz, methanol-$d_4$) δ 8.42 (s, 1H), 8.12 (dd, J=7.9, 1.5 Hz, 1H), 7.80 (td, J=7.7, 1.5 Hz, 1H), 7.67 (d, J=7.4 Hz, 1H), 7.53 (t, J=7.7 Hz, 1H), 7.30 (s, 1H), 3.16 (s, 3H), 2.96 (s, 3H), 1.84-1.70 (m, 1H), 1.10-1.05 (m, 2H), 0.98 (dq, J=7.4, 4.0 Hz, 2H). LC retention time 1.11 min [E]. MS (E+) m/z: 389 (MH+).

The following Examples were prepared in a similar manner to the product of Example 1

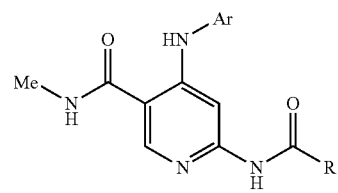

| Example No. | Ar | R | Rt (min) [Method] | m/z [M + H]+ |
|---|---|---|---|---|
| 2 | 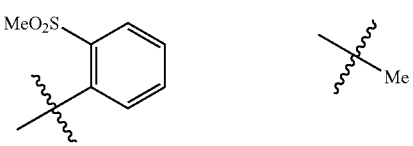 | | 1.03 [E] | 363 |
| 3 | 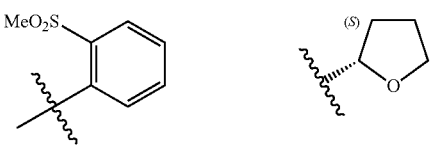 | | 1.17 [E] | 419 |

-continued

| Example No. | Ar | R | Rt (min) [Method] | m/z [M + H]+ |
|---|---|---|---|---|
| 4 | 2-(MeO₂S)-phenyl | tetrahydropyran-4-yl | 1.11 [E] | 433 |
| 5 | 2-(MeO₂S)-phenyl | cyclohexyl | 1.54 [E] | 431 |
| 6 | 2-(MeO₂S)-phenyl | CH₂Ph | 1.43 [E] | 439 |
| 7 | 2-(MeO₂S)-phenyl | CH(Me)Me | 1.24 [E] | 391 |
| 8 | 2-(MeO₂S)-phenyl | (S)-2,2-dimethylcyclopropyl | 1.44 [E] | 417 |
| 9 | 2-(MeO₂S)-phenyl | 1,2,3,4-tetrahydronaphthalen-1-yl (racemic) | 1.65 [E] | 479 |
| 10 | 2-(MeO₂S)-phenyl | CH₂-(pyridin-2-yl) | 1.15 [E] | 440 |
| 11 | 2-(MeO₂S)-phenyl | n-propyl (CH₂CH₂CH₃) | 1.24 [E] | 391 |
| 12 | 2-(MeO₂S)-phenyl | CH₂-(4-methoxyphenyl) | 1.41 [E] | 469 |

-continued

| Example No. | Ar | R | Rt (min) [Method] | m/z [M + H]⁺ |
|---|---|---|---|---|
| 13 | 2-(MeO₂S)phenyl | CH(Et)₂ | 1.45 [E] | 403 |
| 14 | 2-(MeO₂S)phenyl | cyclobutyl | 1.30 [E] | 403 |
| 15 | 2-(MeO₂S)-4-F-phenyl | cyclopropyl | 1.26 [E] | 407 |
| 16 | 2-(MeO₂S)phenyl | NH-Et | 1.06 [E] | 392 |
| 17 | 2-(MeO₂S)phenyl | NH-Me | 0.97 [E] | 378 |
| 18 | 2-(MeO₂S)-3-F-phenyl | cyclopropyl | 1.11 [E] | 407 |
| 19 | 2-(HO-C(Me)₂)phenyl | cyclopropyl | 1.25 [E] | 369 |
| 20 | 2-(MeO₂S)-5-F-phenyl | cyclopropyl | 1.19 [E] | 407 |

-continued

| Example No. | Ar | R | Rt (min) [Method] | m/z [M + H]+ |
|---|---|---|---|---|
| 21 | MeO2S-phenyl | cyclopropyl-F,F | 1.79 [E] | 425 |
| 22 | MeO2S-phenyl | cyclopropyl-F (±) | 1.15 [E] | 407 |

Preparation 2

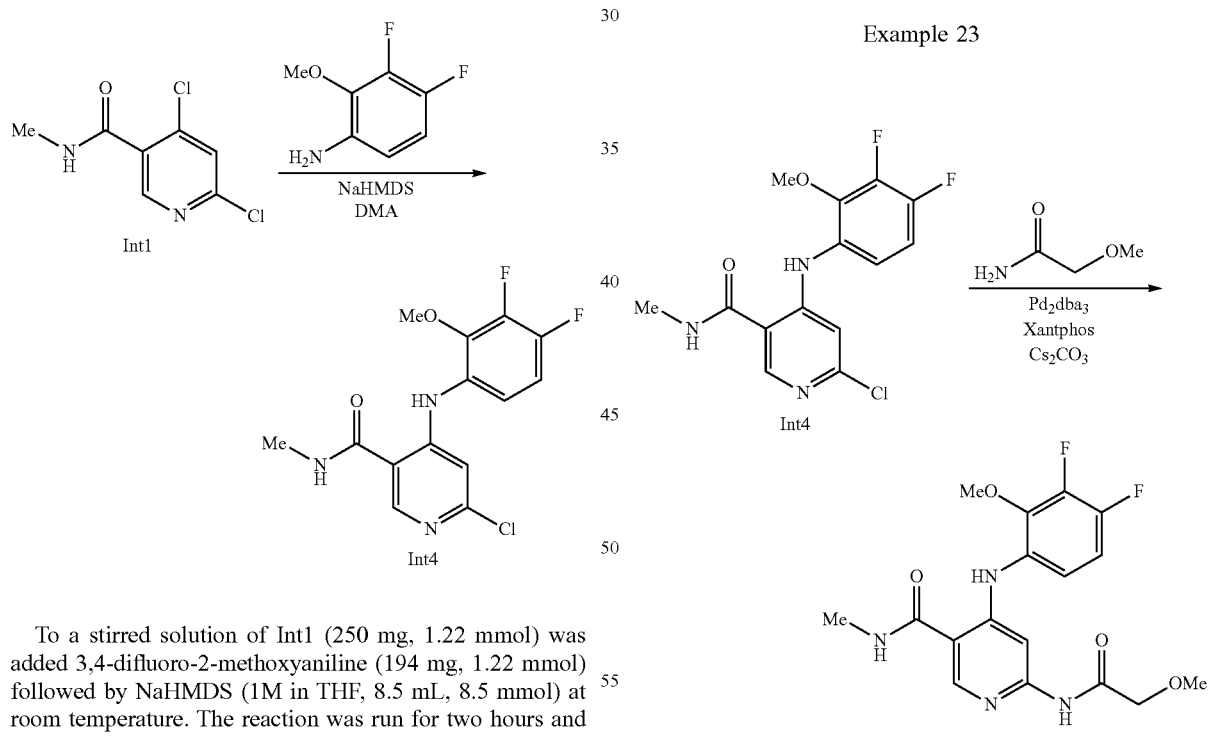

To a stirred solution of Int1 (250 mg, 1.22 mmol) was added 3,4-difluoro-2-methoxyaniline (194 mg, 1.22 mmol) followed by NaHMDS (1M in THF, 8.5 mL, 8.5 mmol) at room temperature. The reaction was run for two hours and then aqueous 1N HCl was added to adjust the pH to ~5. The slurry was filtered off and washed with water, the residual solid was collected as pure product. The filtrate was extracted with DCM, washed 3× with water, dried over sodium sulfate, filtered, concentrated and purified by automated chromatography (0%-100% EtOAc/hexanes). The pure fractions were combined with the solid collected during filtration to provide Int4 (400 mg, 100% yield). $^1$H NMR (400 MHz, chloroform-d) δ 10.05 (br. s., 1H), 8.34 (s, 1H), 7.02 (ddd, J=9.0, 5.2, 2.1 Hz, 1H), 6.97-6.87 (m, 1H), 6.78 (s, 1H), 6.38 (br. s., 1H), 4.00 (d, J=2.2 Hz, 3H), 3.04 (d, J=4.8 Hz, 3H). LC retention time 0.90 min [J]. MS (E+) m/z: 328 (MH$^+$).

Example 23

2-Methoxyacetamide (37 mg, 0.42 mmol) was combined with Int4 (100 mg, 0.305 mmol). To the vessel was added dimethylacetamide (1 mL) followed by Pd$_2$dba$_3$ (27 mg, 0.030 mmol), Xantphos (35 mg, 0.061 mmol) and cesium carbonate (297 mg, 0.92 mmol). The vessel was then evacuated and backfilled with nitrogen three times and then heated to 145° C. for 2 hours. The crude product was diluted with DMF and filtered, before being purified using preparative HPLC providing 28 mg (24% yield) of 23. $^1$H NMR (400

MHz, DMSO-d$_6$) δ 10.52 (s, 1H), 9.93 (s, 1H), 8.63 (m, 1H), 8.51 (s, 1H), 7.81 (s, 1H), 7.23 (m, 2H), 4.01 (s, 2H), 3.89 (s, 3H), 2.79 (d, J=4.8 Hz, 3H). LC retention time 6.14 min [F]. MS (E+) m/z: 381 (MH+).

The following Examples were prepared in a similar manner to the product of Example 23

2-Cyanoacetamide (11 mg, 0.13 mmol) was combined with Int3 (30 mg, 0.088 mmol). To the vessel was added dimethylacetamide (DMA, 0.6 mL) followed by tris(dibenzylideneacetone)dipalladium(0) (Pd$_2$dba$_3$, 8.1 mg, 0.0088 mmol), 4,5-bis(diphenylphosphino)-9,9-dimethylxanthene (Xantphos, 10 mg, 0.018 mmol) and cesium carbonate (58

| Example No. | Ar | R | Rt (min) [Method] | m/z [M + H]+ |
|---|---|---|---|---|
| 24 | MeO, F, F phenyl | t-Bu (Me$_3$C) | 5.47 [F] | 351 |
| 25 | MeO, F, F phenyl | cyclopropyl | 6.39 [F] | 377 |
| 26 | MeO, Cl phenyl | 2-aminopyridin-4-yl | 1.40 [E] | 427 |

Preparation 3

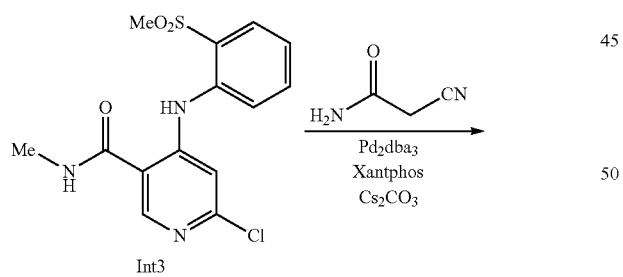

mg, 0.18 mmol). The vessel was then evacuated and back-filled with nitrogen three times and then heated to 145° C. for 1 hour. The intended product was not formed; however, Int5 was observed by LCMS and was subsequently collected by cooling the reaction mixture to room temperature, absorbing the crude solution onto silica and purifying by automated chromatography (0-100% MeOH/DCM). LC retention time 0.55 min [J]. MS (E+) m/z: 321 (MH+).

Example 27

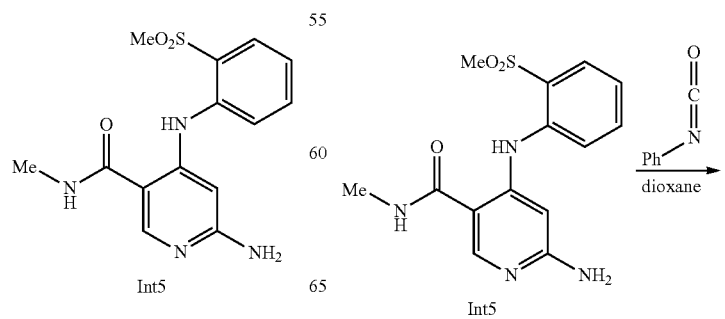

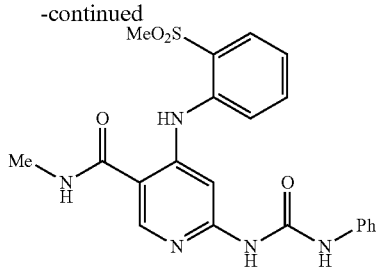

Int5 (40 mg, 0.125 mmol) was combined in 1,4-dioxane (1 mL) with isocyanatobenzene (15 mg, 0.125 mmol) and the reaction was stirred overnight. The crude solution was diluted with DMF, filtered and purified using preparative HPLC to provide 27 (15.8 mg, 27%). $^1$H NMR (500 MHz, methanol-$d_4$) δ 8.46 (s, 1H), 8.04 (d, J=7.9 Hz, 1H), 7.71 (d, J=3.5 Hz, 2H), 7.47 (d, J=7.4 Hz, 2H), 7.44-7.40 (m, 1H), 7.35 (dt, J=8.1, 4.1 Hz, 1H), 7.34-7.26 (m, 3H), 7.19 (br. s., 1H), 7.07 (t, J=7.4 Hz, 1H), 3.14 (s, 3H), 2.95 (s, 3H). LC retention time 1.39 min [E]. MS (E+) m/z: 440 (MH$^+$).

Preparation 4

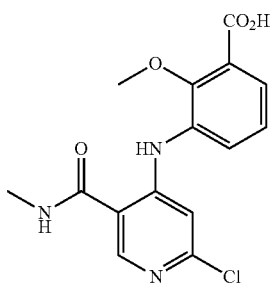 [SMILES: CNC(=O)c1cnc(Cl)cc1Nc1cccc(C(=O)O)c1OC]

Step 1

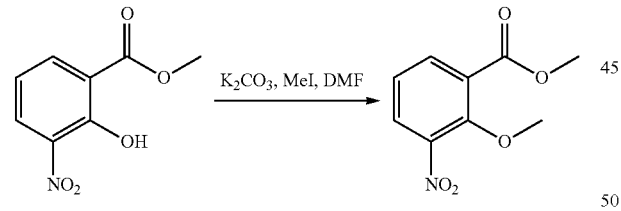

To a solution of methyl 2-hydroxy-3-nitrobenzoate (10 g, 50.7 mmol) in DMF (100 mL) at rt was added potassium carbonate (14.02 g, 101 mmol) followed by addition of methyl iodide (6.34 mL, 101 mmol) and the resulting orange mixture was heated to 60° C. for 1 h. LCMS analysis at this time showed complete and clean conversion to a major product consistent with the expected product (observed MH+ 212). Let cool to rt and added crushed ice (~100 mL) followed by water to a total volume of ~400 mL causing a nice yellow solid to crystallize from solution. Stirred for a few minutes to give a nice slurry then collected solid by vacuum filtration and the resulting initially yellow solid was rinsed with additional water (~100 mL) until all of the yellow color was rinsed into the filtrate giving a near white solid in the funnel. Partially air-dried solid in funnel then transferred to a round bottomed flask and further dried under vacuum overnight to afford 10.5 g (98%) of a yellow solid as methyl 2-hydroxy-3-nitrobenzoate. LCMS MH+ 212.

Step 2

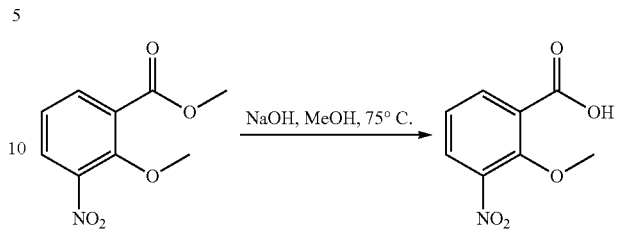

Methyl 2-hydroxy-3-nitrobenzoate (2.85 g, 13.50 mmol) was dissolved in hot methanol (10 mL) at 75° C. to make clear solution and 1N aq. sodium hydroxide (28.3 mL, 28.3 mmol) was added dropwise. The mixture was heated under reflux for 15 min. whereupon HPLC analysis indicated complete conversion to a more polar product. The reaction was cooled to rt, concentrated to remove the methanol and the resulting aqueous solution was cooled in and ice bath and made acidic by a dropwise addition of 1M HCl (40 mL) until the pH was ~1. The resulting precipitated solid was collected by filtration, rinsed with water, and dried on the filter to afford the product 2-methoxy-3-nitrobenzoic acid (2.48 g, 12.58 mmol, 93% yield) as a white solid. HPLC (method N) RT=1.57 min.

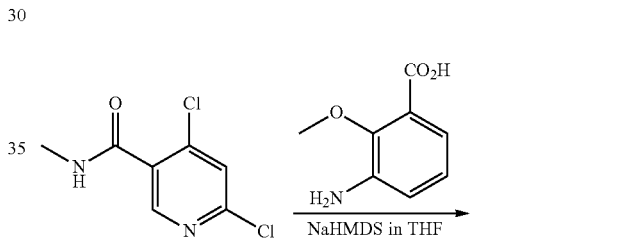

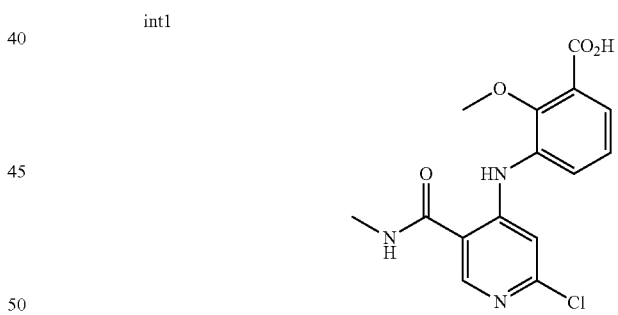

Step 3

Dissolved 4,6-dichloro-N-methylnicotinamide (Int1, 150 mg, 0.732 mmol) and 3-amino-2-methoxybenzoic acid (159 mg, 0.951 mmol) in DMA (2 mL) and added sodium bis(trimethylsilyl)amide (1.0 M in THF) (2.93 mL, 2.93 mmol) dropwise via syringe at rt over ~5 min causing a slight exotherm. Let reaction stir at rt for 30 min then crushed ice was added to quench the reaction. After stirring for ~30 min, the pH of the mixture was adjusted with aq 1N HCl to ~1 and the resulting solid which had precipitated was collected by vacuum filtration, rinsed with water, and dried on the filter to afford Preparation 4, 3-((2-chloro-5-(methylcarbamoyl)pyridin-4-yl)amino)-2-methoxybenzoic acid (156 mg, 0.465 mmol, 63.5% yield), as a tan solid. HPLC RT (method N)=2.57 min. LCMS MH+ 336.1.

Preparation 5

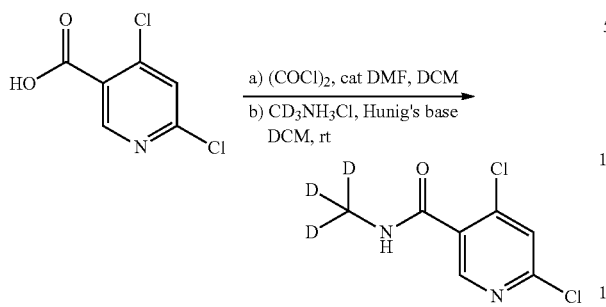

To a slurry of 4,6-dichloronicotinic acid (3 g, 15.63 mmol) in dichloromethane (90 mL) at rt was added oxalyl chloride (1.778 mL, 20.31 mmol) followed by 3 drops of DMF causing some effervescence. Let mixture stir at rt for ~1.5 h at which time mixture became a nearly clear solution. A small aliquot was removed, concentrated to dryness and dissolved in MeOH and was analyzed by LCMS which indicated the complete conversion of the acid starting material to afford the methyl ester indicating complete conversion of the acid to the desired acid chloride had taken place. The reaction was concentrated and the residue was dissolved in dichloroethane (~20 mL) and reconcentrated and the process was repeated to ensure complete removal of the excess oxalyl chloride. The resulting crude acid chloride was dissolved in dichloromethane (~100 mL) and methyl-d3-ammonium chloride (1.433 g, 20.31 mmol) was added and the mixture was cooled in an ice bath whereupon Hunig's base (8.19 mL, 46.9 mmol) was added dropwise via syringe. After the addition was complete, the ice bath was removed and the resulting mixture was allowed to warm to rt and stir. After stirring overnight at rt, LCMS analysis indicated complete and clean conversion to the desired CD3-amide product (observed MH+ 208). The mixture was diluted with dichloromethane (~100 mL) and was washed with 1 N aq HCl (3×100 mL) then brine before drying over anhyd sodium sulfate, decanting and concentrating under vacuum. This afforded 2.7 g of an off-white solid which was purified by preparative silica gel flash chromatography using EtOAc/hexanes as the eluant. Fractions containing the major uv active product were collected and concentrated under vacuum to afford 2.42 g (74%) of a white solid as the pure product (Preparation 5). LCMS MH+ 209.2.

Preparation 6

Step 1

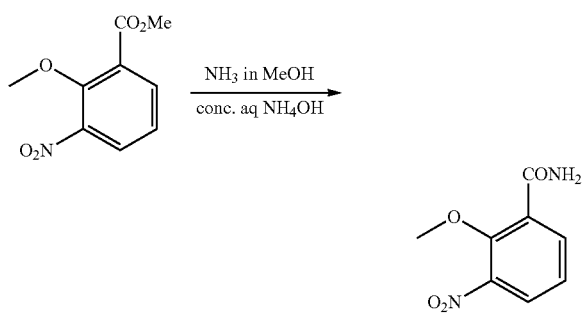

Methyl 2-methoxy-3-nitrobenzoate (from Step 1 in Preparation 4, 11 g, 52.1 mmol) was dissolved in a cold solution of ammonia in methanol (7N, 250 mL) and conc. aqueous ammonium hydroxide (100 mL) was added. The flask was stoppered and the resulting solution was allowed to gently stir at rt overnight (~17 h). LCMS analysis indicated complete conversion to more polar product consistent with the desired amide product (observed MH+ 197). The reaction mixture was concentrated on the rotovap using a slightly warm water bath to yield an aqueous slurry of the product. This slurry was diluted with additional water (~300 mL) and was sonicated briefly then the solid was collected by vacuum filtration and the resulting yellow solid was rinsed with additional water (~100 mL). The solid was air dried in the funnel for several hours then under vacuum to afford 7.12 g of a yellow solid as the pure product 2-methoxy-3-nitrobenzamide. A second crop of product was obtained by extracting the filtrate with EtOAc (3×100 mL) followed by washing the extracts with brine, drying over anhyd. Sodium sulfate, decanting and concentration under vacuum to afford 1.67 g of additional product as a yellow solid (86% overall combined yield). LCMS observed MH+ 197.

Step 2

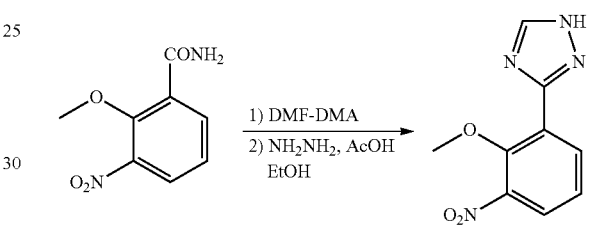

2-Methoxy-3-nitrobenzamide from Step 1 (7.1 g, 36.2 mmol) was slurried in DMF-DMA (48.5 mL, 362 mmol) and the mixture was heated to 95° C. giving a clear, pale yellow solution. After heating for ~30 min at this temp. LCMS indicated nearly the complete conversion of the starting material to afford a slightly less polar component as the major component having an apparent MH+ of 225 which was consistent with formylated product as an expected intermediate from DMF-DMA reaction. The reaction was cooled and was concentrated on the rotovap and the resulting yellow oil was azeotroped 2× with DCE (40 mL portions) to ensure complete removal of any residual DMF-DMA. The crude oil thus obtained was immediately dissolved in 35 mL of ethanol and was immediately used in the following step.

In a separate flask was prepared a mixture of ethanol (150 mL) and AcOH (35 mL) and the resulting solution was cooled in an ice bath. Once cooled, hydrazine hydrate (17.59 mL, 362 mmol) was added dropwise. At this time, the solution containing the crude DMF-DMA adduct of the substrate prepared above was transferred dropwise over ~15 min via cannula into the previously prepared well-stirred ice-cold mixture containing the hydrazine. During the addition, a pale yellow solid formed in the solution. After the addition was complete, the resulting cloudy yellow mixture was allowed to warm to rt and stir for ~4 h. LCMS analysis at this time showed mainly the desired triazole as the major product (observed MH+ 221). The reaction mixture at this time was concentrated on the rotovap to remove some of the ethanol, diluted with additional water and filtered to collect the solid. The solid was washed with additional portions of water, air dried in the funnel then under vacuum to afford 5.5 g (69%) of a pale yellow solid as the desired product. LCMS observed MH+ 221.

Step 3

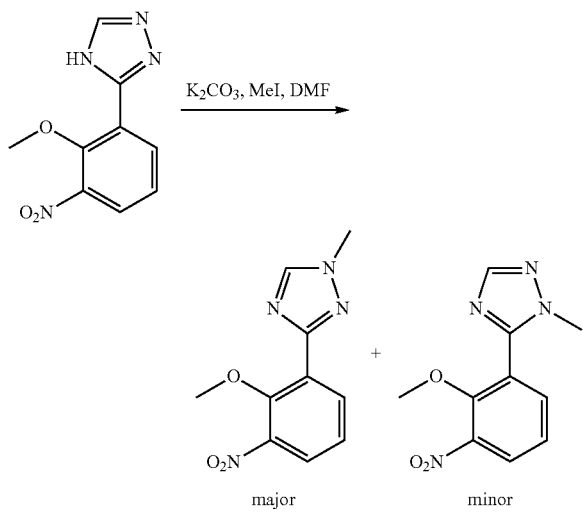

3-(2-Methoxy-3-nitrophenyl)-4H-1,2,4-triazole from Step 2 (2.23 g, 10.13 mmol) was dissolved in DMF (20 mL) and potassium carbonate (4.20 g, 30.4 mmol) was added. After cooling the resulting mixture in an ice bath, a solution of iodomethane (0.855 mL, 13.67 mmol) in DMF (5 mL) was slowly added dropwise via syringe over 2 min. After the addition was complete, the ice bath was removed and the reaction mixture was allowed to warm to rt. After stirring at rt for ~4 h, LCMS analysis indicated complete and clean conversion to the regioisomeric mixture of products in ~2:1 ratio, respectively. The reaction was cooled in an ice bath and was diluted with water (~50 mL) and the solution was extracted with EtOAc (3×40 mL) and the combined extracts were washed with 10% aq LiCl (2×20 mL), water (20 mL) then brine before concentrating to afford 2.17 g (91%) of a yellow oil as the crude product which solidified to a yellow solid upon standing. LCMS analysis indicated relatively pure product as a mixture of regioisomers (~2:1). LCMS observed MH+ 235. This crude material was combined with another batch of additional crude product (~0.45 g) from a previous similar reaction and the material was purified by SFC chromatography to resolve the isomers (Conditions: column=Chiral IC 3×25 cm, 5 μm; column temp.=35° C.; flow rate=200 mL/min; mobile phase=CO$_2$/MeOH=80/20; injection program=stacked (2.3 min/cycle), 2.5 ml/per injection; sampler conc. (mg/mL): 60 mg/mL; detector wavelength=220 nm) to afford 1.87 g (65%) of the major isomer as a pale yellow solid. LCMS MH+ 235. $^1$H NMR (400 MHz, methanol-d$_4$) δ 8.54 (s, 1H), 8.15 (dd, J=7.9, 1.8 Hz, 1H), 7.89 (dd, J=8.1, 1.8 Hz, 1H), 7.42 (t, J=7.9 Hz, 1H), 4.07 (s, 3H), 3.87 (s, 3H).

Step 4

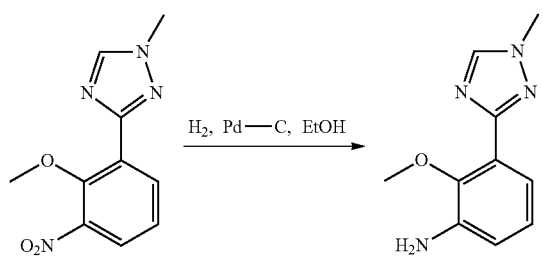

A solution of 3-(2-methoxy-3-nitrophenyl)-1-methyl-1H-1,2,4-triazole from Step 3 (1.87 g, 7.98 mmol) was dissolved in ethanol (50 mL) and the solution was sparged with nitrogen for a few minutes before adding 5% Pd—C (0.850 g, 0.399 mmol) followed by sparging with hydrogen from a balloon for a few minutes then allowing the mixture to stir under a balloon of hydrogen for 1.5 h at rt. LCMS analysis at this time indicated complete and clean conversion of the starting material to afford a single more polar product consistent with the expected aniline product (observed MH+ 205). The mixture was then sparged with nitrogen to deactivate the catalyst and the mixture was filtered through a pad of CELITE® washing with additional amounts of EtOH and the resulting clear, colorless filtrate containing the product was concentrated under vacuum to afford a colorless oil. This material was azeotroped with two portions of dry toluene (~25 mL each) to afford an off-white solid which was dried further under vacuum to afford 1.5 g (92%) of a free-flowing white solid as the pure product. LCMS MH+ of 205. $^1$H NMR (400 MHz, methanol-d$_4$) δ 8.54-8.41 (m, 1H), 7.12 (dd, J=7.6, 1.7 Hz, 1H), 7.02-6.96 (m, 1H), 6.94-6.89 (m, 1H), 4.03 (s, 3H), 3.69 (s, 3H).

Preparation 7

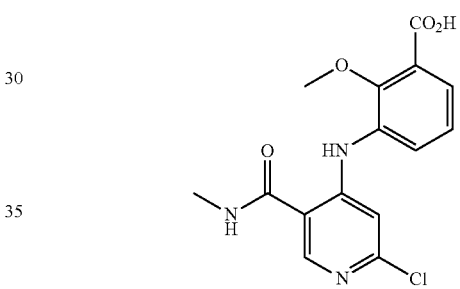

Step 1

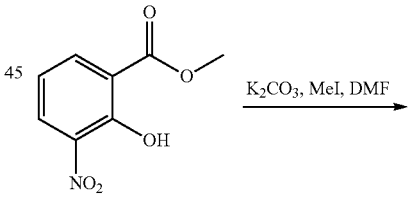

To a solution of methyl 2-hydroxy-3-nitrobenzoate (10 g, 50.7 mmol) in DMF (100 mL) at rt was added potassium carbonate (14.02 g, 101 mmol) followed by addition of methyl iodide (6.34 mL, 101 mmol) and the resulting orange mixture was heated to 60° C. for 1 h. LCMS analysis at this time showed complete and clean conversion to a major product consistent with the expected product (observed MH+ 212). Let cool to rt and added crushed ice (~100 mL) followed by water to a total volume of ~400 mL causing a nice yellow solid to crystallize from solution. Stirred for a few minutes to give a nice slurry then collected solid by vacuum filtration and the resulting initially yellow solid was rinsed with additional water (~100 mL) until all of the yellow color was rinsed into the filtrate giving a near white solid in the funnel. Partially air-dried solid in funnel then transferred to a round bottomed flask and further dried under vacuum overnight to afford 10.5 g (98%) of a yellow solid as methyl 2-hydroxy-3-nitrobenzoate. LCMS MH+ 212.

Preparation 8

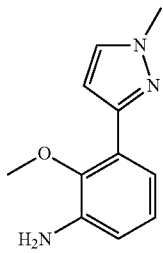

Step 1

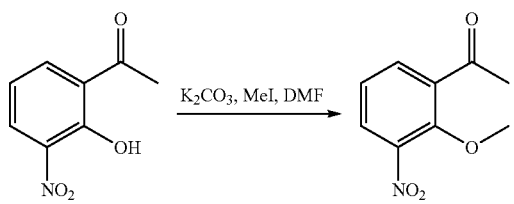

A slurry of 1-(2-hydroxy-3-nitrophenyl)ethanone (1.00 g, 5.52 mmol) and potassium carbonate (3.05 g, 22.08 mmol) in DMF (20 mL) was stirred at rt for 30 min, then iodomethane (1.338 mL, 16.56 mmol) was added dropwise and the resulting mixture was allowed to stir at rt overnight. LCMS indicated some unreacted starting material remained, therefore additional iodomethane (1.338 mL, 16.56 mmol) was added and the mixture was warmed to 50° C. over 2 days. Reaction was quenched by the addition of water to give a solution followed by adjusting the pH with 1N HCl to ~7. The resulting solution was extracted with EtOAc (80 mL×3) and the combined organic extracts were washed with brine, dried over anhyd sodium sulfate, filtered and concentrated to afford the product, 1-(2-methoxy-3-nitrophenyl)ethanone (1.05 g, 5.38 mmol, 97% yield) as a tan oil. HPLC (method N) RT=1.86 min.

Step 2

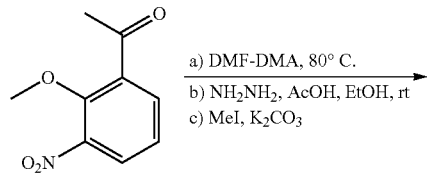

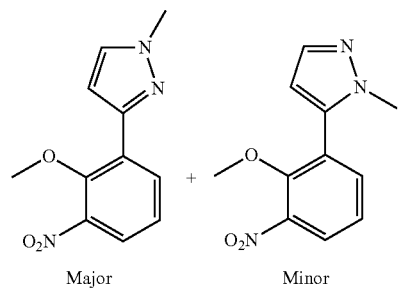

A slurry of 1-(2-methoxy-3-nitrophenyl)ethanone (450 mg, 2.306 mmol) in DMF-DMA (8.148 g, 68.4 mmol) was heated to 80° C. giving a clear solution. After stirring at this temperature for ~30 min., the reaction was cooled, diluted with 100 mL of EtOAc, washed with water (3×), then brine, dried over $Na_2SO_4$, filtered and concentrated to afford tan oil as the crude intermediate (432 mg). To this material was added ethanol (4.0 mL) to make a homogeneous tan solution and followed by cooling in an ice bath. At this time, hydrazine hydrate (0.217 mL, 6.92 mmol) was slowly added dropwise via syringe with good stirring. After the addition was complete, the reaction was allowed to warm to rt then was heated to 80° C. for 1 h then cooled to rt and allowed to stir at rt overnight. The resulting mixture was concentrated to remove the ethanol, diluted with 100 mL of EtOAc, washed with water for 3 times, then brine, dried over sodium sulfate, filtered and concentrated to afford a tan semi-solid as the crude pyrazole intermediate. To this intermediate was added 4 mL of acetone and potassium carbonate (956 mg, 6.92 mmol), and the resulting mixture was stirred at rt for 10 min before adding iodomethane (0.577 mL, 9.22 mmol). After stirring at rt overnight, the reaction mixture was concentrated and was partitioned between EtOAc and water. The layers were separated and the organic portion was washed with water (3×), dried over sodium sulfate, filtered and concentrated under vacuum to afford tan oil as the crude product. This material was purified by flash silica gel chromatography using hexanes/EtOAc mixtures as the eluant. Fractions containing the major uv active component were combined and concentrated under vacuum to afford 155 mg (29% overall yield) of a tan oil which was determined to be the desired product as a mixture of regioisomers (~4-5:1). HPLC (method N) RT=2.50 min (regioisomers unresolved). LCMS (m+1)=235. $^1$H NMR (400 MHz, methanol-$d_4$) δ 8.07 (dd, J=7.9, 1.5 Hz, 1H), 7.76 (dd, J=8.0, 1.7 Hz, 1H), 7.72 (d, J=2.4 Hz, 1H), 7.36 (t, J=7.9 Hz, 1H), 6.80 (d, J=2.2 Hz, 1H), 4.01 (s, 3H), 3.77 (s, 3H).

Step 3

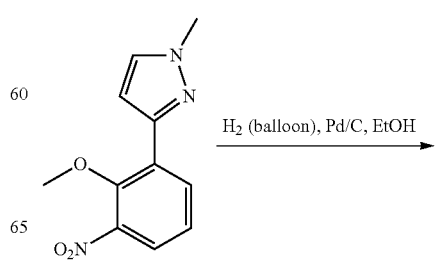

Step 2

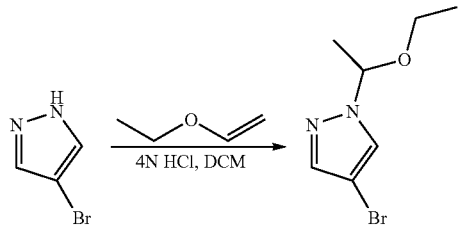

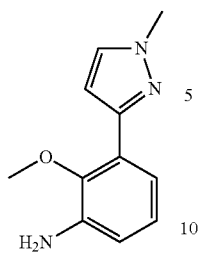

To solution of 4-bromo-1H-pyrazole from Step 1 (21.6 g, 147 mmol) in dichloromethane (400 mL) was added a solution of HCl (4 N in dioxane) (2.204 mL, 8.82 mmol) and ethoxyethene (12.72 g, 176 mmol). After stirring this mixture at rt for 30 min, the reaction was quenched with aqueous NaHCO$_3$ (30 mL), stirred at rt for 1 h, and the two layers obtained were separated. The organic layer was washed with water, dried over anhyd sodium sulfate, and concentrated under reduced pressure to afford 28 g of crude product. This material was purified by silica gel flash chromatography using hexanes/ethyl acetate mixtures as the eluant. Fractions containing the major uv active product were combined and concentrated under vacuum to afford 13.2 g (41%) of a clear oil as the desired product. HPLC (method N) RT=2.34 min. $^1$H NMR (400 MHz, chloroform-d) δ 7.61 (s, 1H), 7.47 (s, 1H), 5.48 (q, J=5.9 Hz, 1H), 3.53-3.41 (m, 1H), 3.35 (dq, J=9.5, 7.0 Hz, 1H), 1.68-1.62 (m, 3H), 1.21-1.12 (m, 3H).

To a clear solution of product from Step 2 (0.15 g, 0.643 mmol) in EtOH (10 mL) was added Pd/C (10% on Carbon) (0.021 g, 0.019 mmol). The flask was evacuated and supplied with hydrogen gas from a balloon for 3 h. The hydrogen balloon was removed and reaction was flashed with nitrogen, 50 mL of EtOH was added, and the reaction mixture was filtered and the filtrate was concentrated to afford 2-methoxy-3-(1-methyl-1H-pyrazol-3-yl)aniline (120 mg, 0.590 mmol, 92% yield) as Preparation 8 which contained ~20% of a minor regioisomer. HPLC (method N) RT=0.96 min. (major) and 1.12 min (minor). LCMS (m+1)=204.

Step 3

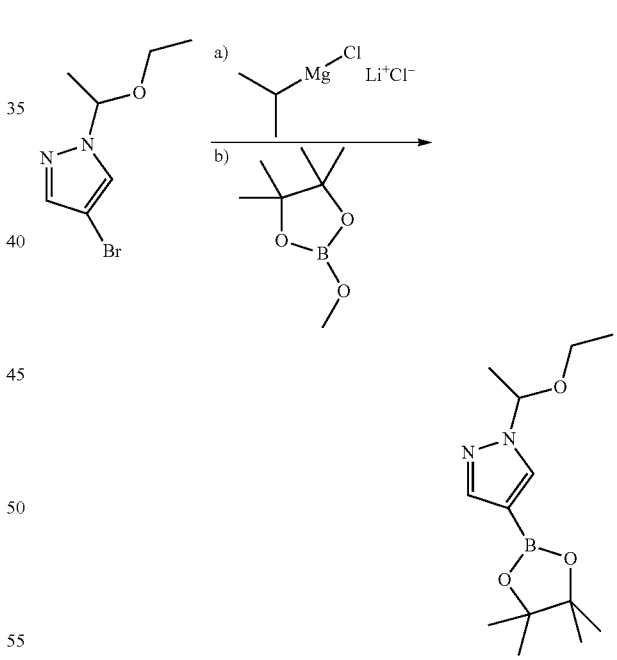

Preparation 9

[Structure of 2-methoxy-3-(1-(1-ethoxyethyl)-1H-pyrazol-3-yl)aniline]

Step 1

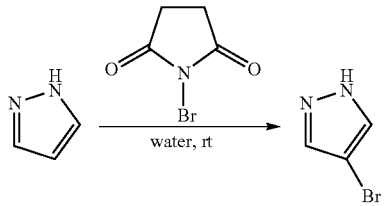 [SMILES: c1cn[nH]c1 ; O=C1CCC(=O)N1Br ; Brc1cn[nH]c1]

To a slurry of 1H-pyrazole (10 g, 147 mmol) in water (150 mL) at rt was added NBS (26.1 g, 147 mmol) in one portion (caution: exothermic) and the mixture became milky white and was allowed to stir at rt overnight. The reaction mixture was then extracted with EtOAc (2×100 mL). The combined organic extracts was washed with aqueous Na$_2$S$_2$O$_3$ and brine, dried over anhyd sodium sulfate, and concentrated under reduced pressure to afford the desired product, 4-bromo-1H-pyrazole (21.5 g, 146 mmol, 100% yield) as an initial oil which solidified upon standing. HPLC (method N) RT=0.87 min.

To an oven dried vial was charged a solution of isopropylmagnesium chloride-lithium chloride complex (1.0 M in THF) (6.32 ml, 8.22 mmol) at rt, and 4-bromo-1-(1-ethoxyethyl)-1H-pyrazole from Step 2 (1.00 g, 4.56 mmol) was added dropwise and the resulting mixture was stirred at rt overnight. The solution obtained was then cooled to −20° C. and 2-methoxy-4,4,5,5-tetramethyl-1,3,2-dioxaborolane (1.731 g, 10.95 mmol) was added dropwise via syringe. After the addition was complete, the reaction was allowed to slowly warm to rt and stir at rt for 2 h. The reaction was quenched at this time by the addition of aq. sat. NH$_4$Cl (15 mL) which caused a white precipitate to form. Water was added (20 mL) and the mixture was extracted with hexanes (140 mL×2). The combined extracts were washed with aq. sat. sodium bicarbonate, brine, then dried over anhyd sodium sulfate, filtered and concentrated to afford 1.20 g (99%) of the desired product as a colorless oil. $^1$H NMR (400 MHz, chloroform-d) δ 7.91 (s, 1H), 7.79 (s, 1H), 5.55 (q, J=5.9 Hz, 1H), 3.51-3.39 (m, 1H), 3.37-3.25 (m, 1H), 1.67 (d, J=5.9 Hz, 3H), 1.37-1.30 (m, 12H), 1.15 (t, J=7.0 Hz, 3H).

Step 4

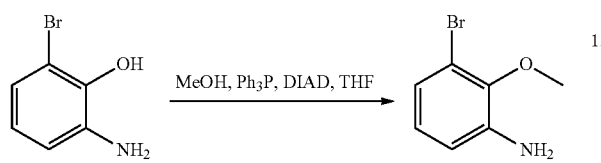

To a slurry of 2-amino-6-bromophenol (4.00 g, 21.27 mmol) in methanol (2.152 mL, 53.2 mmol) and THF (10 mL) at rt was added triphenylphosphine (11.16 g, 42.5 mmol). After stirring for a few minutes, DIAD (12.41 mL, 63.8 mmol) was then added dropwise via syringe over ~5 min. (exothermic). After the addition was complete, the reaction which had warmed due to the exothermic reaction was allowed to stir at rt for ~1 h. The resulting mixture was then concentrated to remove the volatiles and the resulting residue was purified by silica gel flash chromatography using hexanes/ethyl acetate as the eluant. Fractions containing the major uv active product were combined and concentrated under vacuum to afford 2.35 g (55%) of a dark brown oil as the desired product. HPLC (method N) RT=1.33 min. LCMS MH+ 202/204 (observed bromide isotope pattern).

Step 5

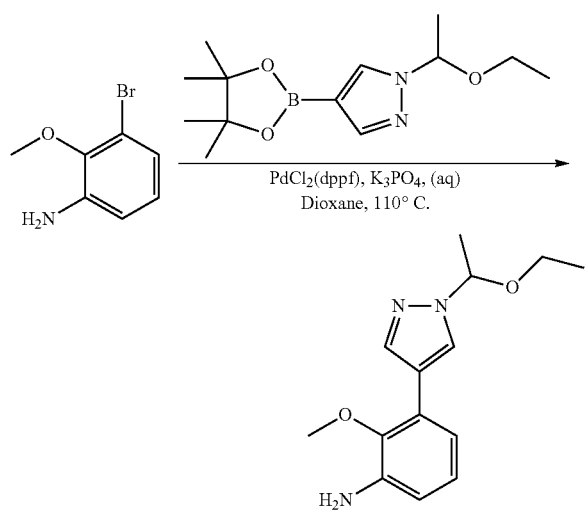

To a reaction vial charged with 3-bromo-2-methoxyaniline from Step 4 (0.30 g, 1.485 mmol) and 1-(1-ethoxyethyl)-4-(4,4,5,5-tetramethyl-1,3,2-dioxaborolan-2-yl)-1H-pyrazole from Step 3 (0.435 g, 1.633 mmol) in dioxane (2 ml) was added aqueous potassium phosphate (2.0 M) (1.485 ml, 2.97 mmol). The resulting mixture was deoxygenated by bubbling argon through the mixture for ~5 min. PdCl$_2$(dppf) (0.033 g, 0.045 mmol) was then added and the mixture was heated at 110° C. for 3 h then cooled to rt. The resulting mixture was diluted with EtOAc (100 mL), washed with water, brine, dried over anhyd sodium sulfate, filtered and concentrated to afford a black oil as the crude product mixture. This material was purified by silica gel flash chromatography using hexanes/ethyl acetate solvent mixtures as the eluant. Fractions containing the major uv active component were collected and combined then concentrated under vacuum to afford the desired product, Preparation 9 (355 mg, 1.358 mmol, 91% yield) as an oil which solidified upon standing. HPLC (method N) RT=1.58 min. LCMS (m+1)=262.1.

Preparation 10

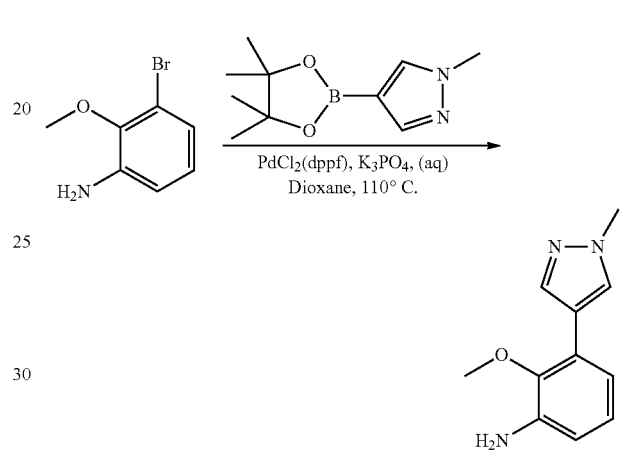

To a reaction vial charged with 3-bromo-2-methoxyaniline (from Step 4 of Preparation 9, 1.12 g, 5.54 mmol), 1-methyl-4-(4,4,5,5-tetramethyl-1,3,2-dioxaborolan-2-yl)-1H-pyrazole (1.499 g, 7.21 mmol) in dioxane (6 mL) was added aqueous potassium phosphate (2.0 M) (5.54 ml, 11.09 mmol). The resulting mixture was deoxygenated by bubbling argon through the mixture for ~5 min. PdCl$_2$(dppf) (0.122 g, 0.166 mmol) was then added and the mixture was heated at 110° C. for 2 h. The reaction was cooled, diluted with EtOAc (200 mL), washed with water, brine, dried over anhyd sodium sulfate, filtered and concentrated to afford tan oil as the crude product mixture. This material was purified by silica gel flash chromatography using hexanes/ethyl acetate mixtures as the eluant. Fractions containing the desired product were collected, combined, and concentrated under vacuum to afford 0.87 g (77%) of the desired product (Preparation 10) as an oil which solidified upon standing. HPLC (method N)=0.89 min. LCMS MH+204.1.

Preparation 11

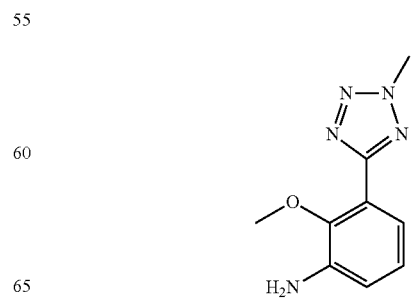

Step 1

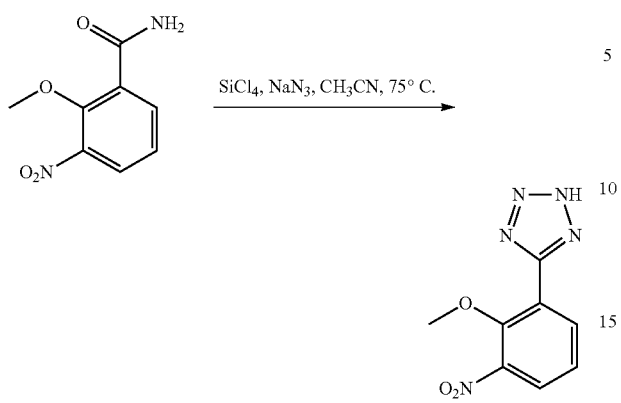

Sodium azide (1.193 g, 18.35 mmol) was suspended in acetonitrile (10.0 mL) at rt and silicon tetrachloride (0.772 mL, 6.73 mmol) was added causing the reaction mixture to become milky white in color. At this time, 2-methoxy-3-nitrobenzamide from Step 1 of Preparation 6 (1.20 g, 6.12 mmol) was added as solid and the mixture was heated at 75° C. for 4 h. The reaction was cooled to rt, water (50 mL) was added to give a slurry which was sonicated and the resulting solid which had formed was collected by vacuum filtration, rinsed with water, and dried on the filter to afford the product, 5-(2-methoxy-3-nitrophenyl)-2H-tetrazole (1.20 g, 5.43 mmol, 89% yield) as a yellow solid. HPLC (method N) RT=1.57 min. LCMS MH+ 222.1.

Step 2

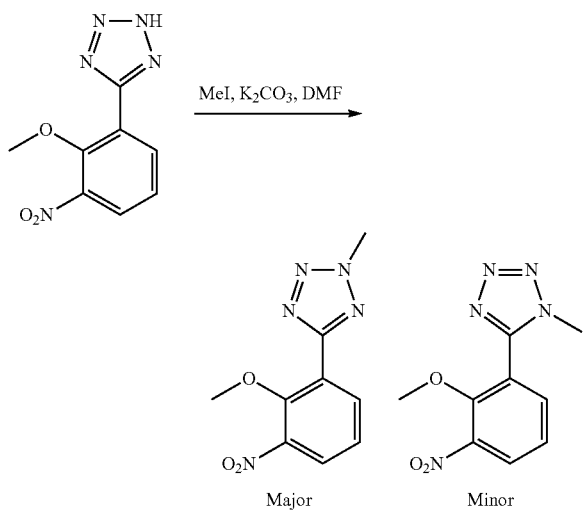

To a solution of 5-(2-methoxy-3-nitrophenyl)-2H-tetrazole from Step 1 (1.20 g, 5.43 mmol) in DMF (6.0 mL) was added iodomethane (0.679 mL, 10.85 mmol) in 1 mL of DMF and the resulting mixture was stirred at rt for 3 h. The reaction mixture was cooled in an ice bath and was diluted with water (~100 mL) and the solution was extracted with EtOAc (3×100 mL) and the combined extracts were washed with 10% aq LiCl (2×40 mL), water (40 mL) then brine, and dried over anhyd sodium sulfate before concentrating to afford 1.30 g of a yellow oil as the crude product as a mixture of regioisomers (~2:1) by HPLC analysis. To resolve the isomers, this material was purified by SFC chromatography using the conditions—Column: Cell 45×25 cm, 5 μm; Column Temp. 40° C.; Flow rate: 200 mL/min; Mobile Phase: CO₂/MEOH=80/20; Injection Program: Stacked (2.5 min/cycle), 3.5 ml/per injection; Sampler conc. (mg/mL): 30 mg/mL; Detector Wavelength: 220 nm. This afforded 0.735 g (58%) of a tan solid which was assigned as the major isomer 5-(2-methoxy-3-nitrophenyl)-2-methyl-2H-tetrazole and 0.334 g (26%) of a tan solid which was assigned as the minor isomer 5-((2-methoxy-3-nitrophenyl)-1-methyl-1H-tetrazole.

Major isomer: HPLC (method N) RT=2.14 min. LCMS MH+ 236.1.

Minor isomer: HPLC (method N) RT=1.57 min. LCMS MH+ 236.1.

Step 3

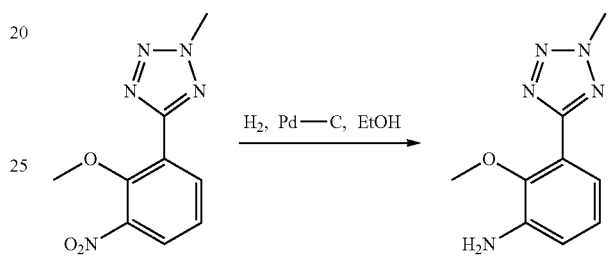

A solution of 5-(2-methoxy-3-nitrophenyl)-2-methyl-2H-tetrazole from Step 2 (0.73 g, 3.10 mmol) in EtOH (20 mL) was sparged with nitrogen for a few minutes before adding 5% Pd—C (0.165 g, 0.155 mmol) followed by sparging with hydrogen from a balloon for a few minutes then letting mixture stir under a balloon of hydrogen for 1.5 h at rt. LCMS analysis at this time indicated complete and clean conversion of the starting material to afford a single more polar product consistent with the expected aniline product (observed MH+ 206). The mixture was then sparged with nitrogen to deactivate the catalyst and the mixture was filtered through millipore 45μ filter washing with additional amounts of EtOH and the resulting clear, colorless filtrate containing the product was concentrated under vacuum to afford a colorless oil. This material was azeotroped with two portions of dry toluene (~25 mL each), then further dried under vacuum to afford colorless oil initially which eventually solidified to afford a white solid as the product (Preparation 11), 2-methoxy-3-(2-methyl-2H-tetrazol-5-yl)aniline (630 mg, 3.07 mmol, 99% yield). HPLC (method N) RT=0.74 min. LCMS (m+1)=206.1.

Preparation 12

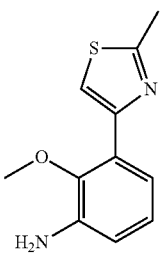

Step 1

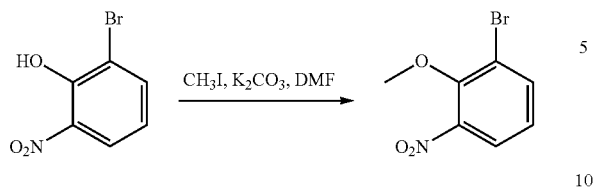

To a solution of 2-bromo-6-nitrophenol (5 g, 22.94 mmol) in DMF (18 ml) was added potassium carbonate (9.51 g, 68.8 mmol) and the resulting mixture was stirred for 15 min, then iodomethane (2.87 ml, 45.9 mmol) was added. The resulting mixture was stirred at rt overnight. HPLC and LCMS indicated complete conversion to product. Cold water added (75 mL), stir/sonicate, solid was collected by filtration. This material was then dissolved in EtOAc (150 mL). This solution was washed 1×10% LiCl, 1× brine. dried over sodium sulfate, then filtered and concentrated. Loaded onto a 120 g silica gel cartridge, then purified by flash chromatography eluting with 0-50% EtOAc in hexanes. Fractions containing the product were concentrated to afford a pale yellow solid as the product 1-bromo-2-methoxy-3-nitrobenzene (4.997 g, 20.46 mmol, 89% yield). LCMS gave very weak MH+.

Step 2

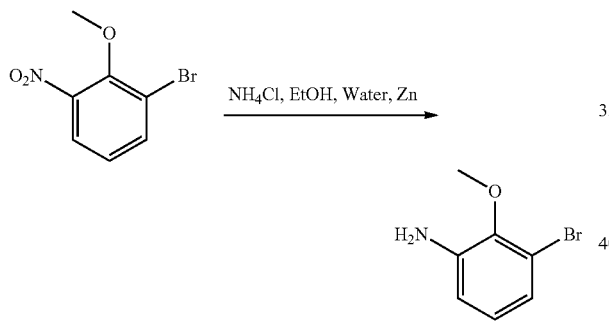

A mixture of 1-bromo-2-methoxy-3-nitrobenzene from Step 1 (3 g, 11.64 mmol), zinc metal (7.61 g, 116 mmol) and ammonium chloride (6.22 g, 116 mmol) in EtOH (50 mL) and water (7.14 mL) was stirred at rt overnight. The reaction was then diluted with dichloromethane (200 mL), and filtered. The filtrate was washed with water (50 mL), dried (sodium sulfate), and concentrated. Redissolved this material in dichloromethane, and loaded onto a 80 g silica gel column for purification by flash chromatography, eluting with 0-100% EtOAc in hexanes. Afforded 3-bromo-2-methoxyaniline (2.11 g, 9.92 mmol, 85% yield) as a colorless oil.

Step 3

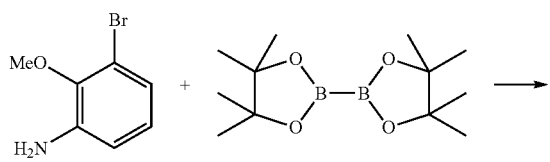

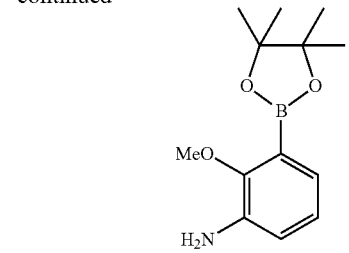

A solution of 3-bromo-2-methoxyaniline from Step 2 (1.94 g, 9.60 mmol), 4,4,4',4',5,5,5',5'-octamethyl-2,2'-bi(1,3,2-dioxaborolane) (3.66 g, 14.40 mmol), PdCl$_2$(dppf)-CH$_2$Cl$_2$ complex (0.392 g, 0.480 mmol) and potassium acetate (2.83 g, 28.8 mmol) in dioxane (32 mL) in a flask was heated to reflux (~100° C.) overnight then cooled to room temperature, concentrated in vacuo on CELITE®. This crude product was purified by flash chromatography using a 120 g silica gel column (solid loading) eluting with 0-50% ethyl acetate/hexanes. Appropriate fractions (eluted near 25% EtOAc/hexanes) were collected and concentrated in vacuo to give 2-methoxy-3-(4,4,5,5-tetramethyl-1,3,2-dioxaborolan-2-yl)aniline (1.47 g, 5.78 mmol, 60.2% yield) as a crystalline off-white solid. LCMS MH+ 250.1.

Step 4

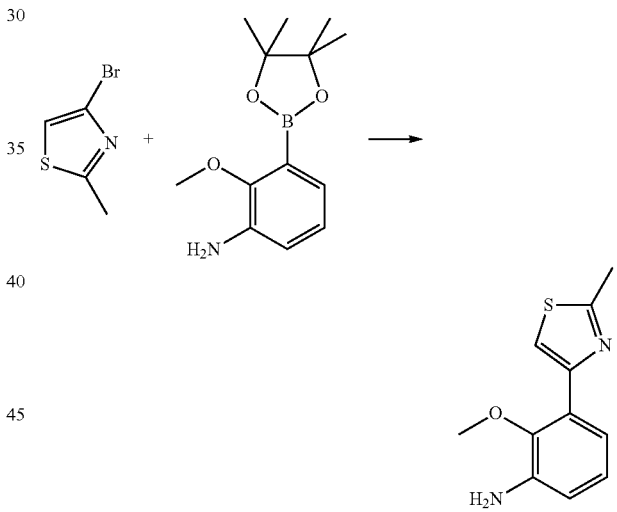

A stirred mixture of 4-bromo-2-methylthiazole (128 mg, 0.719 mmol), 2-methoxy-3-(4,4,5,5-tetramethyl-1,3,2-dioxaborolan-2-yl)aniline from Step 3 (197 mg, 0.791 mmol) and 1,1'-bis(di-tert-butylphosphino)ferrocene palladium dichloride (14.06 mg, 0.022 mmol) in dioxane (4 mL) was degassed by bubbling nitrogen through the mixture for 5 minutes. 2M sq potassium phosphate dibasic solution (1.078 mL, 2.157 mmol) was quickly added and the reaction mixture heated at 100° C. for one hour. LC-MS showed complete conversion to the desired product mass. The reaction mixture was cooled to room temperature, then diluted with EtOAc (75 mL). This solution was then dried over sodium sulfate, filtered, concentrated and purified by flash chromatography, eluting with 0-100% EtOAc in hexanes. Afforded 2-methoxy-3-(2-methylthiazol-4-yl)aniline (Preparation 12, 122 mg, 0.543 mmol, 75% yield) as a yellow oil. LCMS MH+221.1.

Example 28

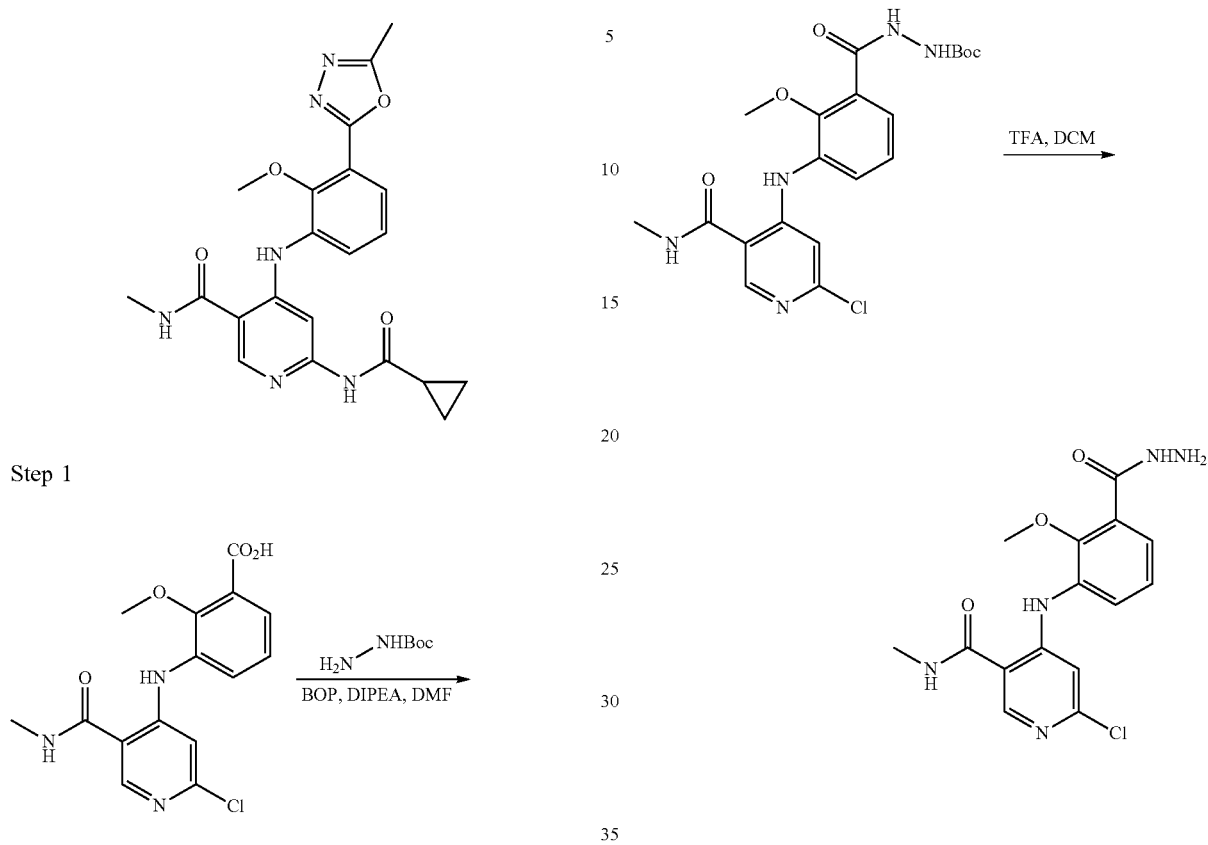

Step 1

Dissolved Preparation 4 (300 mg, 0.894 mmol), tert-butyl hydrazinecarboxylate (142 mg, 1.072 mmol) and diisopropylethylamine (0.187 mL, 1.072 mmol) in DMF (3 mL) and let stir for a few minutes before adding BOP reagent (435 mg, 0.983 mmol). After stirring at rt for ~30 min, cold water was added causing a solid to precipitate. The slurry was briefly sonicated and the solid was collected by filtration and dried on the filter to afford the product, tert-butyl 2-(3-((2-chloro-5-(methylcarbamoyl)pyridin-4-yl)amino)-2-methoxybenzoyl)hydrazinecarboxylate (356 mg, 0.791 mmol, 89% yield). HPLC (method N) RT=2.81 min. LCMS (m+1)=450/452.

Step 2

To slurry of the product from Step 1 (356 mg, 0.791 mmol) in DCM (2 mL) was added TFA (0.610 mL, 7.91 mmol) to make clear solution followed by stirring at rt for 1 h. The resulting mixture was then concentrated to remove the DCM and TFA, and DCM (10 mL) was added and the mixture was concentrated to dryness again followed by repeating this process one additional time. The resulting pale yellow oil obtained was triturated with ether (30 mL×2) to afford a near white solid as the presumed TFA salt of the final product, 6-chloro-4-((3-(hydrazinecarbonyl)-2-methoxyphenyl)amino)-N-methylnicotinamide (356 mg, 0.768 mmol, 97% yield). HPLC (method N) RT=1.81 min. LCMS (m+1)=350.

Step 3

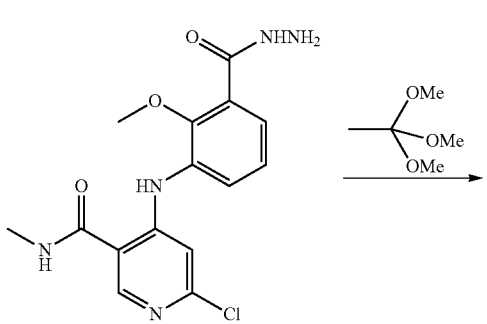

-continued

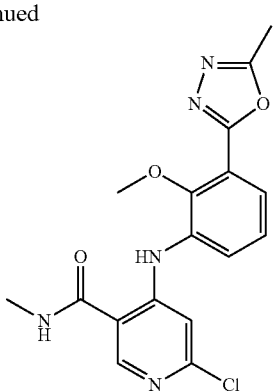

The product from Step 2 (356 mg, 0.768 mmol) in 1,1,1-trimethoxyethane (1844 mg, 15.35 mmol) was heated at 90° C. for 4 h then cooled down and concentrated to remove excess 1,1,1-trimethoxyethane. After cooling the residue in an ice bath, aq sat. sodium bicarbonate (4 mL) was added and the mixture was sonicated to give a slurry and the solid was collected by vacuum filtration, rinsed with water, and dried on the filter to afford the product as a tan solid (186 mg, 0.498 mmol, 64.8% yield). HPLC (method N) RT=2.81 min. LCMS (m+1)=375.

Step 4

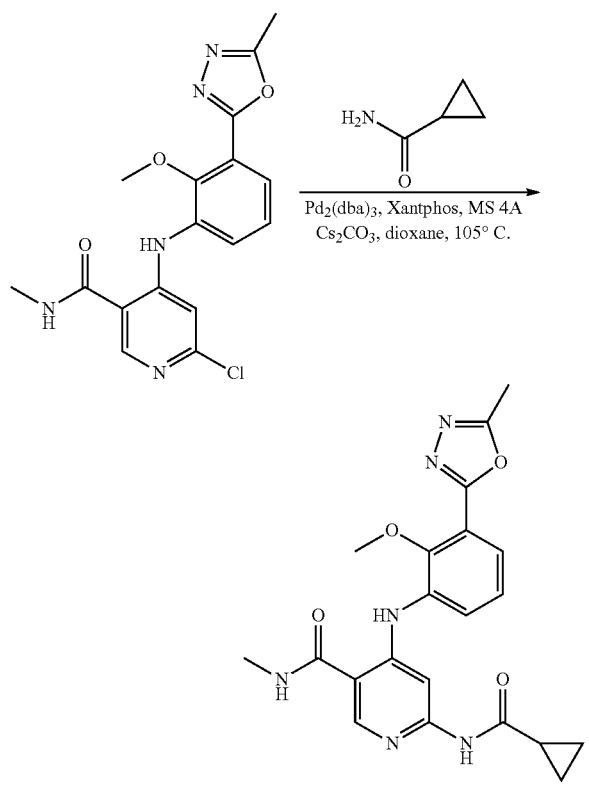

A mixture of the product from Step 3 (15 mg, 0.040 mmol), cyclopropanecarboxamide (6.83 mg, 0.080 mmol), Xantphos (4.64 mg, 8.03 µmol), 4A powdered molecular sieves (20 mg) and cesium carbonate (26.1 mg, 0.080 mmol) in dioxane (0.5 mL) was sparged with nitrogen for 5 min., then $Pd_2(dba)_3$ (7.35 mg, 8.03 µmol) was added and the reaction was placed into a preheated 105° C. heating block.

After stirring at this temp for 4 h, the reaction was cooled to rt, diluted with DMF, filtered and was purified by reverse phase preparative LCMS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 0-100% B over 20 minutes, then a 5-minute hold at 100% B; Flow: 20 mL/min. Fractions containing the desired product were combined and dried via centrifugal evaporation. The yield of the product (Example 28) was 6.9 mg (41%). HPLC (Method E) RT=1.17 min. HPLC (Method G) RT=0.91 min. LCMS observed MH+=423.2. $^1$H NMR (500 MHz, DMSO-$d_6$) δ 10.81 (s, 1H), 10.77 (s, 1H), 8.66 (d, J=4.9 Hz, 1H), 8.54 (s, 1H), 8.05 (s, 1H), 7.66 (d, J=7.9 Hz, 1H), 7.59 (d, J=7.3 Hz, 1H), 7.34 (t, J=7.9 Hz, 1H), 3.76 (s, 3H), 2.79 (d, J=4.3 Hz, 3H), 2.60 (s, 3H), 2.07-1.85 (m, 1H), 0.78 (d, J=6.1 Hz, 4H).

Example 29

Step 1

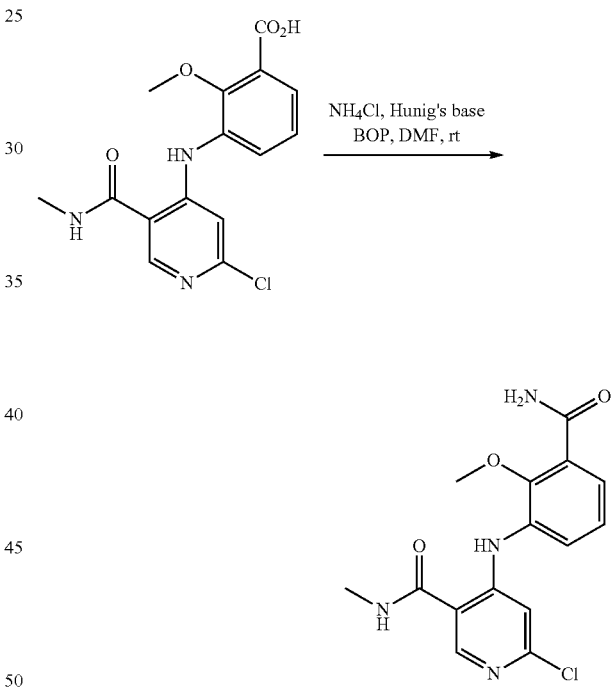

Mixed Preparation 4 (1.09 g, 3.25 mmol), Hunig's base (1.701 mL, 9.74 mmol) and ammonium chloride (0.347 g, 6.49 mmol) in DMF (4 mL) at rt for a few minutes then added BOP (1.867 g, 4.22 mmol) to the resulting slurry. Let slurry stir at rt for 1 h then crushed ice was added to the reaction mixture and the resulting suspension was sonicated briefly then the precipitated solid was collected by vacuum filtration and air dried in the funnel to afford the product, 4-((3-carbamoyl-2-methoxyphenyl)amino)-6-chloro-N-methylnicotinamide (1.07 g, 3.20 mmol, 98% yield) as a light tan solid. HPLC (method N) RT=2.24 min. LCMS (m+1)=335.

Step 2

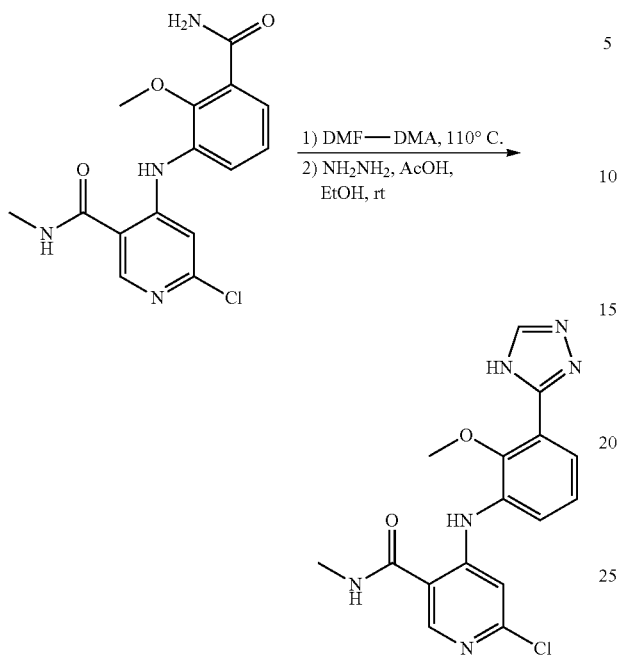

A slurry of the product from Step 1 (300 mg, 0.896 mmol) in DMF-DMA (2.400 mL, 17.93 mmol) was heated to 110° C. giving a clear solution. After heating at this temperature for 3 h, the reaction was cooled and concentrated to remove the DMF-DMA and the resulting semi-solid residue was dissolved in ethanol (0.7 mL) and acetic acid (3.50 mL) to make clear solution which was immediately cooled to −10° C. in a brine/ice bath whereupon hydrazine hydrate (0.281 mL, 8.96 mmol) was slowly added dropwise via syringe with good stirring. After addition was complete, the resulting slurry was allowed to warm to rt and stir overnight. The mixture was concentrated to remove most of the ethanol and acetic acid and the resulting aqueous slurry was diluted with water and the solids were collected by vacuum filtration, rinsed with additional water, and dried on the filter to afford the product, 6-chloro-4-((2-methoxy-3-(4H-1,2,4-triazol-3-yl)phenyl)amino)-N-methylnicotinamide (280 mg, 0.780 mmol, 87% yield). HPLC (method N) RT=2.51 min. LCMS (m+1)=359/361.

Step 3

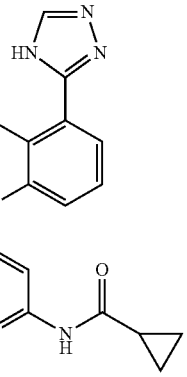

-continued

To a reaction vial was added the product from Step 2 (20 mg, 0.056 mmol), cyclopropanecarboxamide (4.74 mg, 0.056 mmol) and BrettPhos (3.59 mg, 6.69 μmol) and the contents were purged with nitrogen before adding DMA (0.10 mL) and dioxane (0.20 mL). The resulting slurry was sparged with nitrogen for an additional minute, then $Pd_2(dba)_3$ (5.10 mg, 5.57 μmol) followed by LiHMDS (1 M in THF) (0.139 mL, 0.139 mmol) was added and the reaction vial was capped under nitrogen and placed into a preheated 110° C. heating block and the mixture was allowed to stir at that temperature for 1.5 h. After cooling, the reaction was quenched with MeOH, concentrated to remove the volatiles, and was purified by reverse phase preparative LCMS with the following conditions: Column: Waters XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 20 minutes, then a 5-minute hold at 100% B; Flow: 20 mL/min. Fractions containing the desired product were combined and dried via centrifugal evaporation. The yield of the product (Example 29) was 15.4 mg (49%). HPLC (Method E) RT=0.98 min. HPLC (Method G) RT=0.76 min. LCMS observed MH+=408.2. $^1$H NMR (500 MHz, DMSO-$d_6$) δ 11.11 (br. s., 1H), 10.82 (br. s., 1H), 8.79 (br. s., 1H), 8.49 (s, 1H), 7.75 (d, J=6.7 Hz, 1H), 7.54 (d, J=7.9 Hz, 1H), 7.38-7.27 (m, 1H), 3.69 (s, 3H), 2.81 (d, J=4.3 Hz, 3H), 1.91 (br. s., 1H), 0.90-0.78 (m, 4H).

Example 30

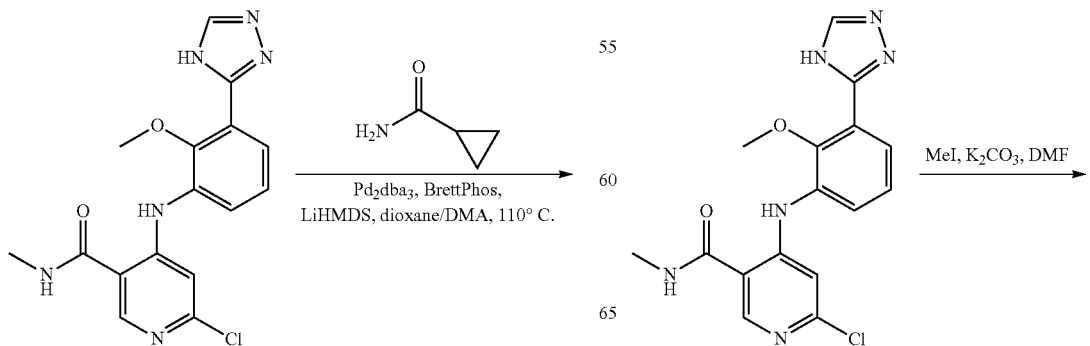

Step 1

To slurry of product from Step 2 of Example SW50 (80 mg, 0.223 mmol) and potassium carbonate (61.6 mg, 0.446 mmol) in DMF (0.5 mL) at rt was added 0.3 mL solution of iodomethane (240 mg in 2 mL of acetonitrile). The resulting mixture was allowed to stir at rt for 30 min before quenching with cold water. Brief sonication of the resulting slurry and vacuum filtration gave a solid which was rinsed with water and dried to afford 39 mg (47%) of the product as an off-white solid. HPLC (method N) RT=2.61 min. LCMS (m+1)=373.

Step 2

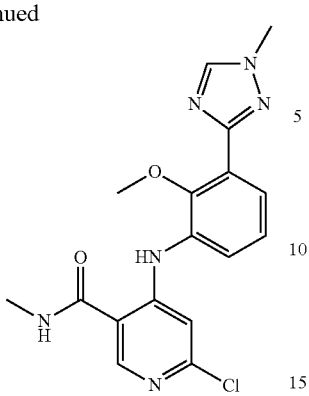

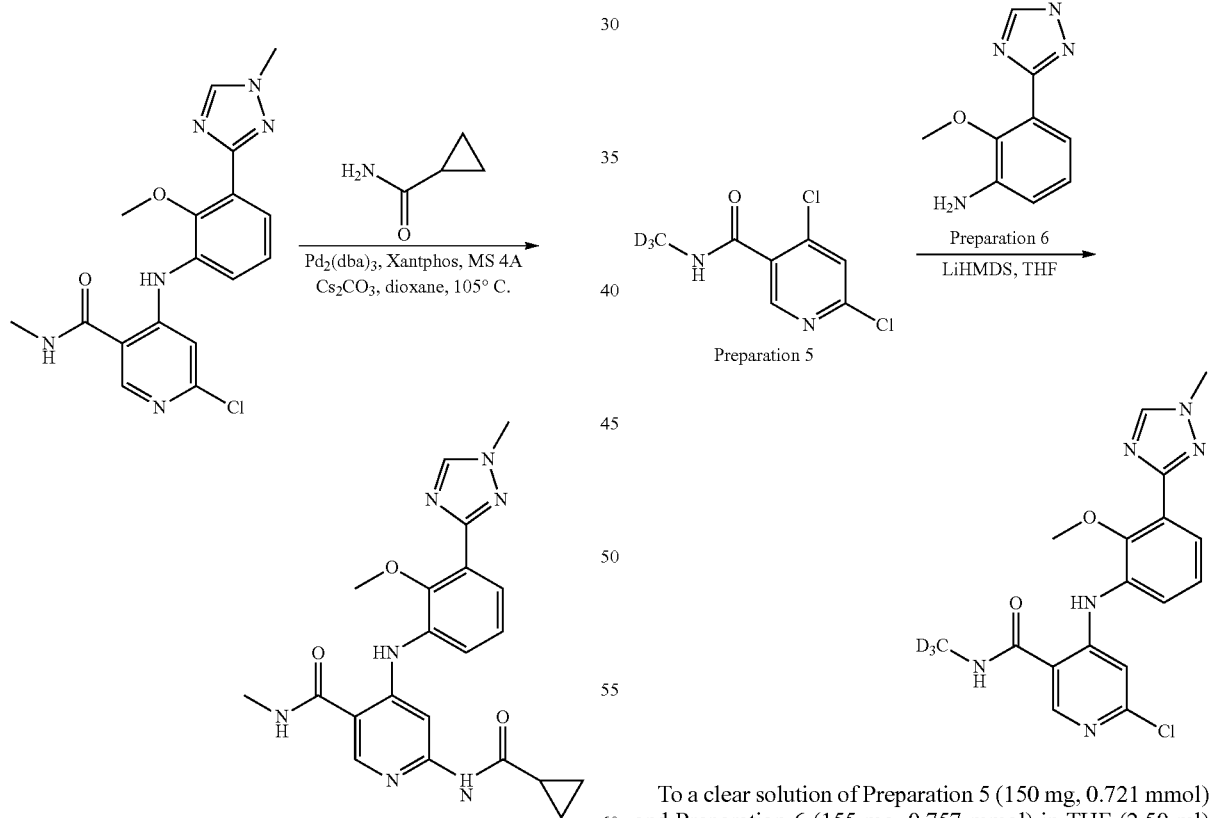

Example 30 was prepared from the product of Step 1 using the conditions previously described in Step 4 of Example 28 to afford Example 30 (8%) as a tan solid. HPLC (method N) RT=2.05 min. LCMS MH+ 422.2. $^1$H NMR (400 MHz, methanol-$d_4$) δ 8.54 (s, 1H), 8.38 (s, 1H), 7.83 (dd, J=7.9, 1.5 Hz, 1H), 7.59 (dd, J=7.9, 1.5 Hz, 1H), 7.38 (t, J=7.9 Hz, 1H), 6.94 (br. s., 1H), 4.06 (d, J=0.4 Hz, 3H), 3.75 (s, 3H), 2.98 (s, 3H), 1.87-1.76 (m, 1H), 1.15-1.07 (m, 2H), 1.06-0.97 (m, 2H).

Example 31

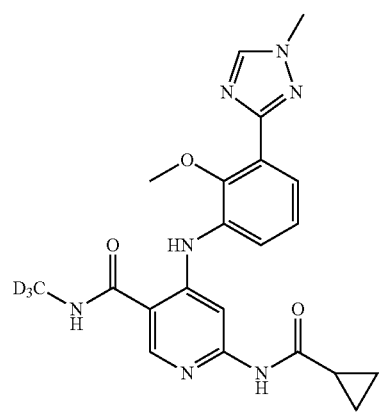 [SMILES: [2H]C([2H])([2H])NC(=O)c1cnc(NC(=O)C2CC2)cc1Nc1cccc(-c2ncn(C)n2)c1OC]

Step 1

To a clear solution of Preparation 5 (150 mg, 0.721 mmol) and Preparation 6 (155 mg, 0.757 mmol) in THF (2.50 ml) was added a 1M solution of lithium bis(trimethylsilyl)amide in THF (2.52 ml, 2.52 mmol) dropwise affording a dark amber colored solution. After stirring at rt for ~40 min., the reaction was cooled in an ice bath and was quenched by addition of aq 1N HCl (2.5 mL). The mixture was then concentrated to remove most of the THF, diluted with 15 mL of water, briefly sonicated then stirred for ~1 h to afford a finely dispersed slurry. The solid was collected by vacuum filtration, rinsed with water, and dried to afford 256 mg (94%) of the desired product as an off-white solid. HPLC (method N) RT=2.65 min. LCMS (m+1)=376.3.

Step 2

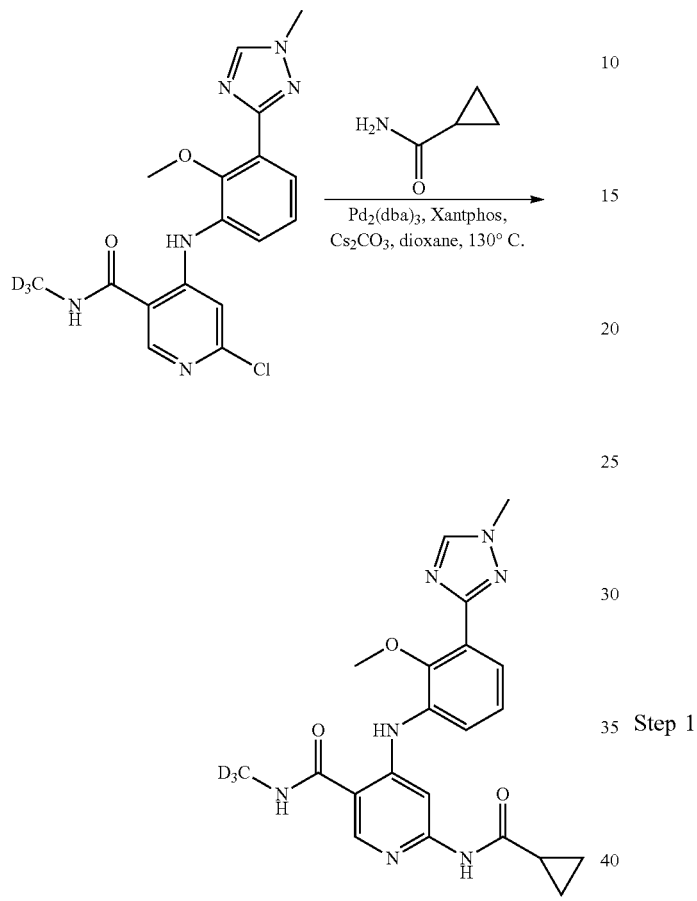

A mixture of the product form Step 1 (30 mg, 0.080 mmol), cyclopropanecarboxamide (13.59 mg, 0.160 mmol), Xantphos (9.24 mg, 0.016 mmol) and cesium carbonate (78 mg, 0.239 mmol) in dioxane (0.8 mL) was sparged with nitrogen for 5 min., then Pd$_2$(dba)$_3$ (7.31 mg, 7.98 μmol) was added and the reaction was placed into a preheated 130° C. heating block for 1 h. Reaction was then cooled and diluted with DMSO and was purified by reverse phase preparative LCMS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 20 minutes, then a 0-minute hold at 100% B; Flow: 20 mL/min. Fractions containing the desired product were combined and dried via centrifugal evaporation. The yield of the product was 26.3 mg (69%). HPLC (Method E) RT=1.09 min. HPLC (Method G) RT=0.89 min. LCMS observed MH+=425.3. $^1$H NMR (500 MHz, DMSO-d$_6$) δ 10.71 (br. s., 1H), 10.61 (br. s., 1H), 8.58 (br. s., 1H), 8.52 (br. s., 1H), 8.48 (br. s., 1H), 8.03 (br. s., 1H), 7.62-7.42 (m, 2H), 7.22 (t, J=7.4 Hz, 1H), 3.93 (br. s., 3H), 3.69 (br. s., 3H), 2.01-1.88 (m, 1H), 0.85-0.69 (m, J=4.4 Hz, 4H).

Example 32 and Example 33

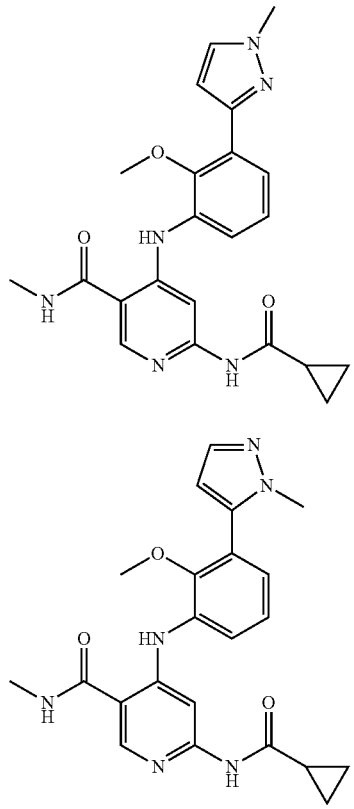

Example 32

Example 33

Step 1

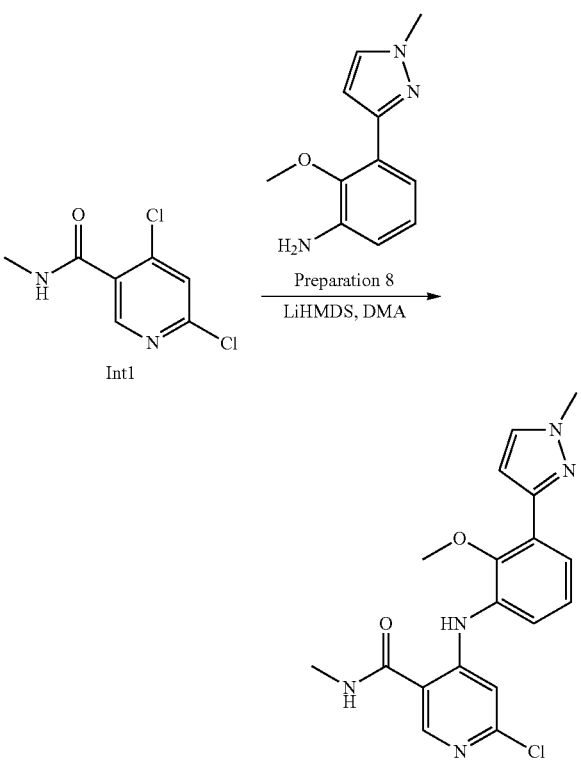

Dissolved 4,6-dichloro-N-methylnicotinamide (Int1, 110 mg, 0.536 mmol) and Preparation 8 as a mixture of regioisomers (120 mg, 0.590 mmol) in DMA (1 mL) and added LiHMDS (1 M in THF) (1.341 mL, 1.341 mmol) dropwise via syringe at rt over ~5 min causing a slight exotherm to form clear dark amber solution. Let reaction stir at rt for 30 min then additional LHMDS (1 M in THF) (0.6 mL, 0.6 mmol) was added. After 30 additional minutes of stirring at rt, the resulting mixture was cooled in an ice bath and water was added to form clear solution. The solution was concentrated under vacuum to remove the volatiles and the resulting aqueous portion was adjusted to a pH of ~4 by adding 1N HCl dropwise causing a solid to precipitate. The resulting slurry was diluted with water to a volume of ~40 mL, stirred for 1 h, and the solid was collected by vacuum filtration and dried to afford the desired product, 6-chloro-4-((2-methoxy-3-(1-methyl-1H-pyrazol-3-yl)phenyl)amino)-N-methylnicotinamide (155 mg, 0.417 mmol, 78% yield) as a tan solid. HPLC analysis (method N) indicated a ~4-5:1 mixture of regioisomers (RT=3.04, major, and 3.12 min, minor). LCMS MH+=372.

Step 2

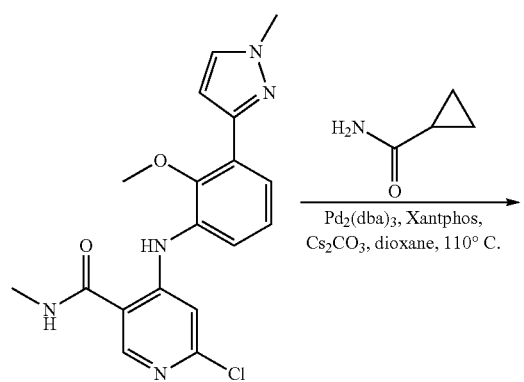

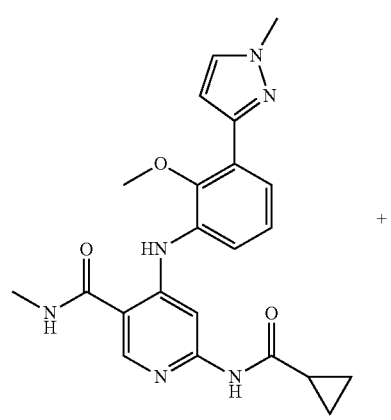

Example 32

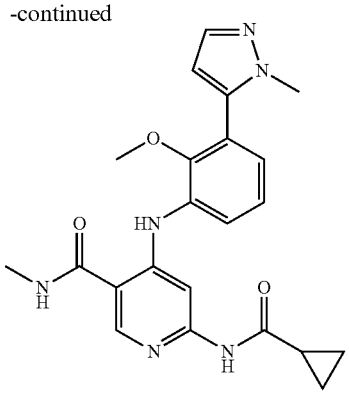

Example 33

The regioisomeric product mixture from Step 1 (25 mg, 0.067 mmol), cyclopropanecarboxamide (11.44 mg, 0.134 mmol), Xantphos (7.78 mg, 0.013 mmol) and cesium carbonate (43.8 mg, 0.134 mmol) in dioxane (0.5 mL) was sparged with nitrogen for 5 min., then $Pd_2(dba)_3$ (12.31 mg, 0.013 mmol) was added and the reaction was placed into a preheated 110° C. heating block. After stirring at this temp for 1 h, the reaction was cooled to rt, diluted with DMSO, and was subjected to purification by reverse phase preparative LCMS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-100% B over 20 minutes, then a 5-minute hold at 100% B; Flow: 20 mL/min.

Fractions containing the major product were combined and dried via centrifugal evaporation to afford 14.9 mg (51%) of Example 32. HPLC (Method E) RT=1.35 min. HPLC (Method G) RT=1.12 min. LCMS observed MH+=421.2. $^1$H NMR (500 MHz, DMSO-$d_6$) δ 10.75 (s, 1H), 10.66 (s, 1H), 8.61 (d, J=4.9 Hz, 1H), 8.50 (s, 1H), 8.06 (s, 1H), 7.76 (d, J=1.8 Hz, 1H), 7.65-7.55 (m, 1H), 7.35 (d, J=7.3 Hz, 1H), 7.16 (t, J=7.9 Hz, 1H), 6.72 (d, J=1.8 Hz, 1H), 3.93-3.85 (m, 3H), 3.58 (s, 3H), 2.79 (d, J=4.3 Hz, 3H), 2.09-1.83 (m, 1H), 0.87-0.67 (m, 4H).

Fractions containing the minor product were combined and dried via centrifugal evaporation to afford 5.3 mg (17%) of Example 33. HPLC (Method E) RT=1.35 min. HPLC (Method G) RT=1.05 min. LCMS observed MH+=421.2. $^1$H NMR (500 MHz, DMSO-$d_6$) δ 10.78 (s, 1H), 10.68 (s, 1H), 8.62 (d, J=4.3 Hz, 1H), 8.51 (s, 1H), 8.04 (s, 1H), 7.57-7.46 (m, 2H), 7.25 (t, J=7.6 Hz, 1H), 7.07 (d, J=7.3 Hz, 1H), 6.37 (d, J=1.8 Hz, 1H), 3.68 (s, 3H), 3.36 (br. s., 3H), 2.78 (d, J=4.3 Hz, 3H), 1.98 (quin, J=6.1 Hz, 1H), 0.83-0.72 (m, 4H).

Example 34 and Example 35

Example 34

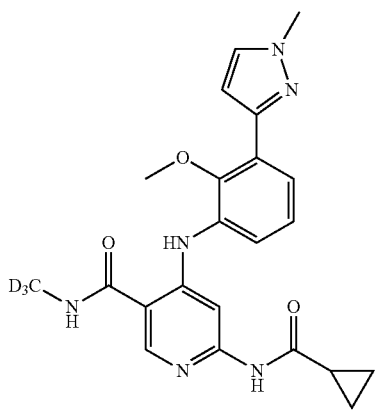

Example 35

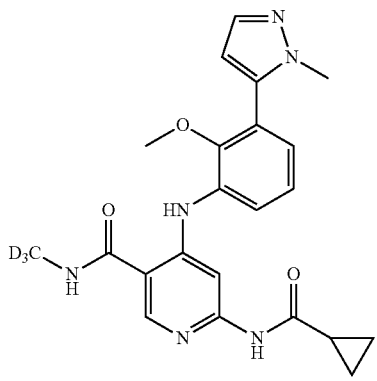

Example 34 and Example 35 were prepared using the procedures described for the preparation of Example 32 and Example 33 and by replacing Int1 with Preparation 5 in Step 1 of the preparation of Example 32 and Example 33. This afforded 3.9 mg (11%) of Example 33. HPLC (Method E) RT=1.30 min. HPLC (Method G) RT=1.07 min. LCMS observed MH+=424.3. $^1$H NMR (500 MHz, DMSO-d$_6$) δ 10.74 (s, 1H), 10.64 (s, 1H), 8.59 (s, 1H), 8.49 (s, 1H), 8.04 (s, 1H), 7.76 (d, J=1.8 Hz, 1H), 7.59 (d, J=6.1 Hz, 1H), 7.35 (d, J=7.3 Hz, 1H), 7.16 (t, J=7.9 Hz, 1H), 6.72 (d, J=2.4 Hz, 1H), 3.90 (s, 3H), 3.58 (s, 3H), 2.02-1.91 (m, 1H), 0.77 (d, J=6.1 Hz, 4H).

Also afforded 10.8 mg (30%) of Example 35. HPLC (Method E) RT=1.35 min. HPLC (Method G) RT=1.04 min. LCMS observed MH+=424.3. $^1$H NMR (500 MHz, DMSO-d$_6$) δ 10.75 (s, 1H), 10.64 (s, 1H), 8.59 (s, 1H), 8.50 (s, 1H), 8.02 (s, 1H), 7.55-7.48 (m, 2H), 7.25 (t, J=7.6 Hz, 1H), 7.07 (d, J=6.7 Hz, 1H), 6.37 (d, J=1.8 Hz, 1H), 3.67 (s, 3H), 3.35 (s, 3H), 2.02-1.91 (m, 1H), 0.82-0.73 (m, 4H).

Example 36

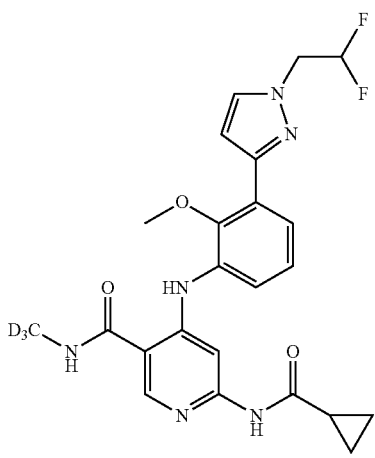 [SMILES: [2H]C([2H])([2H])NC(=O)c1cnc(NC(=O)C2CC2)cc1Nc1cccc(-c2ccn(CC(F)F)n2)c1OC]

Step 1

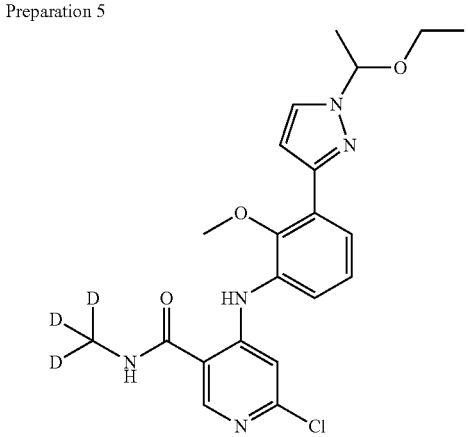

3-(1-(1-Ethoxyethyl)-1H-pyrazol-3-yl)-2-methoxyaniline (Preparation 9, 500 mg, 1.913 mmol) and 4,6-dichloro-N-d$_3$-methylnicotinamide (Preparation 5, 379 mg, 1.822 mmol) were dissolved in THF (10 mL) at rt and the resulting solution was cooled in an ice bath whereupon LiHMDS (1 M in THF, 4.56 mL) was added dropwise via syringe over ~1 min. At this time, the reaction was quenched with a few drops of MeOH and the reaction was concentrated and the resulting solid was purified by silica gel flash chromatography using hexanes/ethyl acetate solvent mixtures as the eluant. Fractions containing the desired product were combined, concentrated, and dried in vacuo to afford 720 mg of a medium brown solid as the desired product. HPLC (method N) RT=2.65 min. LCMS MH+ 433.3/435.3 (observed chloride isotope pattern).

Step 2

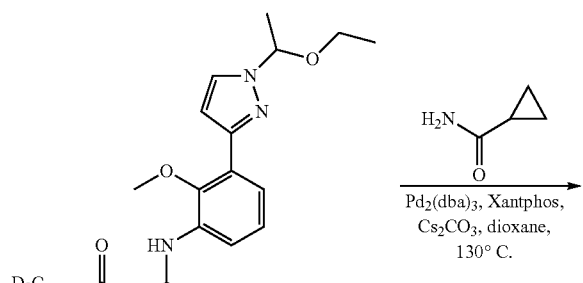

Using the product from Step 1, the above reaction was performed using a similar procedure as described in Step 2 of Example 31. This afforded the desired product in 86% yield as a pale yellow solid. LCMS MH+ 482.4.

Step 3

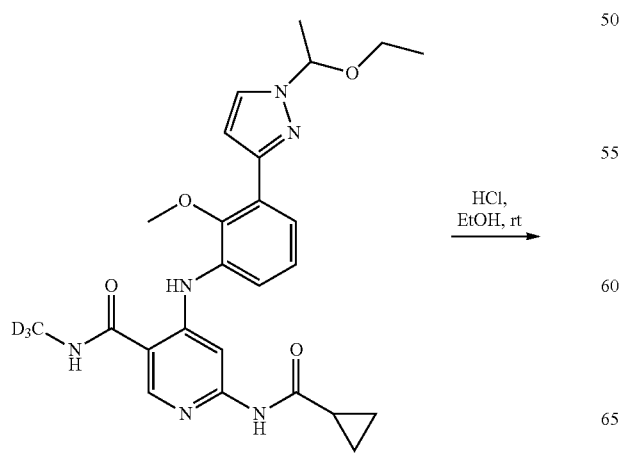

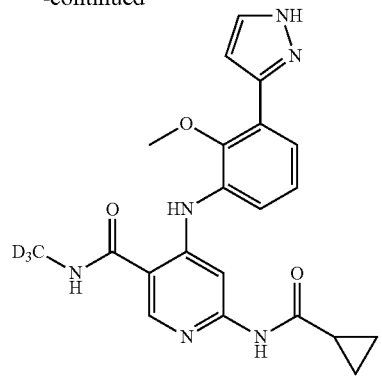

To the product from Step 2 (335 mg, 0.696 mmol) was added EtOH (5 mL) giving a fine slurry. To this mixture at rt was then added HCl (2.5 M in EtOH) (2.78 mL, 6.96 mmol) giving a clear, yellow solution. After stirring at rt for ~3 h total, LCMS analysis showed complete and clean conversion to the more polar product consistent with the desired product. The resulting slurry was concentrated under vacuum to remove most of the EtOH and water (~10 mL) was added followed by a slow dropwise addition of saturated aq sodium bicarbonate with stirring until a pH of ~7 was obtained. Slurry was stirred overnight, then solid was collected by vacuum filtration, rinsed with additional water and air dried in the funnel to obtain a slightly moist filter cake of the solid. This moist solid was transferred to a round bottomed flask and was slurried in MeOH and concentrated and dried under vacuum to yield 251 mg (88%) of an off-white solid as the desired product. HPLC (method N) RT=2.23 min. LCMS MH+ 410.4.

Step 4

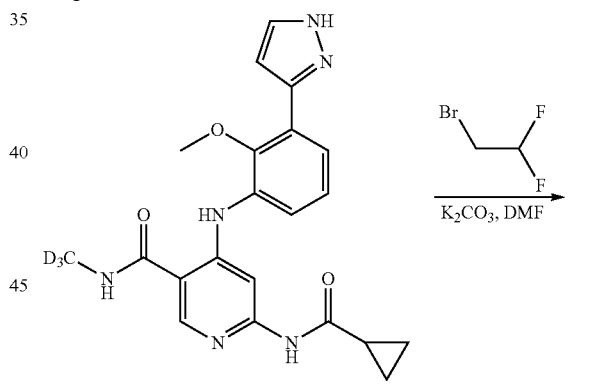

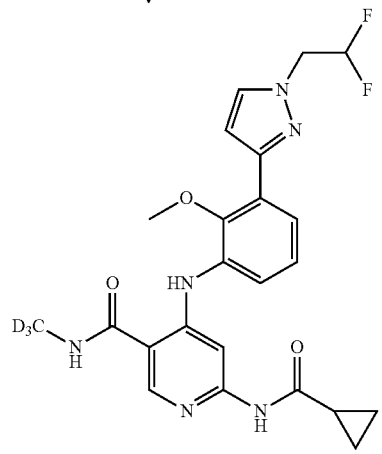

To a mixture of the product from Step 3 (25 mg, 0.061 mmol) and potassium carbonate (25.3 mg, 0.183 mmol) in DMF (0.3 mL) at rt was added 2-bromo-1,1-difluoroethane (13.27 mg, 0.092 mmol) and the mixture was stirred at rt overnight (~16 h). LCMS only showed ~30% conversion at this time, so additional potassium carbonate (25.3 mg, 0.183 mmol) and 2-bromo-1,1-difluoroethane (13.27 mg, 0.092 mmol) was added and the reaction was allowed to continue for an additional 2 h. LCMS at this time indicated mostly converted to product (LCMS observed MH+ 474). Let cool, diluted with DMSO, filtered and was purified using reverse phase preparative LCMS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 15 minutes, then a 5-minute hold at 100% B; Flow: 20 mL/min. Fractions containing the major desired product were combined and dried via centrifugal evaporation. The yield of the product (Example 36) was 13.9 mg (48%). HPLC (Method E) RT=1.52 min. HPLC (Method G) RT=1.27 min. LCMS observed MH+=474.3. $^1$H NMR (500 MHz, DMSO-$d_6$) δ 10.75 (br. s., 1H), 10.65 (s, 1H), 8.60 (s, 1H), 8.49 (s, 1H), 8.01 (br. s., 1H), 7.87 (s, 1H), 7.60 (d, J=7.9 Hz, 1H), 7.38 (d, J=7.3 Hz, 1H), 7.19 (t, J=7.9 Hz, 1H), 6.79 (d, J=1.8 Hz, 1H), 6.55-6.26 (m, 1H), 4.76-4.60 (m, 2H), 3.58 (s, 3H), 2.00-1.91 (m, 1H), 0.77 (d, J=6.1 Hz, 4H).

Example 37 and Example 38

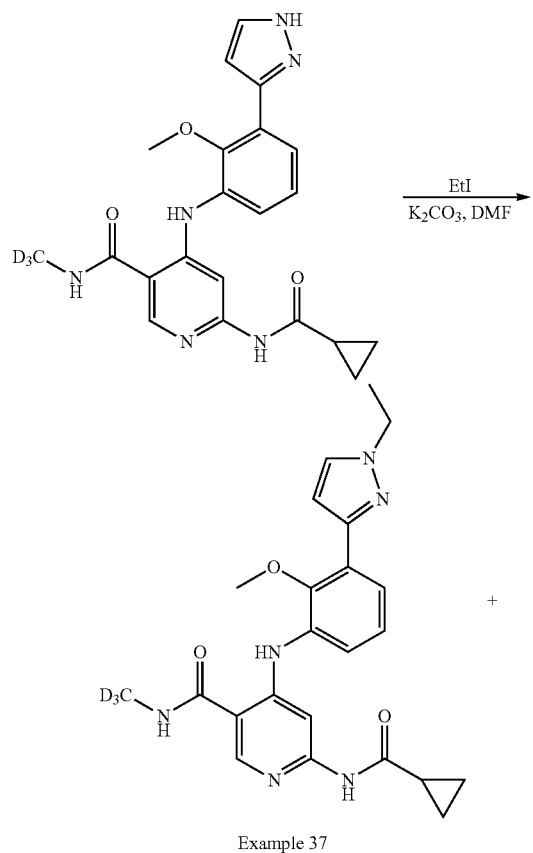

Example 37

+

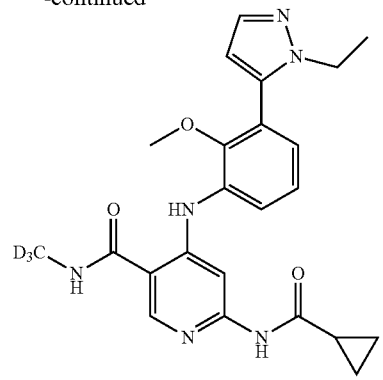

Example 38

Using the product from Step 3 of Example 36, Example 37 and Example 38 were prepared using a similar procedure as described in Step 4 of Example 36 and by replacing 2-bromo-1,1-difluoroethane with iodoethane as the alkylating reagent. This afforded 13.5 mg (51%) of Example 37 and 8.2 mg (31%) of Example 38.

Example 37

HPLC (Method E) RT=1.45 min. HPLC (Method G) RT=1.20 min. LCMS observed MH+=438.3. $^1$H NMR (500 MHz, DMSO-$d_6$) δ 11.65-11.27 (m, 1H), 11.08-10.78 (m, 1H), 9.08-8.75 (m, 1H), 8.63-8.23 (m, 1H), 7.82 (d, J=1.8 Hz, 1H), 7.76 (d, J=7.3 Hz, 1H), 7.37 (d, J=7.9 Hz, 1H), 7.31-7.21 (m, 2H), 6.72 (d, J=2.4 Hz, 1H), 4.19 (q, J=7.3 Hz, 2H), 3.60 (br. s., 3H), 1.92-1.80 (m, 1H), 1.42 (t, J=7.3 Hz, 3H), 0.98-0.78 (m, 4H).

Example 38

HPLC (Method E) RT=1.44 min. HPLC (Method G) RT=1.13 min. LCMS observed MH+=438.3. $^1$H NMR (500 MHz, DMSO-$d_6$) δ 11.25 (br. s., 1H), 10.82 (s, 1H), 8.79 (s, 1H), 8.46 (s, 1H), 7.58-7.45 (m, 3H), 7.30 (t, J=7.6 Hz, 1H), 7.21-7.11 (m, 1H), 6.35 (s, 1H), 3.95 (q, J=6.9 Hz, 2H), 3.37 (s, 3H), 1.91 (d, J=4.3 Hz, 1H), 1.25 (t, J=7.3 Hz, 3H), 0.96-0.76 (m, 4H).

Example 39

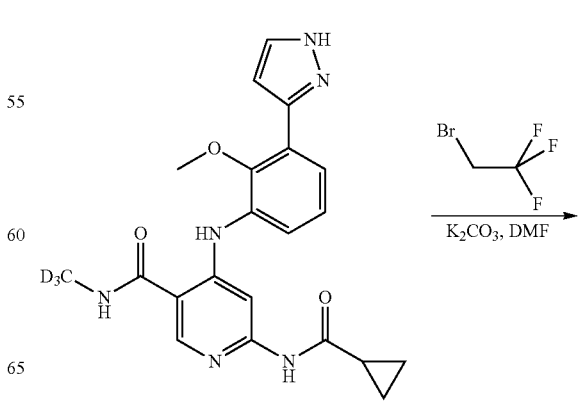

-continued

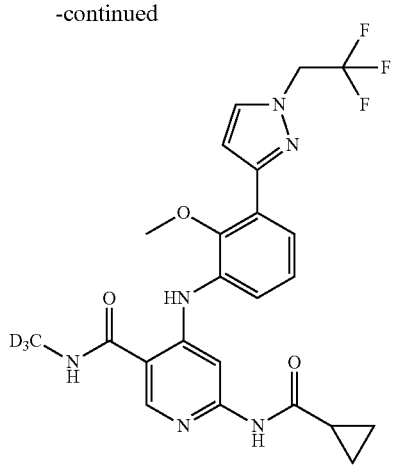

Using the product from Step 3 of Example 36, Example 39 was prepared using a similar procedure as described in Step 4 of Example 36 and by replacing 2-bromo-1,1-difluoroethane with 2-bromo-1,1,1-trifluoroethane as the alkylating reagent. This afforded 5.2 mg (17%) of Example 39. HPLC (Method E) RT=1.58 min. HPLC (Method G) RT=1.38 min. LCMS observed MH+=492.3. $^1$H NMR (500 MHz, DMSO-$d_6$) δ 10.75 (s, 1H), 10.67 (s, 1H), 8.59 (s, 1H), 8.51 (s, 1H), 8.06 (s, 1H), 7.94 (d, J=1.8 Hz, 1H), 7.57 (dd, J=7.9, 1.2 Hz, 1H), 7.40 (d, J=6.7 Hz, 1H), 7.20 (t, J=7.9 Hz, 1H), 6.84 (d, J=1.8 Hz, 1H), 5.20 (q, J=9.2 Hz, 2H), 3.59 (s, 3H), 2.03-1.90 (m, 1H), 0.88-0.69 (m, 4H).

Example 40

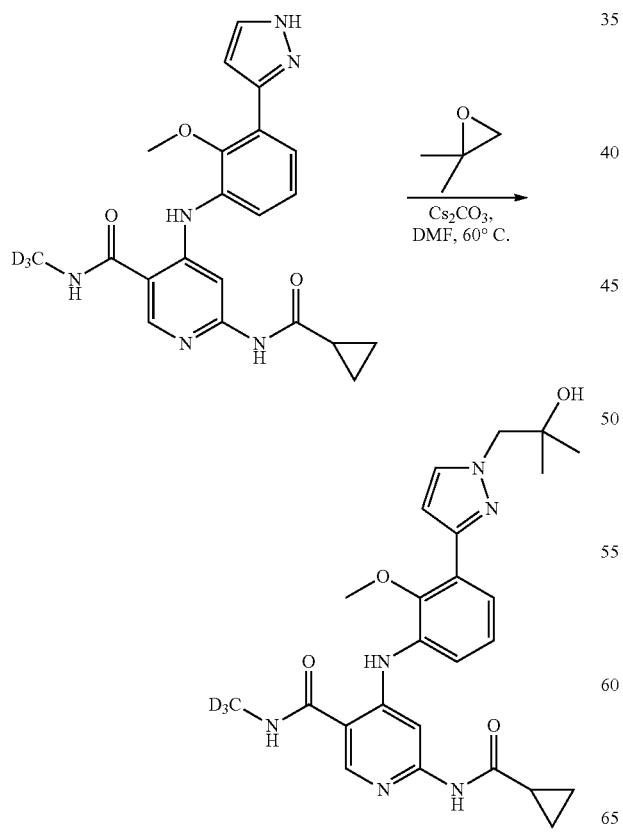

The product from Step 4 of Example 36 (20 mg, 0.049 mmol) and cesium carbonate (47.7 mg, 0.147 mmol) was mixed in DMF (0.2 mL) and 2,2-dimethyloxirane (7.04 mg, 0.098 mmol) was added followed by heating the resulting mixture at 60° C. overnight (~16 h). The reaction was cooled and was subjected directly to purification by reverse phase preparative LCMS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 19 minutes, then a 5-minute hold at 100% B; Flow: 20 mL/min. Fractions containing the desired product were combined and dried via centrifugal evaporation. The yield of the product (Example 40) was 13.3 mg (56%). HPLC (Method E) RT=1.32 min. HPLC (Method G) RT=1.11 min. LCMS observed MH+=482.3. $^1$H NMR (500 MHz, DMSO-$d_6$) δ 10.72 (br. s., 1H), 10.63 (br. s., 1H), 8.58 (s, 1H), 8.49 (s, 1H), 8.04 (s, 1H), 7.74 (s, 1H), 7.56 (d, J=7.9 Hz, 1H), 7.35 (d, J=7.9 Hz, 1H), 7.17 (t, J=7.6 Hz, 1H), 6.71 (s, 1H), 4.81 (br. s., 1H), 4.07 (s, 2H), 3.57 (s, 3H), 2.04-1.84 (m, 1H), 1.09 (s, 6H), 0.77 (d, J=6.1 Hz, 4H).

Example 41

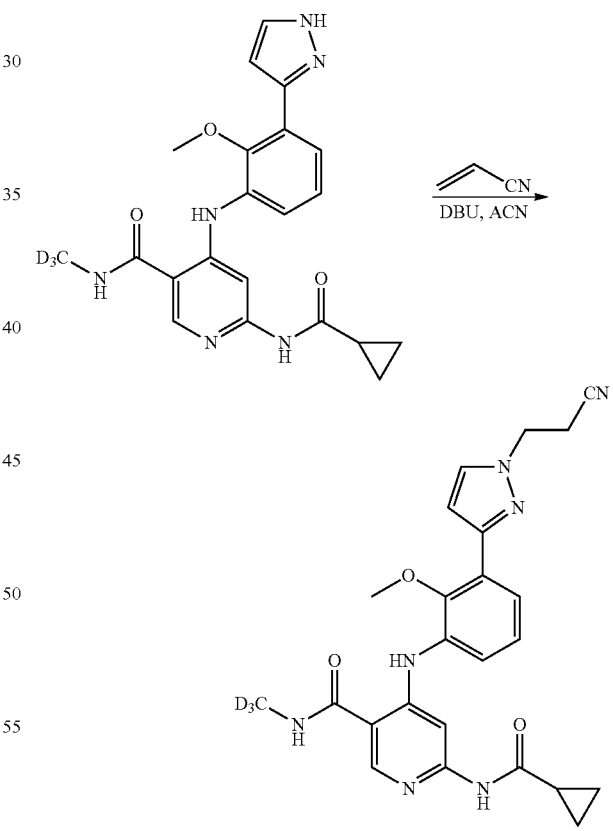

The product from Step 4 of Example 36 (20 mg, 0.049 mmol) was mixed in acetonitrile (0.2 mL) to give a slurry and DBU (8.10 μl, 0.054 mmol) was added followed by acrylonitrile (2.236 μl, 0.059 mmol) and the resulting slurry was stirred at rt for ~1 h then warmed to 60° C. overnight (~15 h). The reaction was cooled and was subjected directly to purification by reverse phase preparative LCMS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 0-100% B over 19 minutes, then a 5-minute hold at 100% B; Flow: 20 mL/min. Fractions containing the desired product were combined and dried via centrifugal evaporation. The yield of the product (Example 40) was 14.6 mg (65%). HPLC (Method E) RT=1.33 min. HPLC (Method G) RT=1.11 min. LCMS observed MH+=463.2. $^1$H NMR (500 MHz, DMSO-$d_6$) δ 10.74 (s, 1H), 10.66 (s, 1H), 8.59 (s, 1H), 8.50 (s, 1H), 8.04 (s, 1H), 7.89 (d, J=1.8 Hz, 1H), 7.60 (d, J=7.3 Hz, 1H), 7.38 (d, J=7.9 Hz, 1H), 7.19 (t, J=7.6 Hz, 1H), 6.76 (d, J=1.8 Hz, 1H), 4.46 (t, J=6.4 Hz, 2H), 3.59 (s, 3H), 3.11 (t, J=6.4 Hz, 2H), 2.05-1.92 (m, 1H), 0.77 (d, J=5.5 Hz, 4H).

Example 42

Step 1

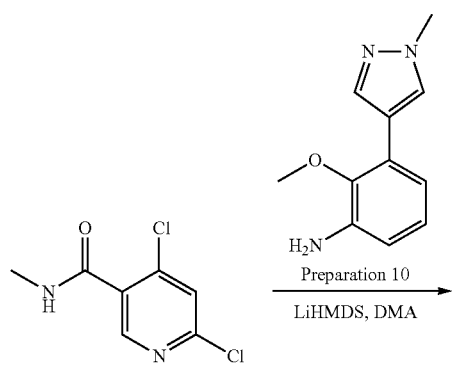

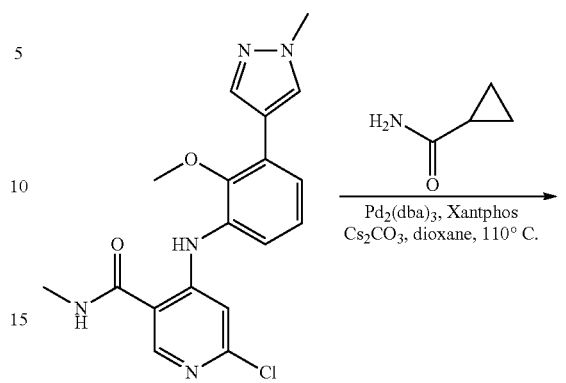

Step 2

Step 1 was performed using the procedure as described in Step 1 of the preparation of Example 32 and Example 33 to afford an 82% yield of the desired product as a tan solid. HPLC (method N) RT=3.04 min. LCMS MH+ 372.

Step 2 was performed using the procedure as described in Step 2 of the preparation of Example 32 and Example 33 to afford a 79% yield of the desired product (Example 42). HPLC (Method E) RT=1.33 min. HPLC (Method G) RT=1.08 min. LCMS observed MH+=421.2. $^1$H NMR (500 MHz, DMSO-$d_6$) δ 10.74 (s, 1H), 10.64 (s, 1H), 8.61 (d, J=4.3 Hz, 1H), 8.50 (s, 1H), 8.15 (s, 1H), 8.04 (s, 1H), 7.90 (s, 1H), 7.34 (d, J=6.7 Hz, 1H), 7.26 (d, J=7.3 Hz, 1H), 7.18-7.10 (m, 1H), 3.89 (s, 3H), 3.58 (s, 3H), 2.79 (d, J=4.3 Hz, 3H), 2.02-1.93 (m, 1H), 0.77 (d, J=6.1 Hz, 4H).

Example 43

Step 1

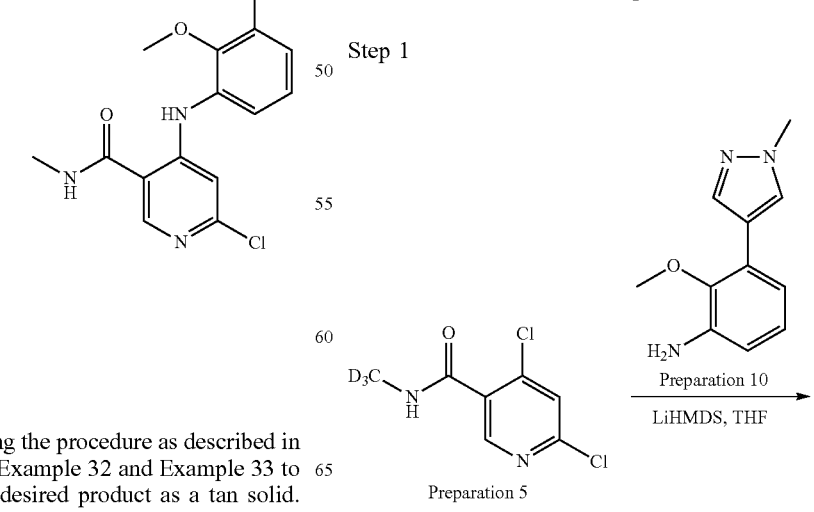

-continued

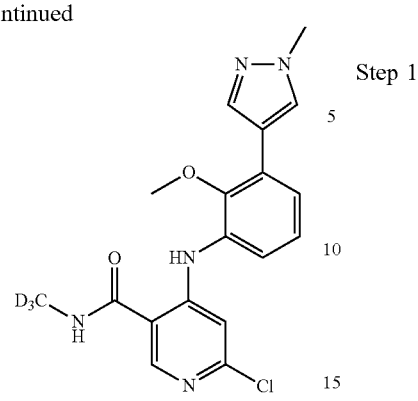

Step 1 was performed using the procedure as described in Step 1 of the preparation of Example 32 and Example 33 to afford an 81% yield of the desired product as a pale yellow solid. LCMS MH+ 375.

Step 2

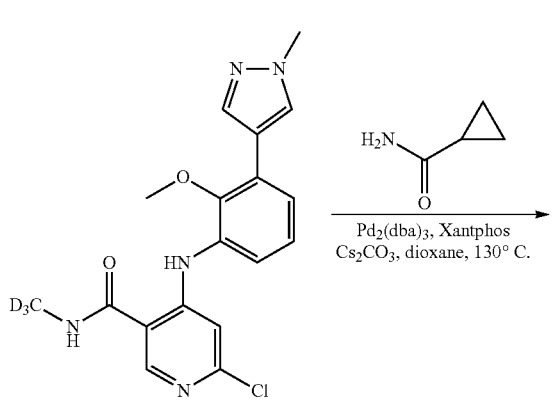

Step 2 was performed using the procedure as described in Step 2 of the preparation of Example 31 to afford a 67% yield of the desired product (Example 43). HPLC (Method E) RT=1.35 min. HPLC (Method G) RT=1.03 min. LCMS observed MH+=424.3. $^1$H NMR (500 MHz, DMSO-d$_6$) δ 10.73 (s, 1H), 10.02 (s, 1H), 8.54 (s, 1H), 8.50 (s, 1H), 8.16 (s, 1H), 8.13 (br. s., 1H), 7.91 (s, 1H), 7.44 (d, J=7.9 Hz, 1H), 7.36 (d, J=7.9 Hz, 1H), 7.18 (t, J=7.9 Hz, 1H), 7.05 (br. s., 1H), 3.89 (s, 3H), 3.60 (s, 3H), 2.37 (s, 3H), 2.27 (s, 3H).

Example 44

Step 1

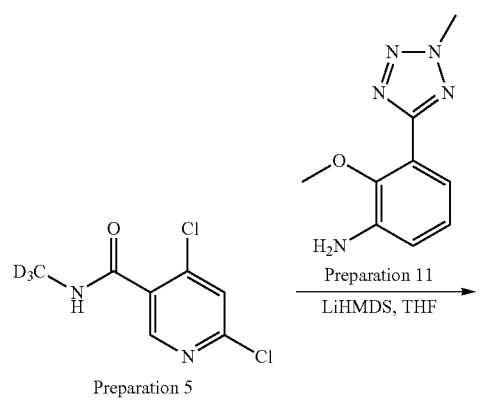

Step 1 was performed using the procedure as described in Step 1 of the preparation of Example 32 and Example 33 to afford an 84% yield of the desired product as a medium brown solid. HPLC (method N) RT=2.88 min. LCMS MH+ 377.3.

Step 2

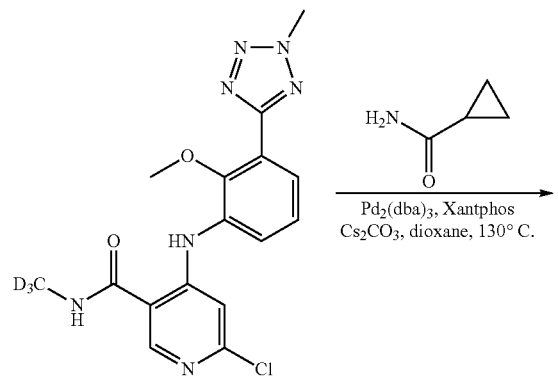

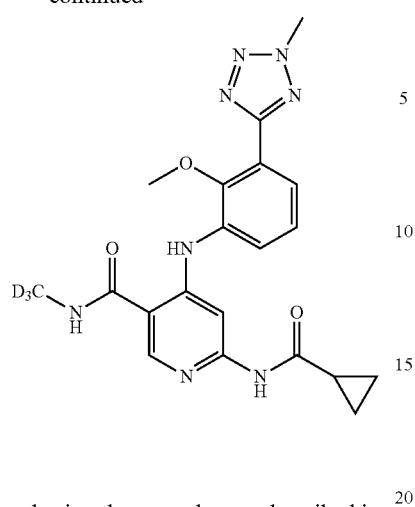

Step 1 was performed using the procedure as described in Step 2 of the preparation of Example 31 to afford a 69% yield of the desired product (Example 44). HPLC (Method E) RT=1.31 min. HPLC (Method G) RT=1.16 min. LCMS observed MH+=426.3. ¹H NMR (500 MHz, DMSO-$d_6$) δ 10.78 (br. s., 1H), 10.72 (br. s., 1H), 8.61 (br. s., 1H), 8.52 (s, 1H), 8.06 (s, 1H), 7.60 (d, J=7.4 Hz, 2H), 7.32 (t, J=7.7 Hz, 1H), 4.45 (s, 3H), 3.73 (s, 3H), 1.97 (br. s., 1H), 0.77 (d, J=5.0 Hz, 4H).

Example 45

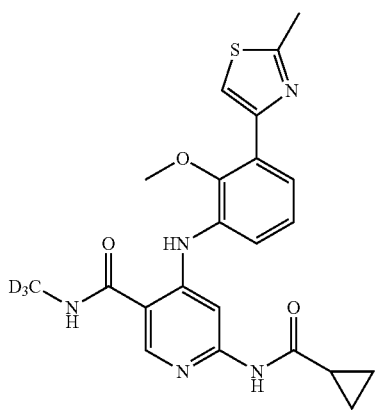 [SMILES: [2H]C([2H])([2H])NC(=O)c1cnc(NC(=O)C2CC2)cc1Nc1cccc(-c2csc(C)n2)c1OC]

Step 1

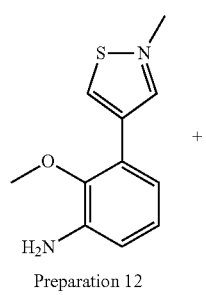

Preparation 12

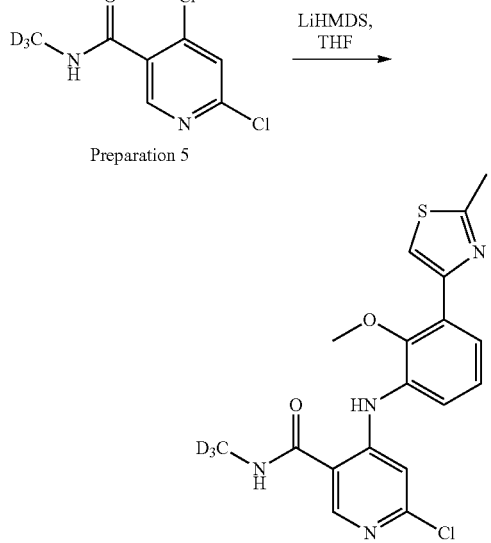

Step 1 was performed using the procedure as described in Step 1 of the preparation of Example 32 and Example 33 to afford an 81% yield of the desired product as an off-white solid. LCMS MH+ 392.1.

Step 2

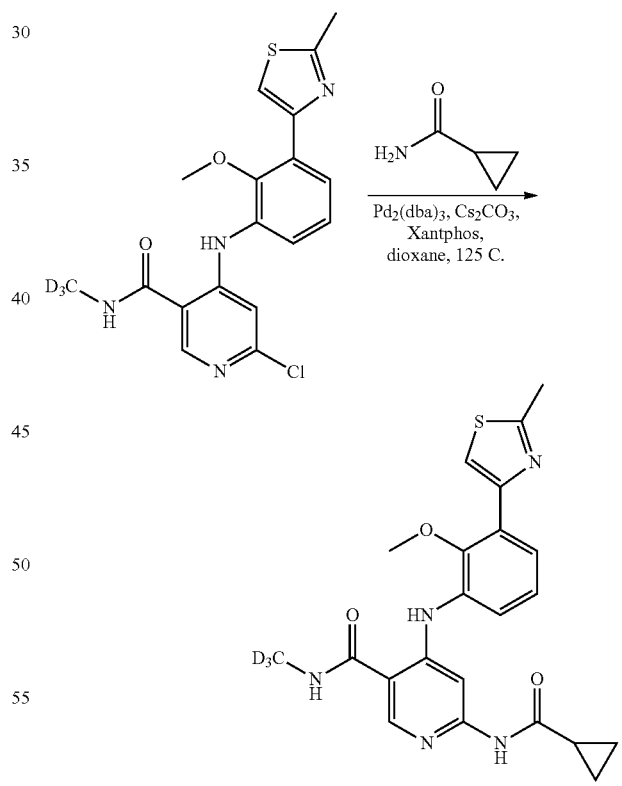

Step 2 was performed using the procedure as described in Step 2 of the preparation of Example 31 to afford a 67% yield of the desired product (Example 45). HPLC (Method E) RT=1.63 min. HPLC (Method G) RT=1.27 min. LCMS observed MH+=441.3. ¹H NMR (500 MHz, DMSO-$d_6$) δ 10.87 (br. s., 1H), 10.73 (s, 1H), 8.66 (br. s., 1H), 8.51 (s, 1H), 7.98 (s, 1H), 7.92 (br. s., 1H), 7.83 (d, J=7.4 Hz, 1H), 7.41 (d, J=7.1 Hz, 1H), 7.25 (t, J=7.9 Hz, 1H), 3.64 (s, 3H), 2.73 (s, 3H), 1.99-1.92 (m, 1H), 0.80 (d, J=5.7 Hz, 4H).

Example 46

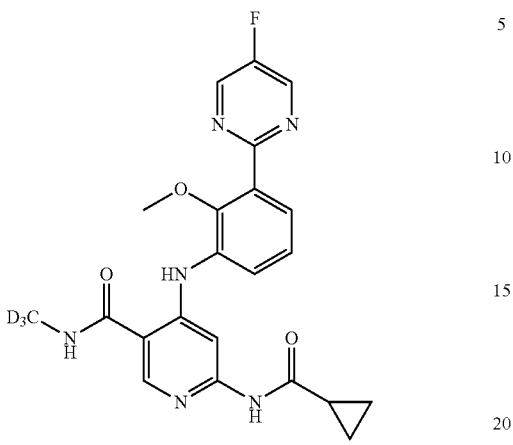

Example 46 was prepared utilizing the procedure from Preparation 12 (using 2-chloro-5-fluoropyrimidine instead of 4-bromo-2-methylthiazole in Step 4) and procedure outlined for Example 45. $^1$H NMR (400 MHz, DMSO-d$_6$) δ 10.78 (br. s., 1H), 10.66 (s, 1H), 9.03 (d, J=0.9 Hz, 1H), 8.59 (s, 1H), 8.52 (s, 1H), 8.14-7.93 (m, 1H), 7.56 (dd, J=7.9, 1.5 Hz, 1H), 7.43 (dd, J=7.7, 1.3 Hz, 1H), 7.33-7.20 (m, 1H), 3.67 (s, 3H), 2.08-1.88 (m, 1H), 0.83-0.72 (m, 4H). LC retention time 0.68 min [J]. MS (E+) m/z: 440 (MH$^+$).

| Compound | $^1$H NMR (methanol-d$_4$ equates CDCl$_3$:MeOD ~1:1 unless otherwise noted) |
|---|---|
| 2 | $^1$H NMR (500 MHz, DMSO-d$_6$) δ 10.84 (s, 1H), 10.54 (s, 1H), 8.61 (d, J = 4.5 Hz, 1H), 8.57 (s, 1H), 7.98 (s, 1H), 7.94 (dd, J = 7.9, 1.5 Hz, 1H), 7.75-7.67 (m, 1H), 7.67-7.61 (m, 1H), 7.43-7.34 (m, 1H), 3.15 (s, 3H), 2.77 (d, J = 4.5 Hz, 3H), 2.02 (s, 3H) |
| 3 | $^1$H NMR (500 MHz, DMSO-d$_6$) δ 10.89 (s, 1H), 9.83 (s, 1H), 8.65 (d, J = 5.0 Hz, 1H), 8.58 (s, 1H), 7.98-7.89 (m, 2H), 7.78-7.70 (m, 1H), 7.69-7.64 (m, 1H), 7.40 (t, J = 7.4 Hz, 1H), 4.41 (dd, J = 8.2, 5.7 Hz, 1H), 3.95-3.85 (m, 1H), 3.82-3.74 (m, 1H), 3.16 (s, 3H), 2.78 (d, J = 4.5 Hz, 3H), 2.21-2.09 (m, 1H), 1.94-1.75 (m, 3H) |
| 4 | $^1$H NMR (500 MHz, DMSO-d$_6$) δ 10.87 (s, 1H), 10.52 (s, 1H), 8.65-8.59 (m, 1H), 8.57 (s, 1H), 7.98 (s, 1H), 7.94 (dd, J = 7.9, 1.5 Hz, 1H), 7.78-7.69 (m, 1H), 7.66 (d, J = 7.9 Hz, 1H), 7.39 (t, J = 7.2 Hz, 1H), 3.85 (dd, J = 11.4, 2.5 Hz, 2H), 3.27 (td, J = 11.6, 2.0 Hz, 2H), 3.15 (s, 3H), 2.77 (d, J = 4.5 Hz, 3H), 2.74-2.66 (m, 1H), 1.68-1.60 (m, 2H), 1.60-1.44 (m, 2H) |
| 5 | $^1$H NMR (500 MHz, DMSO-d$_6$) δ 10.86 (s, 1H), 10.41 (s, 1H), 8.61 (d, J = 4.5 Hz, 1H), 8.56 (s, 1H), 7.99 (s, 1H), 7.94 (dd, J = 7.9, 1.5 Hz, 1H), 7.79-7.71 (m, 1H), 7.66 (d, J = 8.4 Hz, 1H), 7.39 (t, J = 7.7 Hz, 1H), 3.15 (s, 3H), 2.77 (d, J = 4.5 Hz, 3H), 2.44 (t, J = 11.4 Hz, 1H), 1.71 (t, J = 13.1 Hz, 4H), 1.61 (d, J = 11.9 Hz, 1H), 1.37-1.05 (m, 5H) |
| 6 | $^1$H NMR (500 MHz, DMSO-d$_6$) δ 10.85 (s, 1H), 10.78 (s, 1H), 8.63 (q, J = 4.3 Hz, 1H), 8.59 (s, 1H), 7.95 (s, 1H), 7.91 (dd, J = 7.9, 1.5 Hz, 1H), 7.73-7.67 (m, 1H), 7.64-7.60 (m, 1H), 7.39-7.33 (m, 1H), 7.31-7.24 (m, 4H), 7.24-7.18 (m, 1H), 3.66 (s, 2H), 3.12 (s, 3H), 2.77 (d, J = 5.0 Hz, 3H) |
| 7 | $^1$H NMR (500 MHz, DMSO-d$_6$) δ 10.86 (br. s., 1H), 10.47 (br. s., 1H), 8.62 (br. s., 1H), 8.57 (s, 1H), 7.99 (s, 1H), 7.94 (d, J = 7.9 Hz, 1H), 7.80-7.71 (m, 1H), 7.66 (d, J = 7.4 Hz, 1H), 7.39 (t, J = 7.2 Hz, 1H), 3.15 (s, 3H), 2.77 (br. s., 3H), 2.73-2.62 (m, 1H), 1.01 (dd, J = 6.7, 2.2 Hz, 6H) |
| 8 | $^1$H NMR (500 MHz, DMSO-d$_6$) δ 10.85 (s, 1H), 10.66 (s, 1H), 8.61 (d, J = 4.5 Hz, 1H), 8.56 (s, 1H), 7.97 (s, 1H), 7.93 (dd, J = 7.9, 1.0 Hz, 1H), 7.74-7.69 (m, 1H), 7.66-7.62 (m, 1H), 7.37 (t, J = 7.4 Hz, 1H), 3.16 (s, 3H), 2.77 (d, J = 4.5 Hz, 3H), 1.84 (dd, J = 7.7, 5.7 Hz, 1H), 1.11 (s, 3H), 1.06 (s, 3H), 0.94-0.88 (m, 1H), 0.76 (dd, J = 7.9, 4.0 Hz, 1H) |
| 9 | $^1$H NMR (500 MHz, DMSO-d$_6$) δ 10.88 (d, J = 3.5 Hz, 1H), 10.79 (d, J = 3.5 Hz, 1H), 8.69-8.56 (m, 2H), 7.97 (d, J = 4.0 Hz, 1H), 7.90 (dd, J = 7.9, 3.5 Hz, 1H), 7.72-7.66 (m, 1H), 7.66-7.60 (m, 1H), 7.33 (td, J = 7.6, 3.7 Hz, 1H), 7.13-7.00 (m, 4H), 4.02 (br. s., 1H), 3.14 (d, J = 3.5 Hz, 3H), 2.78 (t, J = 4.0 Hz, 3H), 2.73-2.61 (m, 2H), 2.01-1.85 (m, 3H), 1.58 (d, J = 5.0 Hz, 1H) |

| Compound | ¹H NMR (methanol-d₄ equates CDCl₃:MeOD ~1:1 unless otherwise noted) |
| --- | --- |
| 10 | ¹H NMR (500 MHz, DMSO-d₆) δ 10.84 (d, J = 3.5 Hz, 1H), 10.79 (d, J = 3.5 Hz, 1H), 8.67-8.61 (m, 1H), 8.59 (d, J = 4.5 Hz, 1H), 8.48-8.42 (m, 1H), 7.95 (d, J = 4.0 Hz, 1H), 7.91 (dd, J = 7.9, 3.0 Hz, 1H), 7.75-7.65 (m, 2H), 7.64-7.59 (m, 1H), 7.41-7.28 (m, 2H), 7.27-7.20 (m, 1H), 3.88 (d, J = 4.0 Hz, 2H), 3.13 (d, J = 4.5 Hz, 3H), 2.78 (t, J = 4.2 Hz, 3H) |
| 11 | ¹H NMR (500 MHz, DMSO-d₆) δ 10.92 (br. s., 1H), 10.65 (br. s., 1H), 8.70 (br. s., 1H), 8.54 (d, J = 3.5 Hz, 1H), 7.96 (d, J = 7.9 Hz, 1H), 7.75 (d, J = 7.4 Hz, 2H), 7.66 (d, J = 8.4 Hz, 1H), 7.44 (t, J = 7.4 Hz, 1H), 3.17 (d, J = 3.5 Hz, 3H), 2.83-2.74 (m, 3H), 2.36-2.27 (m, 2H), 1.60-1.42 (m, 2H), 0.85 (td, J = 7.4, 3.5 Hz, 3H) |
| 12 | ¹H NMR (500 MHz, DMSO-d₆) δ 10.85 (d, J = 4.0 Hz, 1H), 10.71 (d, J = 3.5 Hz, 1H), 8.62 (t, J = 4.5 Hz, 1H), 8.58 (d, J = 4.5 Hz, 1H), 8.00-7.87 (m, 2H), 7.74-7.66 (m, 1H), 7.65-7.59 (m, 1H), 7.36 (td, J = 7.4, 3.5 Hz, 1H), 7.23-7.16 (m, 2H), 6.89-6.82 (m, 2H), 3.70 (d, J = 4.5 Hz, 2H), 3.57 (d, J = 4.0 Hz, 2H), 3.12 (d, J = 4.0 Hz, 3H), 2.77 (t, J = 4.5 Hz, 3H) |
| 13 | ¹H NMR (500 MHz, DMSO-d₆) δ 10.87 (s, 1H), 10.50 (s, 1H), 8.62 (q, J = 4.5 Hz, 1H), 8.57 (s, 1H), 8.04 (s, 1H), 7.94 (dd, J = 7.9, 1.5 Hz, 1H), 7.78-7.72 (m, 1H), 7.70-7.64 (m, 1H), 7.42-7.34 (m, 1H), 3.17 (s, 3H), 2.78 (d, J = 4.5 Hz, 3H), 2.43-2.33 (m, 1H), 1.54-1.41 (m, 2H), 1.37 (ddd, J = 13.3, 7.6, 5.4 Hz, 2H), 0.79 (t, J = 7.4 Hz, 6H) |
| 14 | ¹H NMR (500 MHz, DMSO-d₆) δ 10.85 (d, J = 3.0 Hz, 1H), 10.35 (d, J = 3.0 Hz, 1H), 8.61 (d, J = 4.0 Hz, 1H), 8.56 (d, J = 4.0 Hz, 1H), 8.01 (d, J = 3.5 Hz, 1H), 7.95 (dd, J = 7.9, 3.0 Hz, 1H), 7.81-7.71 (m, 1H), 7.71-7.63 (m, 1H), 7.40 (td, J = 7.7, 3.5 Hz, 1H), 3.32-3.26 (m, 1H), 3.15 (d, J = 3.5 Hz, 3H), 2.77 (t, J = 3.7 Hz, 3H), 2.20-2.09 (m, 2H), 2.08-1.97 (m, 2H), 1.93-1.81 (m, 1H), 1.78-1.66 (m, 1H) |
| 15 | ¹H NMR (500 MHz, DMSO-d₆) δ 10.88 (s, 1H), 10.79 (s, 1H), 8.65 (d, J = 4.5 Hz, 1H), 8.57 (s, 1H), 7.77 (s, 1H), 7.73-7.55 (m, 3H), 3.19 (s, 3H), 2.77 (d, J = 4.5 Hz, 3H), 2.00-1.89 (m, 1H), 0.83-0.69 (m, 4H) |
| 16 | ¹H NMR (500 MHz, DMSO-d₆) δ 9.37 (s, 1H), 8.79 (s, 1H), 8.11 (s, 1H), 7.68 (d, J = 1.5 Hz, 1H), 7.47 (s, 1H), 6.46 (d, J = 2.0 Hz, 1H), 4.53 (quin, J = 7.6 Hz, 1H), 4.43-4.32 (m, 1H), 4.12 (t, J = 7.9 Hz, 1H), 4.01 (t, J = 7.7 Hz, 1H), 3.93-3.83 (m, 1H), 2.76 (s, 3H), 2.16-2.03 (m, 2H), 0.60 (d, J = 5.9 Hz, 1H), 0.47 (br. s., 1H) |
| 17 | ¹H NMR (500 MHz, methanol-d₄) δ 8.38 (s, 1H), 8.05-8.00 (m, 1H), 7.71-7.66 (m, 2H), 7.34 (ddd, J = 8.2, 5.7, 2.5 Hz, 1H), 7.02 (s, 1H), 3.12 (s, 3H), 2.93 (s, 3H), 2.85 (s, 3H) |
| 18 | ¹H NMR (500 MHz, DMSO-d₆) δ 10.85 (d, J = 2.5 Hz, 1H), 8.61-8.55 (m, 1H), 8.53 (s, 1H), 8.00 (s, 1H), 7.65 (td, J = 8.3, 6.2 Hz, 1H), 7.41 (d, J = 8.4 Hz, 1H), 7.13 (dd, J = 10.7, 8.7 Hz, 1H), 3.33 (s, 3H), 2.76 (d, J = 4.5 Hz, 3H), 2.03-1.91 (m, 1H), 0.82-0.71 (m, 4H) |
| 19 | ¹H NMR (500 MHz, methanol-d₄) δ 8.26 (s, 1H), 7.77 (s, 1H), 7.48 (dd, J = 7.9, 1.5 Hz, 1H), 7.39 (dd, J = 7.9, 1.0 Hz, 1H), 7.28 (td, J = 7.7, 1.5 Hz, 1H), 7.12 (td, J = 7.7, 1.5 Hz, 1H), 2.91 (s, 3H), 1.79-1.70 (m, 1H), 1.60 (s, 6H), 0.97-0.92 (m, 2H), 0.89-0.81 (m, 2H) |
| 20 | ¹H NMR (500 MHz, methanol-d₄) δ 8.47 (s, 1H), 8.17 (s, 1H), 8.02 (dd, J = 8.9, 5.9 Hz, 1H), 7.42 (dd, J = 10.4, 2.0 Hz, 1H), 7.05-6.95 (m, 1H), 3.12 (s, 3H), 2.93 (s, 3H), 1.90-1.75 (m, 1H), 1.06-0.96 (m, 2H), 0.94-0.83 (m, 2H) |
| 21 | ¹H NMR (500 MHz, methanol-d₄) δ 8.44 (s, 1H), 8.09 (s, 1H), 8.04-8.00 (m, 1H), 7.73-7.67 (m, 2H), 7.33 (ddd, J = 8.2, 5.9, 2.2 Hz, 1H), 3.12 (s, 3H), 2.94 (s, 3H), 2.81-2.67 (m, 1H), 2.15-2.03 (m, 1H), 1.85-1.71 (m, 1H) |
| 22 | ¹H NMR (500 MHz, DMSO-d₆) δ 10.99 (s, 1H), 10.85 (s, 1H), 8.68-8.60 (m, 1H), 8.58 (s, 1H), 7.99-7.91 (m, 1H), 7.89 (d, J = 3.5 Hz, 1H), 7.74-7.66 (m, 1H), 7.62 (d, J = 7.9 Hz, 1H), 7.37 (t, J = 7.4 Hz, 1H), 4.96-4.67 (m, 1H), 3.14 (s, 3H), 2.81-2.75 (m, 3H), 1.54-1.39 (m, 1H), 1.17 (dq, J = 12.9, 6.4 Hz, 1H) |
| 24 | ¹H NMR (400 MHz, DMSO-d₆) δ 10.51 (s, 1H), 10.46 (s, 1H), 8.61 (m, 1H), 8.51 (s, 1H), 7.85 (s, 1H), 7.22 (m, 2H), 3.89 (d, J = 1.2 Hz, 3H), 2.79 (d, J = 4.4 Hz, 3H), 2.04 (s, 3H) |
| 25 | ¹H NMR (400 MHz, DMSO-d₆) δ 10.75 (s, 1H), 10.51 (s, 1H), 8.61 (m, 1H), 8.52 (s, 1H), 7.84 (s, 1H), 7.22 (m, 2H), 3.88 (d, J = 1.2 Hz, 3H), 2.79 (d, J = 4.4 Hz, 3H), 1.98 (m, 1H), 0.77 (m, 4H) |
| 26 | ¹H NMR (500 MHz, methanol-d₄) δ 8.53 (d, J = 2.5 Hz, 1H), 8.33 (s, 1H), 8.05 (s, 1H), 7.92 (dd, J = 8.9, 2.5 Hz, 1H), 7.42 (d, J = 8.4 Hz, 1H), 7.03-6.94 (m, 2H), 6.57 (d, J = 8.9 Hz, 1H), 3.88 (s, 3H), 2.91 (s, 3H) |

What is claimed is:
1. A compound having the following formula (I):

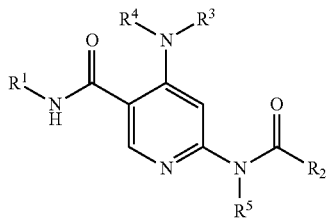

or a stereoisomer or pharmaceutically-acceptable salt thereof, wherein $R^1$ is $C_{1-3}$alkyl substituted by 0-7 deuterium atoms;

$R^2$ is methyl, ethyl, propyl, furyl, pyranyl, cyclopropyl, cyclobutyl or cyclohexyl, cyclopentyl, pyridyl, pyrimidinyl, pyridazinyl, pyrazinyl, quinolinyl or pyrrolopyridinyl, each group substituted as valence allows by 0-4 groups selected from $R^{2a}$;

$R^{2a}$ at each occurrence is independently hydrogen, =O, halo, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{1-6}$ haloalkyl, $-(CH_2)_r$-3-14 membered carbocycle substituted with 0-1 $R^a$ or a-$(CH_2)_r$-5-7 membered heterocycle comprising carbon atoms or 1-4 heteroatoms selected from N, O, and $S(O)_p$ substituted with 0-2 $R^a$;

$R^3$ has the formula,

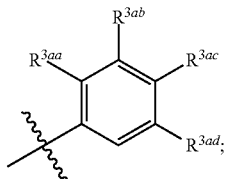

$R^{3aa}$ is $C_{1-6}$ alkyl substituted with 0-3 $R^{a2}$, $S(O)_pR^{c2}$ or $OR^{b2}$;

$R^{3ab}$, $R^{3ac}$, or $R^{3ad}$ are independently hydrogen, pyrazolyl, thiazolyl, pyrimidinyl or oxadiazolyl, each group substituted with 0-3 $R^{a2}$;

$R^{a2}$ is at each occurrence independently halo, OH or $C_{1-6}$ alkyl substituted with 0-3 $R^{f2}$;

$R^{b2}$ is hydrogen or $C_{1-6}$ alkyl substituted with 0-2 $R^{d2}$ $R^{c2}$ is $C_{1-6}$ alkyl substituted with 0-3 $R^{f2}$;

$R^{d2}$ independently at each occurrence is F or OH;

$R^{f2}$ is halo CN or OH;

$R^4$ and $R^5$ are independently hydrogen;

$R^{11}$ at each occurrence independently is hydrogen;

$R^a$ at each occurrence is hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$alkyl substituted with 0-3 $R^f$, $C_{1-6}$haloalkyl, $-(CH_2)_r$-3-14 membered carbocycle, or $-(CH_2)_r$-5-7 membered heterocycle comprising carbon atoms and 1-4 heteroatoms selected from N, O, and $S(O)_p$ substituted with 0-3 $R^f$;

$R^b$ at each occurrence is hydrogen, $C_{1-6}$ alkyl substituted with 0-3 $R^d$, $C_{1-6}$ haloalkyl, $C_{3-6}$ cycloalkyl substituted with 0-2 $R^d$, or $-(CH_2)_r$-5-7 membered heterocycle comprising carbon atoms and 1-4 heteroatoms selected from N, O, and $S(O)_p$ substituted with 0-3 $R^f$, or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ at each occurrence is independently hydrogen, F, Cl, Br, $OCF_3$, $CF_3$, CN, $NO_2$, $-OR^e$, $-(CH_2)_rC(O)R^c$, $-NR^eR^e$, $-NR^eC(O)OR^c$, $C_{1-6}$ alkyl or $(CH_2)_r$-phenyl substituted with 0-3 $R^f$;

$R^e$ at each occurrence is independently selected from hydrogen, $C_{1-6}$ alkyl, $C_{3-6}$ cycloalkyl and $(CH_2)_r$-phenyl substituted with 0-3 $R^f$;

$R^f$ independently at each occurrence is hydrogen, halo, CN, $NH_2$, OH, $C_{3-6}$ cycloalkyl, $CF_3$, $O(C_{1-6}alkyl)$ or a $-(CH_2)_r$-5-7 membered heteroaryl comprising carbon atoms and 1-4 heteroatoms selected from N, O, and $S(O)_p$;

p is 0, 1, or 2; and r is 0, 1, 2, 3, or 4.

2. The compound according to claim 1, or a stereoisomer or pharmaceutically-acceptable salt thereof, wherein $R^1$ is $CH_3$, $C_2H_5$, $CD_3$ or $CD_2CD_3$.

3. A compound according to claim 1, or a stereoisomer or pharmaceutically-acceptable salt thereof, wherein $R^2$ is cyclopropyl substituted by 0-4 groups selected from $R^{2a}$.

4. The compound according to claim 1, or a stereoisomer or pharmaceutically-acceptable salt thereof, wherein $R^{3aa}$ is $S(O)_2CH_3$ or $OCH_3$.

5. The compound according to claim 1, or a stereoisomer or pharmaceutically-acceptable salt thereof, wherein both $R^4$ and $R^5$ are hydrogen.

6. The compound according to claim 1, or a stereoisomer or pharmaceutically-acceptable salt thereof, having the formula:

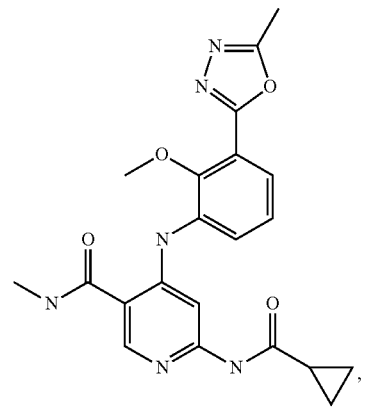

107
-continued
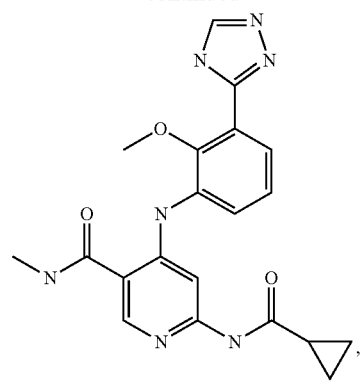
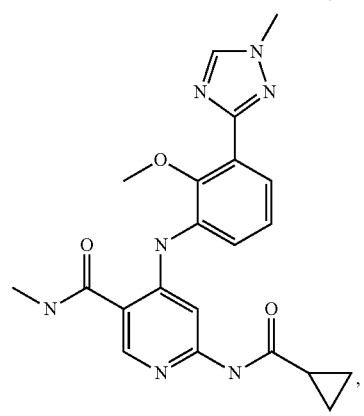
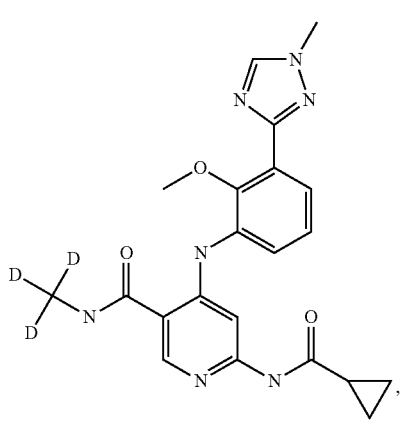
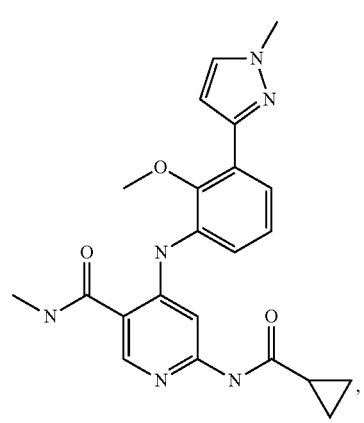
108
-continued
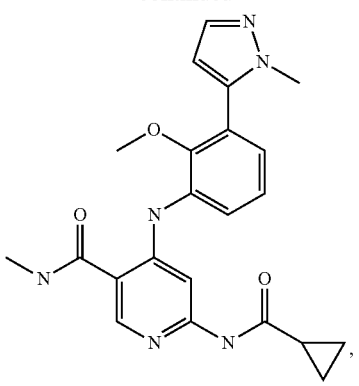
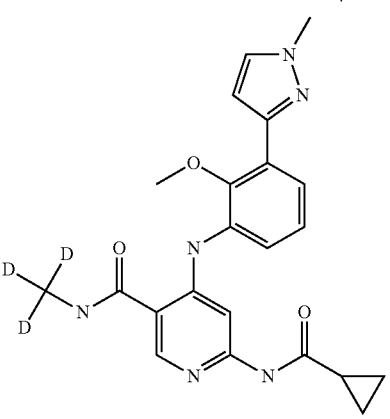
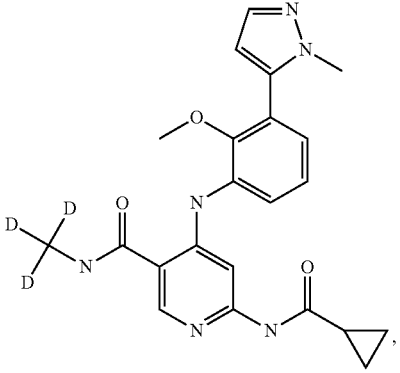
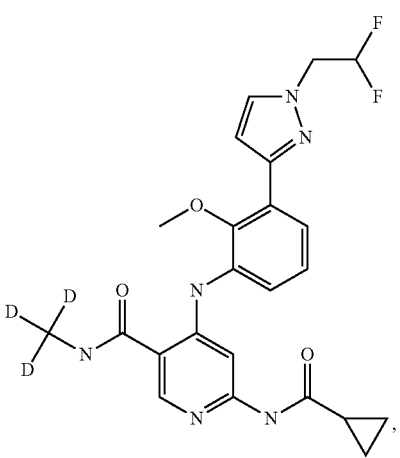

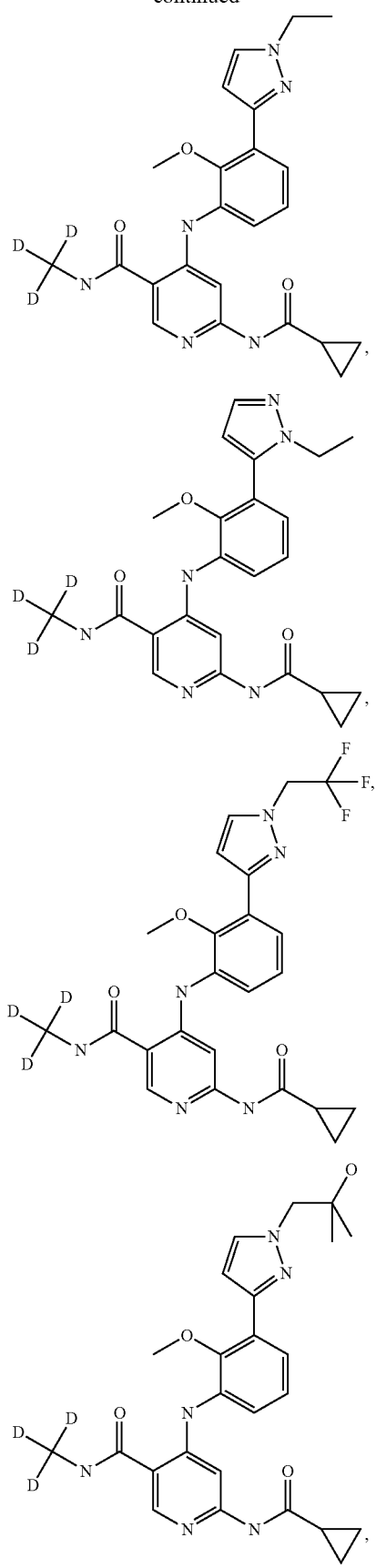
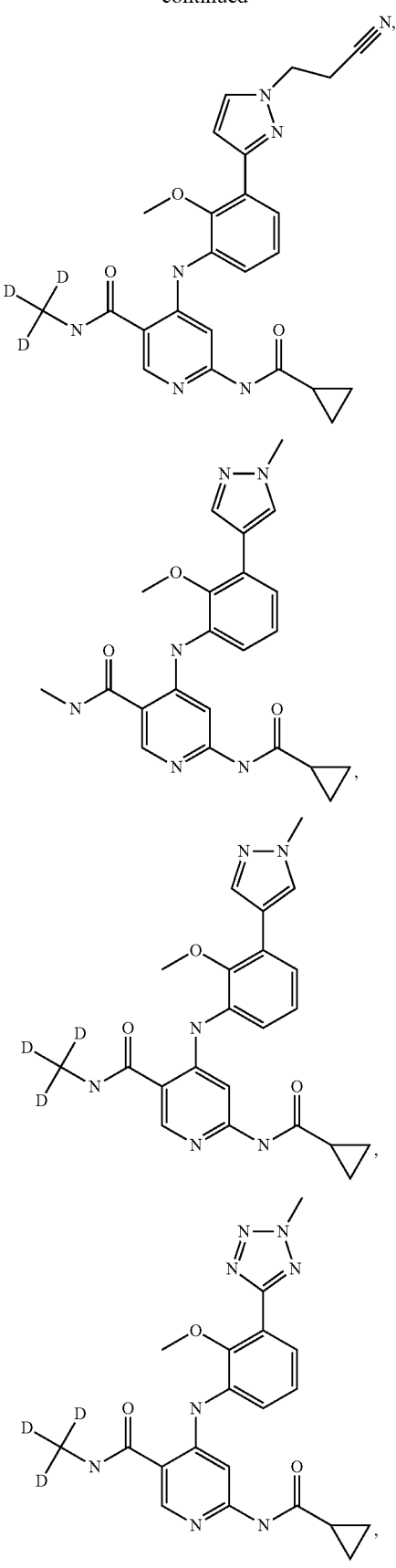

111
-continued
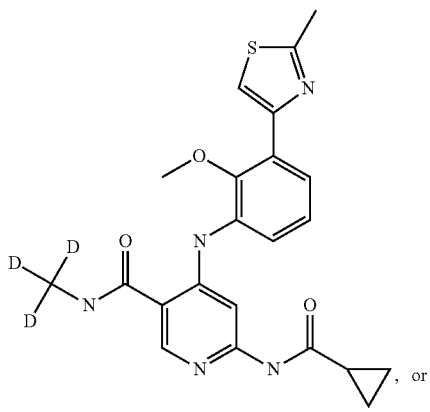
, or
112
-continued
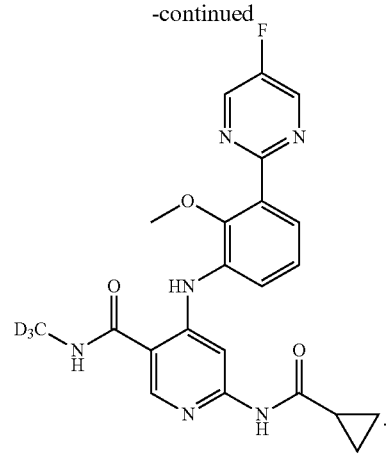
.
7. A pharmaceutical composition comprising one or more compounds according to claim 1 and a pharmaceutically acceptable carrier or diluent.
* * * * *

UNITED STATES PATENT AND TRADEMARK OFFICE
CERTIFICATE OF CORRECTION

PATENT NO. : 9,663,467 B2
APPLICATION NO. : 15/034915
DATED : May 30, 2017
INVENTOR(S) : Ryan Moslin et al.

It is certified that error appears in the above-identified patent and that said Letters Patent is hereby corrected as shown below:

In the Claims

Column 105, Line 33, Claim 1, delete "a-$(CH_2)_r$-5-7" and insert -- a —$(CH_2)_r$-5-7 --

Column 105, Line 54, Claim 1, after "0-2 $R^{d2}$" insert -- ; --

Column 105, Line 57, Claim 1, after "halo" insert -- , --

Signed and Sealed this
Fourth Day of December, 2018

Andrei Iancu
*Director of the United States Patent and Trademark Office*